(12) United States Patent
Hogle et al.

(10) Patent No.: US 6,844,171 B1
(45) Date of Patent: Jan. 18, 2005

(54) OLIGOMERIZATION OF HEPATITIS DELTA ANTIGEN

(75) Inventors: James M. Hogle, Newton, MA (US); Harmon J. Zuccola, Brookline, MA (US); David Filman, Auburndale, MA (US); Carl Elkin, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/347,175

(22) Filed: Jul. 1, 1999

Related U.S. Application Data

(60) Provisional application No. 60/091,609, filed on Jul. 2, 1998.

(51) Int. Cl.[7] ................................................. C12P 21/02

(52) U.S. Cl. ........................... 435/69.7; 435/5; 435/41; 435/69.3; 530/350

(58) Field of Search ............................. 435/69.3, 69.7, 435/41, 5; 530/350

(56) References Cited

FOREIGN PATENT DOCUMENTS

| EP | 0 251 575 | * | 1/1988 |
| EP | 0 485 347 | * | 5/1992 |
| WO | WO 96/20953 | * | 7/1996 |

OTHER PUBLICATIONS

Imazeki et al. (Journal of Virology , vol. 64, No. 11, pp. 5594–5599).*
Lee et al. (Virology, vol. 169, Feb. 1994, pp. 169–175).*
Kuo, M.Y.P., et al., "Initiation of Replication of the Human Hepatitis Delta Virus Genome from Cloned DNA: Role of Delta Antigen," *J. Virol.*, 63(5):1945–1950 (1989).
Wang, K.S., et al., "Structure, Sequence and Expression of the Hepatitis Delta (Delta) Viral Genome," *Nature*, 323(6088):508–14 (1986).
Wu, H., et al., "Human Hepatitis Delta Virus RNA Subfragments Contain an Autocleavage Activity," *Proc. Natl. Acad. Sci. USA*, 86:1831–1835 (1989).
Wu, H.N. and Lai, M.M.C., "Reversible Cleavage and Ligation of Hepatis Delta Virus RNA," *Science*, 243:652–654 (1989).
Sharmeen, L., et al., Antigenomic RNA of Human Hepatitis Delta Virus can Undergo Self–Cleavage, *J. Virol.*, 62:2674–2679 (1988).
Xia, Y.P., et al., "Characterization of Nuclear Targeting Signal of Hepatitis Delta Antigen: Nuclear Transport as a Protein Complex," *J. Virol.*, 66:914–921 (1992).
Lee, C.Z., et al., "RNA–Binding Activity of Hepatitis Delta Antigen Involves Two Arginine–Rich Motifs and is Required for Hepatitis Delta Virus RNA Replication," *J. Virol.*, 67:2221–2227 (1993).

Lazinski, D.W. and Taylor, J.M., "Relating Structure to Function in the Hepatitis Delta Virus Antigen," *J. Virol.*, 67:2672–2680 (1993).
deBruin, W., et al., "In Vitro Binding Properties of the Hepatitis Delta Antigens to the Hepatitis B Virus Envelope Proteins:Potential Significance for the Formation of Delta Particles," *Virus Res.*, 31:27–37 (1994).
Hwang, S.B. and Lai, M.M.C., "A Unique Conformation at the Carboxyl Terminus of the Small Hepatitis Delta Antigen Revealed by a Specific Monoclonal Antibody," *Virology*, 193:924–931 (1993).
Rozzelle, J.E., Jr., et al., "Self–Association of a Synthetic Peptide from the N Terminus of the Hepatitis Delta Virus Protein into an Immunoreactive Alpha–Helical Multimer," *Proc. Natl. Acad. Sci. USA*, 92:382–386 (1995).
Wang, J.G., et al., "Immunogenic Domains of Hepatitis Delta Virus Antigen: Peptide Mapping of Epitopes Recognized by Human and Woodchuck Antibodies," *J. Virol.*, 64:1108–1116 (1990).
Chang, M.F., et al., "Nuclear Localization Signals, but not Putative Leucine Zipper Motifs, are Essential for Nuclear Transport of Hepatitis Delta Antigen," *J. Virol.*, 66:6019–6027 (1992).
Poisson, F., et al., "Characterization of RNA–Binding Domains of Hepatitis Delta Antigen," *J. Gen. Virol.*, 74:2473–2478 (1993).
Poisson, F., et al., "Direct Investigation of Protein RNA–Binding Domains Using Digoxigenin–Labelled RNAs and Synthetic Peptides: Application to the Hepatitis Delta Antigen," *J. Virol. Methods*, 55(3):381–389 (1995).
Brazas, R. and Ganem, D., "A Cellular Homolog of Hepatitis Delta Antigen–Implications for Viral Replication and Evolution," *Science*, 274:90–94 (1996).
Soisson, S.M., et al., "Structural Basis for Ligand–Regulated Oligomerization of AraC," *Science*, 276:421–425 (1997).
Bussiere, D.E., et al., "Crystal Structure of the Replication Terminator Protein from *B. subtilis* at 2.6 Angstrom," *Cell*, 80:651–660 (1995).
Dingle, K., et al., "Initiation of Hepatitis Delta Virus Genome Replication," *J. Virol.*, 72(6):4783–4788 (1998).

(List continued on next page.)

Primary Examiner—Lynette R. F. Smith
Assistant Examiner—Robert A. Zeman
(74) Attorney, Agent, or Firm—Hamilton, Brook, Smith & Reynolds, P.C.

(57) ABSTRACT

This invention relates to HDAg peptides, including mutants, derivatives fragments and fusion molecules, including fusion proteins, coiled-coil oligomers, nucleic acid molecules, vectors comprising HDAg nucleic acid molecules, cells comprising said molecules, methods of multivalent expression and association of binding moieties of HDAg fusion molecules, and methods of use involving the molecules.

The molecules are particularly useful as a framework for multivalent display via formation of C-terminal and/or N-terminal fusion proteins or via chemical coupling to chemically reactive sidechains, e.g. cysteine residues.

17 Claims, 21 Drawing Sheets

OTHER PUBLICATIONS

Zuccola, H.J., et al., "Structural Basis of the Oligomerization of Hepatis Delta Antigen," *Structure*, 6(7):821–30 (1998).

Kuo, M., et al., "Characterization of Self–Cleaving RNA Sequences on the Genome and Antigenome of Human Hepatitis Delta Virus," *J. Virol.*, 62:4439–4444 (1988).

Sharmeen, L., et al., "Self–Ligating RNA Sequences on the Antigenome of Human Hepatitis Delta Virus," *J. Virol.*, 63:1428–1430 (1989).

Makino, S., et al., "Molecular Cloning and Sequencing of a Human Hepatitis Delta (Delta) Virus RNA," *Nature*, 329:343–346 (1987).

Chang, M.F., et al., "Mutational Analysis of Delta Antigen: Effect on Assembly and Replication of Hepatitis Delta Virus," *J. Virol.*, 68:646–653 (1994).

Chang, M.F., et al., "Human Hepatitis Delta Antigen is a Nuclear Phosphoprotein with RNA–binding Activity," *J. Virol.* 62:2403–2410 (1988).

Lin, J.H., et al., "Characterizaton of Hepatitis Delta Antigen: Specific Binding to Hepatitis Delta Virus RNA," *J. Virol.*, 64:4051–4058 (1990).

Chao, M., et al., "The Antigen of Hepatitis Delta Virus: Examination of In Vitro RNA–Binding Specificity" *J. Virol.*, 65:4057–4062 (1991).

Xia, Y.P. and Lai, M.M.C., "Oligomerization of Hepatitis Delta Antigen is Required for both the *trans*–activating and *trans*–dominant Inhibitory Activities of the Delta Antigen," *J. Virol.*, 66:6641–6648 (1992).

Wang, J.G., et al., "Hepatitis Delta Virus Antigen Forms Dimers and Multimeric Complexes In Vivo," *J. Virol.* 67:446–454 (1993).

Chang, M.F., et al., "Functional Motifs of Delta Antigen Essential for RNA Binding and Replication of Hepatitis Delta Virus," *J. Virol.*, 67:2529–2536 (1993).

* cited by examiner

|        | 1  |                              | 25 |                              | 49 |                              | 60 |
|--------|----|------------------------------|----|------------------------------|----|------------------------------|----|
| HDVAM  |    | GREDILEQWVSGRKKLEELERDLRKLKKKIKKLEEDNPWLGNIKGILGK |
| HDVL1  |    | GREEVLEQWVNSRKKAEELERDLRTKKKIKKLEDDNPWLGNIKGILGK |
| HDVD3  |    | GREEVLEQWVSGRKKLEELERDLRKVKKIKKLKDEHPWLGNIKGILGK |
| HDVNA  |    | GREEVLEQWVAGRKQEELERDLRKTKKIKKLEEENPWLGNIKGILGK |
| HDVS1  |    | TREETLEKWITAPKKAEELEKDLRKTRKTIKKLEEENPWLGNIVGII.R |
| HDVS2  |    | TREETLEKWITARKKAEELEKDLRKARKTIKKLEEENPWLGNILGII.R |
| HDVM1  |    | GREQILEQWVDGRKKLEELERDLRKIKKKIKKLEEENPWLGNVKGILGK |
| HDVM2  |    | GREQILEQWVDGRKKLEELERDLRKIKKKIKKLEEENPWLGNVKGILGK |
| HDVIT  |    | GREEILEQWVAGRKKLEELERDLRKTKKKLKKIEDENPWLGNIKGILGK |
| HDVWO  |    | GREEILEQWVAGRKKLEELERDLRKTKKKLKKIEDENPWLGNIKGILGK |
|        | *d | *d *                         | *  | *                            | *  | d d                          | d  |

Figure 1

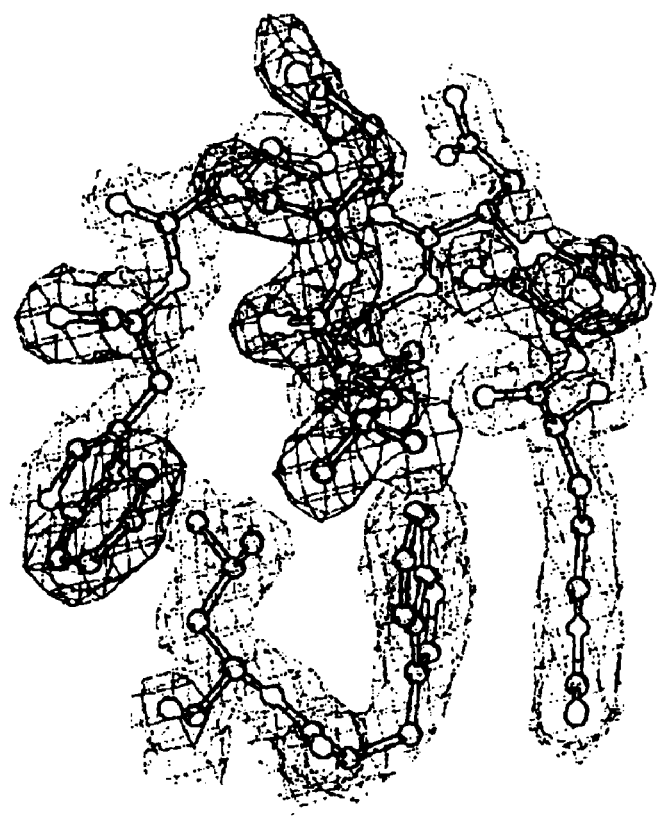
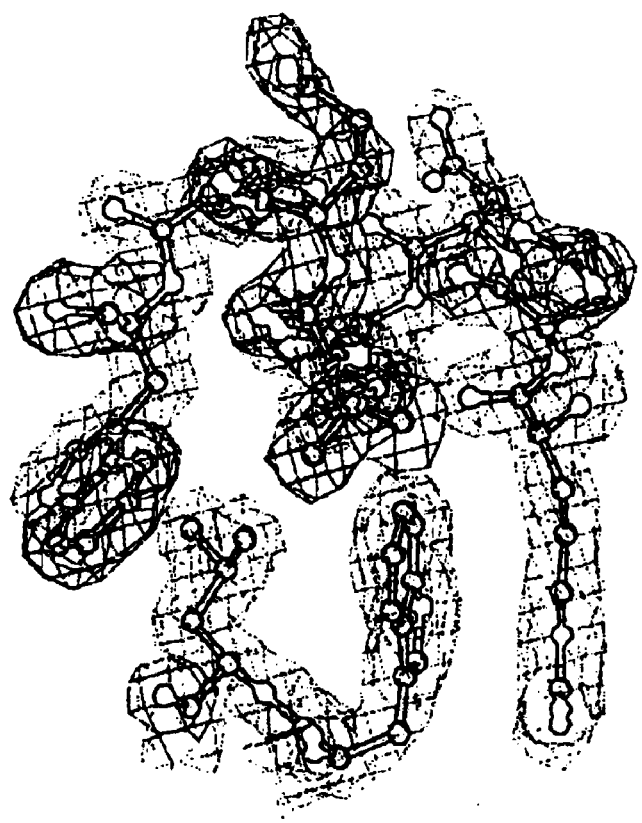
Figure 2

```
       12                                           48
       gabcdefgabcdefgabcdefgabcdefgabcdefga
       GREDILEQWVSGRKKLEELERDLRKLKKKIKKLEEDN
           NDEELKKIKKKLKRLDRELEELKKRGSVWQELIDERG
           agfedcbagfedcbagfedcbagfedcbagfedcbag
           48                                       12
```

Figure. 3C

```
          NdeI
           M   S   R   S   E   R   R   K   D   R   G   G   R   E   D   I   L   E
  GGGCATATGAGCCGTAGCGAACGTCGTAAAGATCGTGGCGGCCGTGAAGATATTCTGGAA
  CCCGTATACTCGGCATCGCTTGCAGCATTTCTAGCACCGCCGGCACTTCTATAAGACCTT

Q   W   V   S   G   R   K   K   L   E   E   L   E   R   D   L   R   K   L   K
  CAGTGGGTGAGCGGCCGTAAGAAGTTAGAGGAATTGGAACGTGATCTGCGTAAACTGAAA
  GTCACCCACTCGCCGGCATTCTTCAATCTCCTTAACCTTGCACTAGACGCATTTGACTTT

K   K   I   K   R   L   E   E   D   N   P   W   L   G   N   I   K   G   I   I
  AAGAAGATTAAGAAACTGGAAGAAGATAACCCGTGGTTGGGTAATATTAAAGGCATTATT
  TTCTTCTAATTCTTTGACCTTCTTCTATTGGGCACCAACCCATTATAATTTCCGTAATAA

G   K   K   D   K   D   G   E   G   A   P   P   A   K   K   L   R   M   D   Q
  GGCAAGAAAGATAAAGATGGCGAAGGCGCGCCGCCGGCGAAGAAACTGCGTATGGATCAG
  CCGTTCTTTCTATTTCTACCGCTTCCGCGCGGCGGCCGCTTCTTTGACGCATACCTAGTC

M   E   I   D   A   G   P   R   K   R   P   L   R   G   G   F   T   D   K   E
  ATGGAAATTGATGCGGGCCCGCGTAAACGTCCGCTGCGTGGCGGCTTTACCGATAAGGAA
  TACCTTTAACTACGCCCGGGCGCATTTGCAGGCGACGCACCGCCGAAATGGCTATTCCTT

R   Q   D   H   R   R   R   K   A   L   E   N   K   R   K   Q   L   S   S   G
  CGTCAGGACCATCGTCGTCGTAAAGCGCTGGAAAACAAACGTAAACAGCTGAGCAGCGGC
  GCAGTCCTGGTAGCAGCAGCATTTCGCGACCTTTTGTTTGCATTTGTCGACTCGTCGCCG

G   K   S   L   S   R   E   E   E   E   L   K   R   L   T   E   E   D   E
  GGCAAATCTCTGAGCCGTGAAGAAGAAGAAGAACTGAAACGTCTGACCGAAGAAGATGAA
  CCGTTTAGAGACTCGGCACTTCTTCTTCTTCTTGACTTTGCAGACTGGCTTCTTCTACTT

K   R   E   R   R   I   A   G   P   S   V   G   V   N   P   L   E   G   G
  AAACGTGAACGTCGTATTGCAGGTCCATCTGTTGGTGGTGTGAACCCGCTGGAAGGCGGC
  TTTGCACTTGCAGCATAACGTCCAGGTAGACAACCACCACACTTGGCGACCTTCCGCCG

S   R   G   A   P   G   G   G   F   V   P   S   M   Q   G   V   P   E   S   P
  AGCCGTGGTGCACCGGGCGGTGGCTTTGTGCCGTCTATGCAAGGTGTTCCAGAAAGCCCG
  TCGGCACCACGTGGCCCGCCACCGAAACACGGCAGATACGTTCCACAAGGTCTTTCGGGC

F   A   R   T   G   E   G   L   D   I   R   G   S   Q   G   F   P        NcoI
  TTTGCGCGTACCGGCGAAGGCCTGGATATTCGTGGCAGCCAGGGCTTTCCGTAAACCATGGCGC
  AAACGCGCATGGCCGCTTCCGGACCTATAAGCACCGTCGGTCCCGAAAGGCATTTGGTACCGCG
```

```
                         1                                                      50
sythetic ORF      ATGAGCCGta gCGAAcGtcG tAAAGAtCGt GGcGGccGtG AAGAtATtCT
wildtype ORF      ATGAGCCGgt cCGAAaGaaG gAAAGAcCGc GGgGGgaGgG AAGAcATcCT
         Identity ATGAGCCG-- -CGAA-G--G -AAAGA-CG- GG-GG--G-G AAGA-AT-CT 51                                                     100
sythetic ORF      gGAaCAGTGG GTGAGCGGcc GtAAGAAGTT AGAGGAAtTg GAacGtGAtC
wildtype ORF      cGAgCAGTGG GTGAGCGGaa GaAAGAAGTT AGAGGAAcTc GAgaGaGAcC
         Identity -GA-CAGTGG GTGAGCGG-- G-AAGAAGTT AGAGGAA-T- GA--G-GA-C 101                                                    155
sythetic ORF      TgCGtAAacT gAAaAAGAAg ATtAAGAAAC TgGAaGAAGA tAAcCCgTGG
wildtype ORF      TcCGgAAgtT aAAgAAGAAa ATcAAGAAAC TaGAgGAAGA cAAtCCcTGG
         Identity T-CG-AA--T -AA-AAGAA- AT-AAGAAAC T-GA-GAAGA -AA-CC-TGG 151                                                    205
sythetic ORF      tTGGGtAAtA TtAAAGGcAT tATtGGcAAG AAaGATAAaG ATGGcGAaGG
wildtype ORF      cTGGGaAAcA TcAAAGGaAT aATcGGaAAG AAgGATAAgG ATGGaCAgGG
         Identity -TGGG-AA-A T-AAAGG-AT -AT-GG-AAG AA-GATAA-G ATGG-GA-GG 201                                                    255
sythetic ORF      cGCgCCgCCG GCGAAGAAaC TgCGtATGGA tCAGATGGAa ATtGAtGCgG
wildtype ORF      gGCaCCcCCG GCGAAGAAgC TcCGgATGGA cCAGATGGAg ATaGAcGCcG
         Identity -GC-CC-CCG GCGAAGAA-C T-CG-ATGGA -CAGATGGA- AT-GA-GC-G 251                                                    305
sythetic ORF      GcCCgcGtAA acGtCCgCTg cGtGGcGGcT TtACCGAtAA GGAacGtCAG
wildtype ORF      GaCCtaGgAA gaGgCCtCTc aGgGGaGGaT TcACCGAcAA GGAgaGgCAG
         Identity G-CC--G-AA --G-CC-CT- -G-GG-GG-T T-ACCGA-AA GGA--G-CAG 301                                                    355
sythetic ORF      GAcCAtCGtC GtcGtAAaGC gCTgGAaAAC AAacGtAAaC AGCTgagcag
wildtype ORF      GAtCAcCGaC GaaGgAAGGC cCTcGAgAAC AAgaGgAAgC AGCTatcgtc
         Identity GA-CA-CG-C G--G-AA-GC -CT-GA-AAC AA--G-AA-C AGCT-----

351                                                    405
sythetic ORF      cGGcGGcAAa tctCTgAGCc GtGAaGAaGA AGAaGAACTg AAacGtCTGA
wildtype ORF      gGGgGGaAAg agcCTcAGCa GgGAgGAgGA AGAgGAACTt AAgaGgtTGA
         Identity -GG-GG-AA- ---CT-AGC- G-GA-GA-GA AGA-GAACT- AA--G--TGA 401                                                    455
sythetic ORF      CCGAaGAAGA tGAaAAAcGt GAAcGtCGtA TtGCaGGtCC aTCtGTTGGt
wildtype ORF      CCGAgGAAGA cGAgAAAaGg GAAaGaaGaA TaGCcGGcCC gTCgGTTGGg
         Identity CCGA-GAAGA -GA-AAA-G- GAA-G--G-A T-GC-GG-CC -TC-GTTGG- 451                                                    505
sythetic ORF      GGTGTGAACC CgCTgGAAGG cGGcagccGt GGtGCaCCgG GcGGtGGCTT
wildtype ORF      GGTGTGAACC CcCTcGAAGG tGGatcgaGg GGaGCgCCcG GgGGcGGCTT
         Identity GGTGTGAACC C-CT-GAAGG -GG-----G- GG-GC-CC-G G-GG-GGCTT 501                                                    555
sythetic ORF      tGTgCCgtct ATGCAAGGtG TtCCaGAaag CCCgTTtGCg CGtACCGGcG
wildtype ORF      cGTcCCcagc ATGCAAGGaG TcCCgGAgtc CCCcTTcGCt CGgACCGGgG
         Identity -GT-CC---- ATGCAAGG-G T-CC-GA--- CCC-TT-GC- CG-ACCGG-G 551                                                    603
sythetic ORF      AaGGcCTGGA tATtcGtGGc AGCCAGGGcT TtCCgTaaac cATggcgc
wildtype ORF      AgGGaCTGGA cATaaGgGGa AGCCAGGGaT TcCCaTggga tATactct
         Identity A-GG-CTGGA -AT--G-GG- AGCCAGGG-T T-CC-T---- -AT-----
```

Figure 15

```
  1  GGGCATATGA GCCGTAGCGA ACGTCGTAAA GATCGTGGCG GCCGTGAAGA
 51  TATTCTGGAA CAGTGGGTGA GCGGCCGTAA GAAGTTAGAG GAATTGGAAC
101  GTGATCTGCG TAAACTGAAA AAGAAGATTA AGAAACTGGA AGAAGATAAC
151  CCGTGGTTGG GTAATATTAA AGGCATTATT GGCAAGAAAG ATAAAGATGG
201  CGAAGGCGCG CCGCCGGCGA AGAAACTGCG TATGGATCAG ATGGAAATTG
251  ATGCGGGCCC GCGTAAACGT CCGCTGCGTG GCGGCTTTAC CGATAAGGAA
301  CGTCAGGACC ATCGTCGTCG TAAAGCGCTG AAAACAAAC GTAAACAGCT
351  GAGCAGCGGC GGCAAATCTC TGAGCCGTGA AGAAGAAGAA GAACTGAAAC
401  GTCTGACCGA AGAAGATGAA AAACGTGAAC GTCGTATTGC AGGTCCATCT
451  GTTGGTGGTG TGAACCCGCT GGAAGGCGGC AGCCGTGGTG CACCGGGCGG
501  TGGCTTTGTG CCGTCTATGC AAGGTGTTCC AGAAAGCCCG TTTGCGCGTA
551  CCGGCGAAGG CCTGGATATT CGTGGCAGCC AGGGCTTTCC GTAAACCATG
601  GCGC
```

Figure 16

|                  | 1                                                                                                    | 48 |
|---|---|---|
| wildtype HDAg-S  | MSRSERRK DRGGREDILE QWVSGRKKLE ELERDLRKLK KKIKKLEEDN |    |
| pR5DV5 plasmid   | MSRSERRK DRGGREDILE QWVSGRKKLE ELERDLRKLK KKIKKLEEDN |    |
| Identity         | MSRSERRK DRGGREDILE QWVSGRKKLE ELERDLRKLK KKIKKLEEDN |    |

|                  | 49                                                                                                   | 98 |
|---|---|---|
| wildtype HDAg-S  | PWLGNIKGII GKKDKDGEGA PPAKKLRMDQ MEIDAGPRKR PLRGGFTDKE |    |
| pR5DV5 plasmid   | PWLGNIKGII GKKDKDGEGA PPAKKLRMDQ MEIDAGPRKR PLRGGFTDKE |    |
| Identity         | PWLGNIKGII GKKDKDGEGA PPAKKLRMDQ MEIDAGPRKR PLRGGFTDKE |    |

|                  | 99                                                                                                   | 148 |
|---|---|---|
| wildtype HDAg-S  | RQDHRRRKAL ENKRKQLSSG GKSLSREEEE ELKRLTEEDE KRERRIAGPS |     |
| pR5DV5 plasmid   | RQDHRRRKAL ENKRKQLSSG GKSLSREEEE ELKRLTEEDE KRERRIAGPS |     |
| Identity         | RQDHRRRKAL ENKRKQLSSG GKSLSREEEE ELKRLTEEDE KRERRIAGPS |     |

|                  | 149                                                                                                  | 195 |
|---|---|---|
| wildtype HDAg-S  | VGGVNPLEGG SRGAPGGGFV PSMQGVPESP FARTGEGLDI RGSQGFP |     |
| pR5DV5 plasmid   | VGGVNPLEGG SRGAPGGGFV PSMQGVPESP FARTGEGLDI RGSQGFP |     |
| Identity         | VGGVNPLEGG SRGAPGGGFV PSMQGVPESP FARTGEGLDI RGSQGFP |     |

Figure 17 primer1
GGGCATATGAGCCGTAGCGAACGTCGTAAAGATCGTGGCGGCCGTGAAGATA
TTCTGGAACAGTGGGTGAGCGGCCGTAAGAAGTTAGAGGAA primer2
ATATTACCCAACCACGGGTTATCTTCTTCCAGTTTCTTAATCTTCTTTTT
CAGTTTACGCAGATCACGTTCCAATTCCTCTAACTTCTTACGGCC primer3
TAACCCGTGGTTGGGTAATATTAAAGGCATTATTGGCAAGAAAGATAAAG
ATGGCGAAGGCGCCGCCGGCGAAGAAACTGCGTATGGATCAG primer4
GATGGTCCTGACGTTCCTTATCGGTAAAGCCGCCACGCAGCGGACGTTTA
CGCGGGCCCGCATCAATTTCCATCTGATCCATACGCAGTTTCTT primer5
ATAAGGAACGTCAGGACCATCGTCGTCGTAAAGCGCTGGAAAACAAACGT
AAACAGCTGAGCAGCGGCGGCAAATCTCTGAGCCGTGAAGAAG primer6
CAACAGATGGACCTGCAATACGACGTTCACGTTTTTCATCTTCTTCGGTC
AGACGTTTCAGTTCTTCTTCTTCACGGCTCAGAGAT primer7
TATTGCAGGTCCATCTGTTGGTGGTGTGAACCCGCTGGAAGGCGGCAGCC
GTGGCGCGCCGGGCGGCGGCTTTGTCCGTCTATGCAAGGTGTTCCAGAA
A primer8
GCGCCATGGTTTACGGAAAGCCCTGGCTGCCACGAATATCCAGGCCTTCG
CCGGTACGCGCAAACGGGCTTTCTGGAACACCTTGCATAG primer9
GGGCATATGAGCCGTAGCGA primer10
GCGCCATGGTTTACGGAAAG

Figure 18

SEQUENCE LISTING

<160> NUMBER OF SEQ ID NOS: 35

<210> SEQ ID NO 1
<211> LENGTH: 49
<212> TYPE: PRT
<213> ORGANISM: Hepatitis Delta Virus

<400> SEQUENCE: 1

Gly Arg Glu Asp Ile Leu Glu Gln Trp Val Ser Gly Arg Lys Lys Leu
 1               5                  10                  15

Glu Glu Leu Glu Arg Asp Leu Arg Lys Leu Lys Lys Ile Lys Lys
            20                  25                  30

Leu Glu Glu Asp Asn Pro Trp Leu Gly Asn Ile Lys Gly Ile Ile Gly
        35                  40                  45

Lys

<210> SEQ ID NO 2
<211> LENGTH: 49
<212> TYPE: PRT
<213> ORGANISM: Hepatitis Delta Virus

<400> SEQUENCE: 2

Gly Arg Glu Glu Val Leu Glu Gln Trp Val Asn Ser Arg Lys Lys Ala
 1               5                  10                  15

Glu Glu Leu Glu Arg Asp Leu Arg Lys Thr Lys Lys Lys Ile Lys Lys
            20                  25                  30

Leu Glu Asp Asp Asn Pro Trp Leu Gly Asn Ile Lys Gly Ile Leu Gly
        35                  40                  45

Lys

<210> SEQ ID NO 3
<211> LENGTH: 49
<212> TYPE: PRT
<213> ORGANISM: Hepatitis Delta Virus

<400> SEQUENCE: 3

Gly Arg Glu Glu Val Leu Glu Gln Trp Val Ser Gly Arg Lys Lys Leu
 1               5                  10                  15

Glu Glu Leu Glu Arg Asp Leu Arg Lys Val Lys Lys Lys Ile Lys Lys
            20                  25                  30

Leu Glu Asp Glu His Pro Trp Leu Gly Asn Ile Lys Gly Ile Leu Gly
        35                  40                  45

Lys

<210> SEQ ID NO 4
<211> LENGTH: 49
<212> TYPE: PRT
<213> ORGANISM: Hepatitis Delta Virus

<400> SEQUENCE: 4

Gly Arg Glu Glu Val Leu Glu Gln Trp Val Ala Gly Arg Arg Lys Gln
 1               5                  10                  15

Glu Glu Leu Glu Arg Asp Leu Arg Lys Thr Lys Lys Lys Ile Lys Lys
            20                  25                  30

Leu Glu Glu Glu Asn Pro Trp Leu Gly Asn Ile Lys Gly Ile Leu Gly
        35                  40                  45

Lys

-continued

<210> SEQ ID NO 5
<211> LENGTH: 48
<212> TYPE: PRT
<213> ORGANISM: Hepatitis Delta Virus

<400> SEQUENCE: 5

Thr Arg Glu Glu Thr Leu Glu Lys Trp Ile Thr Ala Arg Lys Lys Ala
 1               5                  10                  15
Glu Glu Leu Glu Lys Asp Leu Arg Lys Thr Arg Lys Thr Ile Lys Lys
            20                  25                  30
Leu Glu Glu Asn Pro Trp Leu Gly Asn Ile Val Gly Ile Ile Arg
        35                  40                  45

<210> SEQ ID NO 6
<211> LENGTH: 48
<212> TYPE: PRT
<213> ORGANISM: Hepatitis Delta Virus

<400> SEQUENCE: 6

Thr Arg Glu Glu Thr Leu Glu Lys Trp Ile Thr Ala Arg Lys Lys Ala
 1               5                  10                  15
Glu Glu Leu Glu Lys Asp Leu Arg Lys Ala Arg Lys Thr Ile Lys Lys
            20                  25                  30
Leu Glu Glu Asn Pro Trp Leu Gly Asn Ile Leu Gly Ile Ile Arg
        35                  40                  45

<210> SEQ ID NO 7
<211> LENGTH: 49
<212> TYPE: PRT
<213> ORGANISM: Hepatitis Delta Virus

<400> SEQUENCE: 7

Gly Arg Glu Gln Ile Leu Glu Gln Trp Val Asp Gly Arg Lys Lys Leu
 1               5                  10                  15
Glu Glu Leu Glu Arg Asp Leu Arg Lys Ile Lys Lys Ile Lys Lys
            20                  25                  30
Leu Glu Glu Asn Pro Trp Leu Gly Asn Val Lys Gly Ile Leu Gly
        35                  40                  45
Lys

<210> SEQ ID NO 8
<211> LENGTH: 49
<212> TYPE: PRT
<213> ORGANISM: Hepatitis Delta Virus

<400> SEQUENCE: 8

Gly Arg Glu Glu Ile Leu Glu Gln Trp Val Ala Gly Arg Lys Lys Leu
 1               5                  10                  15
Glu Glu Leu Glu Arg Asp Leu Arg Lys Thr Lys Lys Leu Lys Lys
            20                  25                  30
Ile Glu Asp Glu Asn Pro Trp Leu Gly Asn Ile Lys Gly Ile Leu Gly
        35                  40                  45
Lys

<210> SEQ ID NO 9
<211> LENGTH: 37
<212> TYPE: PRT
<213> ORGANISM: Artificial Sequence
<220> FEATURE:

<223> OTHER INFORMATION: Residues 12-48 of delta 12-60 (Y)

<400> SEQUENCE: 9

```
Gly Arg Glu Asp Ile Leu Glu Gln Trp Val Ser Gly Arg Lys Lys Leu
 1               5                  10                  15
Glu Glu Leu Glu Arg Asp Leu Arg Lys Leu Lys Lys Ile Lys Lys
            20                  25                  30
Leu Glu Glu Asp Asn
        35
```

<210> SEQ ID NO 10
<211> LENGTH: 604
<212> TYPE: DNA
<213> ORGANISM: Artificial Sequence
<220> FEATURE:
<223> OTHER INFORMATION: Synthetic Gene for Optimized Expression of HDAg-S in E. Coli
<221> NAME/KEY: C -continued

```
<210> SEQ ID NO 11
<211> LENGTH: 195
<212> TYPE: PRT
<213> ORGANISM: Artificial Sequence
<220> FEATURE:
<223> OTHER INFORMATION: Amino acid sequence encoded by synthetic Gene
      for Optimized Expression of HDAg-S in E. Coli

<400> SEQUENCE: 11

Met Ser Arg Ser Glu Arg Arg Lys Asp Arg Gly Gly Arg Glu Asp Ile
 1               5                  10                  15

Leu Glu Gln Trp Val Ser Gly Arg Lys Lys Leu Glu Glu Leu Glu Arg
            20                  25                  30

Asp Leu Arg Lys Leu Lys Lys Ile Lys Lys Leu Glu Glu Asp Asn
        35                  40                  45

Pro Trp Leu Gly Asn Ile Gly Ile Ile Gly Lys Lys Asp Lys Asp
    50                  55                  60

Gly Glu Gly Ala Pro Pro Ala Lys Lys Leu Arg Met Asp Gln Met Glu
65                  70                  75                  80

Ile Asp Ala Gly Pro Arg Lys Arg Pro Leu Arg Gly Gly Phe Thr Asp
                85                  90                  95

Lys Glu Arg Gln Asp His Arg Arg Lys Ala Leu Glu Asn Lys Arg
            100                 105                 110

Lys Gln Leu Ser Ser Gly Gly Lys Ser Leu Ser Arg Glu Glu Glu
        115                 120                 125

Glu Leu Lys Arg Leu Thr Glu Glu Asp Glu Lys Arg Glu Arg Ile
    130                 135                 140

Ala Gly Pro Ser Val Gly Gly Val Asn Pro Leu Glu Gly Gly Ser Arg
145                 150                 155                 160

Gly Ala Pro Gly Gly Gly Phe Val Pro Ser Met Gln Gly Val Pro Glu
                165                 170                 175

Ser Pro Phe Ala Arg Thr Gly Glu Gly Leu Asp Ile Arg Gly Ser Gln
            180                 185                 190

Gly Phe Pro
        195

<210> SEQ ID NO 12
<211> LENGTH: 1679
<212> TYPE: DNA
<213> ORGANISM: Hepatitis Delta Virus

<400> SEQUENCE: 12
cttgagccaa gttccgagcg aggagacgcg gggggaggat cagctcccga gagggatgt      60 cacggtaaag agcattggaa cgtcggagaa actactccca agaagcaaag agaggtctca    120
ggaagcggac gagatcccca caacgccgga gaatctctgg aaggggaaag aggaaggtgg    180
aagaaaaagg ggcgggcctc ccgatccgag gggcccaacc tccagatctg gagagcactc    240
cggcccgaag ggttgagtag cacccagagg gaggaatcca ctcggagatg agcagagaaa    300
tcacctccag aggaccccct tcagcgaaca gaggcgcttc gagcgtaggg agtaagacca    360
tagcgatagg aggagatgct aggagtaggg ggagaccgaa gcgaggagga agtaaagaa    420 agcaacgggg ctagccggtg ggtgttccgc ccccgagag gggacgagtg aggcttatcc     480
cggggaattc gacttatcgt cccatctag cgggaccccg acccccttc gaaagtgacc      540 ggagggggtg ctgggaacac cggggaccag tggagccatg ggatgcccct ccgatgctc     600 gactccgact cccccccca aggtcgccc aggaatggcg ggaccccact ctgcagggtc      660
```

-continued

```
cgcgttccat cctttcttac ctgatggccg gcatggtccc agcctcctcg ctggcgccgg      720
ctgggcaaca ttccgagggg accgtccoct cggtaatggc gaatgggacc cacaaatctc      780
tctagattcc gatagagaat cgagagaaaa gtggctctcc cttagccatc cgagtggacg      840
tgcgtcctcc ttcggatgcc caggtcggac cgcgaggagg tggagatgcc atgccgaccc      900
gaagaggaaa gaaggacgcg agacgcaaac ctgtgagtgg aaacccgctt tattcactgg      960
ggtcgacaac tctggggaga aagggcgga tcggctggga agagtatatc ccatggaaat       1020
ccctggtttc ccctgatgtc cagcccctcc ccggtccgag agaaggggga ctccgggact      1080
ccctgcagac tggggacgaa gccgcccccg ggcgctcccc tcgatccacc ttcgaggggg      1140
ttcacacccc caaccggcgg gccggctact cttctttccc ttctctcgtc ttcctcggtc      1200
aacctcctga gttcctcttc ttcctccttg ctgaggttct tgcctcccgc cgatagctgc      1260
ttcttcttgt tctcgagggc cttccttcgt cggtgatcct gcctctcctt gtcggtgaat      1320
cctcccctga gaggcctctt cctaggtccg gagtctacct ccatctggtc cgttcgggcc      1380
ctcttcgccg ggggagcccc ctctccatcc ttatccttct ttccgagaat tcctttgatg      1440
ttccccagcc agggattttc gtcctcaatc ttcttgagtt tcttctttgt cttccggagg      1500
tctctctcga gttcctctaa cttctttctt ccggccaccc actgctcgag gatctcttct      1560 ctcccccgc ggttcttcct cgactcggac cggctcatct cggctagagg cggcagtcct      1620
cagtactctt actcttttct gtaaagagga gactgctgga ctcgccgccc gagcccgag       1679
```

<210> SEQ ID NO 13
<211> LENGTH: 1683
<212> TYPE: DNA
<213> ORGANISM: Hepatitis Delta Virus

<400> SEQUENCE: 13

```
atgggccaag ttccgaacaa ggatccgcgg ggaggacgga tcacctcccg agagggtaa       60 gtcgctaaag agcattggaa cgtcggagat acaactccca agaaggaaaa aagagaaagc      120
aagaagcgga agaattcccc ataacgctag tgaaactcta ggaagggaaa agaggtgcga      180
tggaaaaaga ggaggtgggc ctcccgatcc gagggtcccg gtggccaagt ttggaggaca      240
ctccggcccg aagggttgag gatcccccag agggaggaag ccacacgag tagaacagag       300 aaatcacctc cagaggaccc cttcagcgaa cagaggggcg catcgcgaga gggagtagac      360
catagcgatg ggaggggatg ctaggagtta ggggagaccg aagcgaggag gaaagtaaag      420
agagcagcgg ggctagtcgg tgggtgttcc gccccccgag aggggacgag tgaggcttat      480
cccggggaat cgacttatc gtccccacat agcagagccc cggaccccct ttcaaagcga      540
ccgagggggg tgactttgaa cattggggac cagtggagcc atgggatgct cctcccgatt      600
ccgcccaaac tccttccccc caagggtcg cccaggaatg gcgggacccc actctgcagg       660
gtccgcgttc catcctttct tacctgatgg ccggcatggt cccagcctcc tcgctggcgc      720
cggctgggca acattccgag gggaccgtcc cctcggtaat ggcgaatggg acgcacaaat      780
ctctctagct tcccagagag aagcgagaga aagtggctc tcccttggcc atccgagtgg      840
acgtacgtcc tccttcggat gcccaggtcg daccgcgagg aggtggagat gccatgccga      900
cccgaagagg aaagaaggac gcgagacgca aacctgtgag tggaaaccg ctttattcac      960 tggggtcgac aactctgggg agagaaggga gggtcggctg gaagagtat atcccatggg       1020 aatccctggc ttccccttat gtccagtccc tcccggtcc gagcgaaggg ggactccggg       1080
actccttgca tgctggggac gaagccgccc ccggggcgctc ccctcgatcc accttcgagg      1140
```

-continued

```
gggttcacac ccccaaccga cgggccggct attcttcttt ccctttcctc gtcttcctcg   1200
gtcaacctct taagttcctc ttcctcctcc ctgctgaggc tctttccccc cgacgatagc   1260
tgcttcctct tgttctcgag ggccttcctt cgtcggtgat cctgcctctc cttgtcggtg   1320
aatcctcccc tgagaggcct cttcctaggt ccggcgtcta tctccatctg gtccatccgg   1380
agcttcttcg ccggggggtgc ccctctccca tccttatcct tctttccgat tattcctttg   1440
atgtttccca gccagggatt gtcttcctct agtttcttga ttttcttctt taacttccgg   1500
aggtctctct cgagttcctc taacttcttt cttccgctca cccactgctc gaggatgtct   1560
tccctccccc cgcggtcttt ccttctttcg daccggctca tcttcgacta gaggcgacgg   1620
tcctcagtac tcttactctt ttctgtaaag aggagactgc tggccctgtc gcccaagctc   1680
gag                                                                 1683

<210> SEQ ID NO 14
<211> LENGTH: 645
<212> TYPE: DNA
<213> ORGANISM: Hepatitis Delta Virus
<220> FEATURE:
<221> NAME/KEY: CDS
<222> LOCATION: (1)...(642)

<400> SEQUENCE: 14 atg agc cgg tcc gaa aga agg aaa gac cgc ggg ggg agg gaa gac atc      48
Met Ser Arg Ser Glu Arg Arg Lys Asp Arg Gly Gly Arg Glu Asp Ile
1               5                   10                  15 ctc gag cag tgg gtg agc gga aga aag aag tta gag gaa ctc gag aga      96
Leu Glu Gln Trp Val Ser Gly Arg Lys Lys Leu Glu Glu Leu Glu Arg
            20                  25                  30 gac ctc cgg aag tta aag aag aaa atc aag aaa cta gag gaa gac aat     144
Asp Leu Arg Lys Leu Lys Lys Lys Ile Lys Lys Leu Glu Glu Asp Asn
        35                  40                  45 ccc tgg ctg gga aac atc aaa gga ata atc gga aag aag gat aag gat     192
Pro Trp Leu Gly Asn Ile Lys Gly Ile Ile Gly Lys Lys Asp Lys Asp
    50                  55                  60 gga gag ggg gca ccc ccg gcg aag aag ctc cgg atg gac cag atg gag     240
Gly Glu Gly Ala Pro Pro Ala Lys Lys Leu Arg Met Asp Gln Met Glu
65                  70                  75                  80 ata gac gcc gga cct agg aag agg cct ctc agg gga gga ttc acc gac     288
Ile Asp Ala Gly Pro Arg Lys Arg Pro Leu Arg Gly Gly Phe Thr Asp
                85                  90                  95 aag gag agg cag gat cac cga cga agg aag gcc ctc gag aac aag agg     336
Lys Glu Arg Gln Asp His Arg Arg Lys Ala Leu Glu Asn Lys Arg
            100                 105                 110 aag cag cta tcg tcg ggg gga aag agc ctc agc agg gag gag gaa gag     384
Lys Gln Leu Ser Ser Gly Gly Lys Ser Leu Ser Arg Glu Glu Glu Glu
        115                 120                 125 gaa ctt aag agg ttg acc gag gaa gac gag aaa agg gaa aga aga ata     432
Glu Leu Lys Arg Leu Thr Glu Glu Asp Glu Lys Arg Glu Arg Arg Ile
    130                 135                 140 gcc ggc ccg tcg gtt ggg ggt gtg aac ccc ctc gaa ggt gga tcg agg     480
Ala Gly Pro Ser Val Gly Gly Val Asn Pro Leu Glu Gly Gly Ser Arg
145                 150                 155                 160 gga gcg ccc ggg ggc ggc ttc gtc ccc agc atg caa gga gtc ccg gag     528
Gly Ala Pro Gly Gly Gly Phe Val Pro Ser Met Gln Gly Val Pro Glu
                165                 170                 175 tcc ccc ttc gct cgg acc ggg gag gga ctg gac ata agg gga agc cag     576
Ser Pro Phe Ala Arg Thr Gly Glu Gly Leu Asp Ile Arg Gly Ser Gln
            180                 185                 190
```

```
gga ttc cca tgg gat ata ctc ttc cca gcc gac cct ccc ttc tct ccc       624
Gly Phe Pro Trp Asp Ile Leu Phe Pro Ala Asp Pro Pro Phe Ser Pro
        195                 200                 205 cag agt tgt cga ccc cag tga                                            645
Gln Ser Cys Arg Pro Gln
    210
```

<210> SEQ ID NO 15
<211> LENGTH: 214
<212> TYPE: PRT
<213> ORGANISM: Hepatitis Delta Virus

<400> SEQUENCE: 15

```
Met Ser Arg Ser Glu Arg Arg Lys Asp Arg Gly Gly Arg Glu Asp Ile
 1               5                  10                  15

Leu Glu Gln Trp Val Ser Gly Arg Lys Lys Leu Glu Glu Leu Glu Arg
            20                  25                  30

Asp Leu Arg Lys Leu Lys Lys Ile Lys Lys Leu Glu Glu Asp Asn
        35                  40                  45

Pro Trp Leu Gly Asn Ile Lys Gly Ile Ile Gly Lys Lys Asp Lys Asp
 50                  55                  60

Gly Glu Gly Ala Pro Pro Ala Lys Lys Leu Arg Met Asp Gln Met Glu
 65                  70                  75                  80

Ile Asp Ala Gly Pro Arg Lys Arg Pro Leu Arg Gly Gly Phe Thr Asp
                85                  90                  95

Lys Glu Arg Gln Asp His Arg Arg Lys Ala Leu Glu Asn Lys Arg
                100                 105                 110

Lys Gln Leu Ser Ser Gly Gly Lys Ser Leu Ser Arg Glu Glu Glu Glu
            115                 120                 125

Glu Leu Lys Arg Leu Thr Glu Glu Asp Glu Lys Arg Glu Arg Arg Ile
130                 135                 140

Ala Gly Pro Ser Val Gly Val Asn Pro Leu Glu Gly Gly Ser Arg
145                 150                 155                 160

Gly Ala Pro Gly Gly Phe Val Pro Ser Met Gln Gly Val Pro Glu
                165                 170                 175

Ser Pro Phe Ala Arg Thr Gly Glu Gly Leu Asp Ile Arg Gly Ser Gln
            180                 185                 190

Gly Phe Pro Trp Asp Ile Leu Phe Pro Ala Asp Pro Pro Phe Ser Pro
        195                 200                 205

Gln Ser Cys Arg Pro Gln
    210
```

<210> SEQ ID NO 16
<211> LENGTH: 214
<212> TYPE: PRT
<213> ORGANISM: Hepatitis Delta Virus

<400> SEQUENCE: 16

```
Met Ser Arg Ser Glu Arg Arg Lys Asp Arg Gly Gly Arg Glu Asp Ile
 1               5                  10                  15

Leu Glu Gln Trp Val Ser Gly Arg Lys Lys Leu Glu Glu Leu Glu Arg
            20                  25                  30

Asp Leu Arg Lys Leu Lys Lys Ile Lys Lys Leu Glu Glu Asp Asn
        35                  40                  45

Pro Trp Leu Gly Asn Ile Lys Gly Ile Ile Gly Lys Lys Asp Lys Asp
 50                  55                  60
```

-continued

```
Gly Glu Gly Ala Pro Ala Lys Lys Leu Arg Met Asp Gln Met Glu
65                  70                  75                  80

Ile Asp Ala Gly Pro Arg Lys Arg Pro Leu Arg Gly Gly Phe Thr Asp
                85                  90                  95

Lys Glu Arg Gln Asp His Arg Arg Lys Ala Leu Glu Asn Lys Arg
            100                 105                 110

Lys Gln Leu Ser Ser Gly Gly Lys Ser Leu Ser Arg Glu Glu Glu Glu
            115                 120                 125

Glu Leu Lys Arg Leu Thr Glu Glu Asp Glu Lys Arg Glu Arg Arg Ile
    130                 135                 140

Ala Gly Pro Ser Val Gly Val Asn Pro Leu Glu Gly Gly Ser Arg
145                 150                 155                 160

Gly Ala Pro Gly Gly Pro Val Pro Ser Met Gln Gly Val Pro Glu
                165                 170                 175

Ser Pro Phe Ala Arg Thr Gly Glu Gly Leu Asp Ile Arg Gly Ser Gln
                180                 185                 190

Gly Phe Pro Trp Asp Ile Leu Phe Pro Ala Asp Pro Pro Phe Ser Pro
            195                 200                 205

Gln Ser Cys Arg Pro Gln
    210
```

<210> SEQ ID NO 17
<211> LENGTH: 214
<212> TYPE: PRT
<213> ORGANISM: Hepatitis Delta Virus

<400> SEQUENCE: 17

```
Met Ser Arg Ser Glu Ser Arg Lys Asn Arg Gly Gly Arg Glu Glu Ile
1               5                   10                  15

Leu Glu Gln Trp Val Ala Gly Arg Lys Lys Leu Glu Glu Leu Glu Arg
                20                  25                  30

Asp Leu Arg Lys Thr Lys Lys Lys Leu Lys Lys Ile Glu Asp Glu Asn
            35                  40                  45

Pro Trp Leu Gly Asn Ile Lys Gly Ile Leu Gly Lys Lys Asp Lys Asp
    50                  55                  60

Gly Glu Gly Ala Pro Pro Ala Lys Arg Ala Arg Thr Asp Gln Met Glu
65                  70                  75                  80

Val Asp Ser Gly Pro Arg Lys Arg Pro Leu Arg Gly Gly Phe Thr Asp
                85                  90                  95

Lys Glu Arg Gln Asp His Arg Arg Lys Ala Leu Glu Asn Lys Lys
            100                 105                 110

Lys Gln Leu Ser Ala Gly Gly Lys Asn Leu Ser Lys Glu Glu Glu Glu
            115                 120                 125

Glu Leu Arg Arg Leu Thr Glu Glu Asp Glu Arg Arg Glu Arg Arg Val
    130                 135                 140

Ala Gly Pro Pro Val Gly Val Asn Pro Leu Glu Gly Gly Ser Arg
145                 150                 155                 160

Gly Ala Pro Gly Gly Pro Val Pro Ser Leu Gln Gly Val Pro Glu
                165                 170                 175

Ser Pro Phe Ser Arg Thr Gly Glu Gly Leu Asp Ile Arg Gly Asn Gln
                180                 185                 190

Gly Phe Pro Trp Asp Ile Leu Phe Pro Ala Asp Pro Pro Phe Ser Pro
            195                 200                 205

Gln Ser Cys Arg Pro Gln
    210
```

```
<210> SEQ ID NO 18
<211> LENGTH: 37
<212> TYPE: PRT
<213> ORGANISM: Artificial Sequence
<220> FEATURE:
<223> OTHER INFORMATION: Synthetic peptide from the multimer-forming
      domain of HDAg

<400> SEQUENCE: 18

Lys Lys Leu Glu Glu Leu Glu Arg Asp Leu Arg Lys Leu Lys Lys
 1               5                  10                  15

Ile Lys Lys Leu Glu Glu Asp Asn Pro Trp Leu Gly Asn Ile Lys Gly
            20                  25                  30

Ile Ile Gly Lys Tyr
         35

<210> SEQ ID NO 19
<211> LENGTH: 38
<212> TYPE: PRT
<213> ORGANISM: Hepatitis Delta Virus
<220> FEATURE:
<223> OTHER INFORMATION: Synthetic peptide from the multimer-forming
      domain of HDAg

<400> SEQUENCE: 19

Gly Arg Glu Asp Ile Leu Glu Gln Trp Val Ser Gly Arg Lys Lys Leu
 1               5                  10                  15

Glu Glu Leu Glu Arg Asp Leu Arg Lys Leu Lys Lys Ile Lys Lys
            20                  25                  30

Leu Glu Glu Asp Asn Pro
         35

<210> SEQ ID NO 20
<211> LENGTH: 50
<212> TYPE: PRT
<213> ORGANISM: Artificial Sequence
<220> FEATURE:
<223> OTHER INFORMATION: Synthetic peptide from the multimer-forming
      domain of HDAg

<400> SEQUENCE: 20

Gly Arg Glu Asp Ile Leu Glu Gln Trp Val Ser Gly Arg Lys Lys Leu
 1               5                  10                  15

Glu Glu Leu Glu Arg Asp Leu Arg Lys Leu Lys Lys Ile Lys Lys
            20                  25                  30

Leu Glu Glu Asp Asn Pro Trp Leu Gly Asn Ile Lys Gly Ile Ile Gly
         35                  40                  45

Lys Tyr
     50

<210> SEQ ID NO 21
<211> LENGTH: 598
<212> TYPE: DNA
<213> ORGANISM: Artificial Sequence
<220> FEATURE:
<223> OTHER INFORMATION: Synthetic HDAg gene for optimized expression
      in E. Coli
<221> NA

```
                1               5                     10                      15
ctg gaa cag tgg gtg agc ggc cgt aag aag tta gag gaa ttg gaa cgt              96
Leu Glu Gln Trp Val Ser Gly Arg Lys Lys Leu Glu Glu Leu Glu Arg
                        20                    25                    30 gat ctg cgt aaa ctg aaa aag aag att aag aaa ctg gaa gaa gat aac             144
Asp Leu Arg Lys Leu Lys Lys Lys Ile Lys Lys Leu Glu Glu Asp Asn
                35                    40                    45 ccg tgg ttg ggt aat att aaa ggc att att ggc aag aaa gat aaa gat             192
Pro Trp Leu Gly Asn Ile Lys Gly Ile Ile Gly Lys Lys Asp Lys Asp
        50                    55                    60 ggc gaa ggc gcg ccg ccg gcg aag aaa ctg cgt atg gat cag atg gaa             240
Gly Glu Gly Ala Pro Pro Ala Lys Lys Leu Arg Met Asp Gln Met Glu
65                      70                    75                      80 att gat gcg ggc ccg cgt aaa cgt ccg ctg cgt ggc ggc ttt acc gat             288
Ile Asp Ala Gly Pro Arg Lys Arg Pro Leu Arg Gly Gly Phe Thr Asp
                        85                    90                    95 aag gaa cgt cag gac cat cgt cgt cgt aaa gcg ctg gaa aac aaa cgt             336
Lys Glu Arg Gln Asp His Arg Arg Arg Lys Ala Leu Glu Asn Lys Arg
                100                   105                   110 aaa cag ctg agc agc ggc ggc aaa tct ctg agc cgt gaa gaa gaa gaa             384
Lys Gln Leu Ser Ser Gly Gly Lys Ser Leu Ser Arg Glu Glu Glu Glu
            115                   120                   125 gaa ctg aaa cgt ctg acc gaa gaa gat gaa aaa cgt gaa cgt cgt att             432
Glu Leu Lys Arg Leu Thr Glu Glu Asp Glu Lys Arg Glu Arg Arg Ile
130                   135                   140 gca ggt cca tct gtt ggt ggt gtg aac ccg ctg gaa ggc ggc agc cgt             480
Ala Gly Pro Ser Val Gly Gly Val Asn Pro Leu Glu Gly Gly Ser Arg
145                   150                   155                   160 ggt gca ccg ggc ggt ggc ttt gtg ccg tct atg caa ggt gtt cca gaa             528
Gly Ala Pro Gly Gly Gly Phe Val Pro Ser Met Gln Gly Val Pro Glu
                165                   170                   175 agc ccg ttt gcg cgt acc ggc gaa ggc ctg gat att cgt ggc agc cag             576
Ser Pro Phe Ala Arg Thr Gly Glu Gly Leu Asp Ile Arg Gly Ser Gln
                180                   185                   190 ggc ttt ccg taaaccatgg cgc                                                   598
Gly Phe Pro
        195
```

<210> SEQ ID NO 22
<211> LENGTH: 195
<212> TYPE: PRT
<213> ORGANISM: Artificial Sequence
<220> FEATURE:
<223> OTHER INFORMATION: Amino acid sequence encoded by synthetic gene
      for optimized HDAg expression in E. Coli

<400> SEQUENCE: 22

Met Ser Arg Ser Glu Arg Arg Lys Asp Arg Gly Gly Arg Glu Asp Ile
1               5                   10                  15

Leu Glu Gln Trp Val Ser Gly Arg Lys Lys Leu Glu Glu Leu Glu Arg
                20                  25                  30

Asp

```
                Lys Glu Arg Gln Asp His Arg Arg Lys Ala Leu Glu Asn Lys Arg
                            100                 105                 110

Lys Gln Leu Ser Ser Gly Gly Lys Ser Leu Ser Arg Glu Glu Glu
                        115                 120                 125

Glu Leu Lys Arg Leu Thr Glu Glu Asp Glu Lys Arg Glu Arg Arg Ile
                    130                 135                 140

Ala Gly Pro Ser Val Gly Gly Val Asn Pro Leu Glu Gly Gly Ser Arg
                145                 150                 155                 160

Gly Ala Pro Gly Gly Gly Phe Val Pro Ser Met Gln Gly Val Pro Glu
                                165                 170                 175

Ser Pro Phe Ala Arg Thr Gly Glu Gly Leu Asp Ile Arg Gly Ser Gln
                            180                 185                 190

Gly Phe Pro

<210> SEQ ID NO 23
<211> LENGTH: 598
<212> TYPE: DNA
<213> ORGANISM: Hepatitis Delta Virus
<220> FEATURE:
<221> NAME/KEY: CDS
<222> LOCATION: (1)...(598)

<400> SEQUENCE: 23
```

| | | | | | | | | | | | | | | | | |
|---|---|---|---|---|---|---|---|---|---|---|---|---|---|---|---|---|
| atg | agc | cgg | tcc | gaa | aga | agg | aaa | gac | cgc | ggg | ggg | agg | gaa | gac | atc | 48 |
| Met | Ser | Arg | Ser | Glu | Arg | Arg | Lys | Asp | Arg | Gly | Gly | Arg | Glu | Asp | Ile | |
| 1 | | | | 5 | | | | | 10 | | | | | 15 | | |
| ctc | gag | cag | tgg | gtg | agc | gga | aga | aag | aag | tta | gag | gaa | ctc | gag | aga | 96 |
| Leu | Glu | Gln | Trp | Val | Ser | Gly | Arg | Lys | Lys | Leu | Glu | Glu | Leu | Glu | Arg | |
| | | | | 20 | | | | | 25 | | | | | 30 | | |
| gac | ctc | cgg | aag | tta | aag | aag | aaa | atc | aag | aaa | cta | gag | gaa | gac | aat | 144 |
| Asp | Leu | Arg | Lys | Leu | Lys | Lys | Lys | Ile | Lys | Lys | Leu | Glu | Glu | Asp | Asn | |
| | | 35 | | | | | 40 | | | | | 45 | | | | |
| ccc | tgg | ctg | gga | aac | atc | aaa | gga | ata | atc | gga | aag | aag | gat | aag | gat | 192 |
| Pro | Trp | Leu | Gly | Asn | Ile | Lys | Gly | Ile | Ile | Gly | Lys | Lys | Asp | Lys | Asp | |
| | 50 | | | | | 55 | | | | | 60 | | | | | |
| gga | gag | ggg | gca | ccc | ccg | gcg | aag | aag | ctc | cgg | atg | gac | cag | atg | gag | 240 |
| Gly | Glu | Gly | Ala | Pro | Pro | Ala | Lys | Lys | Leu | Arg | Met | Asp | Gln | Met | Glu | |
| 65 | | | | | 70 | | | | | 75 | | | | | 80 | |
| ata | gac | gcc | gga | cct | agg | aag | agg | cct | ctc | agg | gga | gga | ttc | acc | gac | 288 |
| Ile | Asp | Ala | Gly | Pro | Arg | Lys | Arg | Pro | Leu | Arg | Gly | Gly | Phe | Thr | Asp | |
| | | | | 85 | | | | | 90 | | | | | 95 | | |
| aag | gag | agg | cag | gat | cac | cga | cga | agg | aag | gcc | ctc | gag | aac | aag | agg | 336 |
| Lys | Glu | Arg | Gln | Asp | His | Arg | Arg | Lys | Ala | Leu | Glu | Asn | Lys | Arg | | |
| | | | | 100 | | | | | 105 | | | | | 110 | | |
| aag | cag | cta | tcg | tcg | ggg | gga | aag | agc | ctc | agc | agg | gag | gag | gaa | gag | 384 |
| Lys | Gln | Leu | Ser | Ser | Gly | Gly | Lys | Ser | Leu | Ser | Arg | Glu | Glu | Glu | Glu | |
| | | | | 115 | | | | | 120 | | | | | 125 | | |
| gaa | ctt | aag | agg | ttg | acc | gag | gaa | gac | gag | aaa | agg | gaa | aga | aga | ata | 432 |
| Glu | Leu | Lys | Arg | Leu | Thr | Glu | Glu | Asp | Glu | Lys | Arg | Glu | Arg | Arg | Ile | |
| | | | 130 | | | | | 135 | | | | | 140 | | | |
| gcc | ggc | ccg | tcg | gtt | ggg | ggt | gtg | aac | ccc | ctc | gaa | ggt | gga | tcg | agg | 480 |
| Ala | Gly | Pro | Ser | Val | Gly | Gly | Val | Asn | Pro | Leu | Glu | Gly | Gly | Ser | Arg | |
| 145 | | | | | 150 | | | | | 155 | | | | | 160 | |
| gga | gcg | ccc | ggg | ggc | ggc | ttc | gtc | ccc | agc | atg | caa | gga | gtc | ccg | gag | 528 |
| Gly | Ala | Pro | Gly | Gly | Gly | Phe | Val | Pro | Ser | Met | Gln | Gly | Val | Pro | Glu | |
| | | | | 165 | | | | | 170 | | | | | 175 | | |
| tcc | ccc | ttc | gct | cgg | acc | ggg | gag | gga | ctg | gac | ata | agg | gga | agc | cag | 576 |
| Ser | Pro | Phe | Ala | Arg | Thr | Gly | Glu | Gly | Leu | Asp | Ile | Arg | Gly | Ser | Gln | |
| | | | | 180 | | | | | 185 | | | | | 190 | | |

```
gga ttc cca tgg gat ata ctc t                                    598
Gly Phe Pro Trp Asp Ile Leu
        195
```

<210> SEQ ID NO 24
<211> LENGTH: 199
<212> TYPE: PRT
<213> ORGANISM: Hepatitis Delta Virus

<400> SEQUENCE: 24

```
Met Ser Arg Ser Glu Arg Arg Lys Asp Arg Gly Gly Arg Glu Asp Ile
1               5                   10                  15

Leu Glu Gln Trp Val Ser Gly Arg Lys Lys Leu Glu Glu Leu Glu Arg
            20                  25                  30

Asp Leu Arg Lys Leu Lys Lys Ile Lys Lys Leu Glu Glu Asp Asn
        35                  40                  45

Pro Trp Leu Gly Asn Ile Lys Gly Ile Ile Gly Lys Lys Asp Lys Asp
    50                  55                  60

Gly Glu Gly Ala Pro Pro Ala Lys Lys Leu Arg Met Asp Gln Met Glu
65                  70                  75                  80

Ile Asp Ala Gly Pro Arg Lys Arg Pro Leu Arg Gly Gly Phe Thr Asp
                85                  90                  95

Lys Glu Arg Gln Asp His Arg Arg Lys Ala Leu Glu Asn Lys Arg
            100                 105                 110

Lys Gln Leu Ser Ser Gly Gly Lys Ser Leu Ser Arg Glu Glu Glu Glu
        115                 120                 125

Glu Leu Lys Arg Leu Thr Glu Glu Asp Glu Lys Arg Glu Arg Arg Ile
    130                 135                 140

Ala Gly Pro Ser Val Gly Val Asn Pro Leu Glu Gly Gly Ser Arg
145                 150                 155                 160

Gly Ala Pro Gly Gly Gly Phe Val Pro Ser Met Gln Gly Val Pro Glu
                165                 170                 175

Ser Pro Phe Ala Arg Thr Gly Glu Gly Leu Asp Ile Arg Gly Ser Gln
            180                 185                 190

Gly Phe Pro Trp Asp Ile Leu
        195
```

<210> SEQ ID NO 25
<211> LENGTH: 195
<212> TYPE: PRT
<213> ORGANISM: Hepatitis Delta Virus

<400> SEQUENCE: 25

```
Met Ser Arg Ser Glu Arg Arg Lys Asp Arg Gly Gly Arg Glu Asp Ile
1               5                   10                  15

Leu Glu Gln Trp Val Ser Gly Arg Lys Lys Leu Glu Glu Leu Glu Arg
            20                  25                  30

Asp Leu Arg Lys Leu Lys Lys Ile Lys Lys Leu Glu Glu Asp Asn
        35                  40                  45

Pro Trp Leu Gly Asn Ile Lys Gly Ile Ile Gly Lys Lys Asp Lys Asp
    50                  55                  60

Gly Glu Gly Ala Pro Pro Ala Lys Lys Leu Arg Met Asp Gln Met Glu
65                  70                  75                  80

Ile Asp Ala Gly Pro Arg Lys Arg Pro Leu Arg Gly Gly Phe Thr Asp
                85                  90                  95

Lys Glu Arg Gln Asp His Arg Arg Arg Lys Ala Leu Glu Asn Lys Arg
            100                 105                 110
```

```
Lys Gln Leu Ser Ser Gly Gly Lys Ser Leu Ser Arg Glu Glu Glu Glu
        115                 120                 125

Glu Leu Lys Arg Leu Thr Glu Glu Asp Glu Lys Arg Glu Arg Arg Ile
    130                 135                 140

Ala Gly Pro Ser Val Gly Val Asn Pro Leu Glu Gly Gly Ser Arg
145                 150                 155                 160

Gly Ala Pro Gly Gly Phe Val Pro Ser Met Gln Gly Val Pro Glu
                165                 170                 175

Ser Pro Phe Ala Arg Thr Gly Glu Gly Leu Asp Ile Arg Gly Ser Gln
            180                 185                 190

Gly Phe Pro
        195

<210> SEQ ID NO 26
<211> LENGTH: 93
<212> TYPE: DNA
<213> ORGANISM: Artificial Sequence
<220> FEATURE:
<223> OTHER INFORMATION: PCR Primer

<400> SEQUENCE: 26
gggcatatga gccgtagcga acgtcgtaaa gatcgtggcg gccgtgaaga tattctggaa      60
cagtgggtga gcggccgtaa gaagttagag gaa                                  93

<210> SEQ ID NO 27
<211> LENGTH: 95
<212> TYPE: DNA
<213> ORGANISM: Artificial Sequence
<220> FEATURE:
<223> OTHER INFORMATION: PCR Primer

<400> SEQUENCE: 27 atattacccca accacgggtt atcttcttcc agtttcttaa tcttcttttt cagtttacgc      60
agatcacgtt ccaattcctc taacttctta cggcc                                 95

<210> SEQ ID NO 28
<211> LENGTH: 94
<212> TYPE: DNA
<213> ORGANISM: Artificial Sequence
<220> FEATURE:
<223> OTHER INFORMATION: PCR Primer

<400> SEQUENCE: 28
taacccgtgg ttgggtaata ttaaaggcat tattggcaag aaagataaag atggcgaagg      60
cgcgccgccg gcgaagaaac tgcgtatgga tcag                                 94

<210> SEQ ID NO 29
<211> LENGTH: 94
<212> TYPE: DNA
<213> ORGANISM: Artificial Sequence
<220> FEATURE:
<223> OTHER INFORMATION: PCR Primer

<400> SEQUENCE: 29
gatggtcctg acgttcctta tcggtaaagc cgccacgcag cggacgttta cgcgggcccg      60
catcaatttc catctgatcc atacgcagtt tctt                                 94

<210> SEQ ID NO 30
<211> LENGTH: 93
<212> TYPE: DNA
```

```
<213> ORGANISM: Artificial Sequence
<220> FEATURE:
<223> OTHER INFORMATION: PCR Primer

<400> SEQUENCE: 30
ataaggaacg tcaggaccat cgtcgtcgta aagcgctgga aaacaaacgt aaacagctga      60
gcagcggcgg caaatctctg agccgtgaag aag                                  93

<210> SEQ ID NO 31
<211> LENGTH: 89
<212> TYPE: DNA
<213> ORGANISM: Artificial Sequence
<220> FEATURE:
<223> OTHER INFORMATION: PCR Primer

<400> SEQUENCE: 31
caacagatgg acctgcaata cgacgttcac gtttttcatc ttcttcggtc agacgtttca      60
gttcttcttc ttcttcacgg ctcagagat                                       89

<210> SEQ ID NO 32
<211> LENGTH: 101
<212> TYPE: DNA
<213> ORGANISM: Artificial Sequence
<220> FEATURE:
<223> OTHER INFORMATION: PCR Primer

<400> SEQUENCE: 32
tattgcaggt ccatctgttg gtggtgtgaa cccgctggaa ggcggcagcc gtggcgcgcc      60
gggcggcggc tttgtgccgt ctatgcaagg tgttccagaa a                         101

<210> SEQ ID NO 33
<211> LENGTH: 90
<212> TYPE: DNA
<213> ORGANISM: Artificial Sequence
<220> FEATURE:
<223> OTHER INFORMATION: PCR Primer

<400> SEQUENCE: 33
gcgccatggt ttacggaaag ccctggctgc cacgaatatc caggccttcg ccggtacgcg      60
caaacgggct ttctggaaca ccttgcatag                                      90

<210> SEQ ID NO 34
<211> LENGTH: 20
<212> TYPE: DNA
<213> ORGANISM: Artificial Sequence
<220> FEATURE:
<223> OTHER INFORMATION: PCR Primer

<400> SEQUENCE: 34
gggcatatga gccgtagcga                                                 20

<210> SEQ ID NO 35
<211> LENGTH: 20
<212> TYPE: DNA
<213> ORGANISM: Artificial Sequence
<220> FEATURE:
<223> OTHER INFORMATION: PCR Primer

<400> SEQUENCE: 35
gcgccatggt ttacggaaag                                                 20
```

OLIGOMERIZATION OF HEPATITIS DELTA ANTIGEN

RELATED APPLICATIONS

This application claims priority to U.S. Provisional Application No. 60/091,609 filed Jul. 2, 1998, the contents of which are incorporated herein by reference in their entirety.

GOVERNMENT SUPPORT

The invention was made with Government support from the National Institutes of Health under grant AI32480 and R01-HL37974 and the U.S. Public Health Service (GM42031) and the Giovanni Armorisse Harvard Center for Structural Biology. The Government has certain rights in the invention.

BACKGROUND OF THE INVENTION

The hepatitis D virus (HDV) is a small satellite virus of hepatitis B virus (HBV). Coinfection with HBV and HDV causes severe and sometimes fatal liver disease in humans. The HDV genome encodes a single known protein, the hepatitis delta antigen (HDAg).

SUMMARY OF THE INVENTION

This invention is based on the discovery of the high resolution crystal structure of a synthetic peptide corresponding to residues 12–60 of the hepatitis delta antigen (HDAg). This peptide includes a coiled-coil region believed to be important for dimerization of HDAg. The peptide forms an antiparallel coiled coil with hydrophobic residues near the termini of each peptide forming an extensive hydrophobic core with residues C-terminal to the coiled-coil domain in the dimer protein. The crystal structure shows how HDAg forms dimers, but, surprisingly, also shows the dimers forming an octameric structure that forms a large 50 Å ring lined with basic sidechains.

The dimers associate further to form octamers through residues in the coiled-coil domain that are not involved in a heptad repeat, as well as through residues C-terminal to this region. The crystal structure of the peptide and cross-linking hydrodynamic studies which show that the full-length recombinant protein also forms octamers suggest that the structure of the delta antigen represents a previously unseen organization of a viral nucleocapsid protein. This N-terminal octamer can serve as a convenient high-valency framework for linking a variety of functional peptides and domains.

The invention includes HDAg proteins, including derivatives, mutants and fragments, and nucleic acid molecules encoding HDAg. Derivatives of HDAg protein include fusion molecules. In one embodiment, the fusion molecule comprises HDAg and at least one binding moiety bound, for example, to the HDAg through the C terminus, N terminus and/or other amino acid. The binding moiety can be selected from the group consisting of an antigen, an antibody, a ligand, a receptor, an enzyme, a ligand interaction peptide, a chemical, an effector, an oligonucleotide, a signal amplification peptide, an enhancer recognition protein, a promoter binding protein, a label, a growth factor, a cytokine, a nuclease, a small organic molecule, a test substance, a cytotoxic agent, a substrate, a solid substrate, a drug, or a fragment thereof. The fusion molecules of the invention can also comprise two binding moieties which are binding partners. The fusion molecule can be a fusion protein. The HDAg and the binding moiety can be chemically linked or the HDAg and the binding moiety can be expressed as a single unit.

The invention also relates to coiled-coil oligomers comprising at least two such fusion molecules. The coiled-coil oligomer can be an octamer. In the coiled-coil oligomer, the two fusion molecules can be the same or different.

The invention also relates to nucleic acid molecules. For example, a nucleic acid molecule can comprise a nucleotide sequence depicted in FIG. 9 (SEQ ID NO:10), nucleotides 37–150 of FIG. 9 (nucleotides 37–150 of SEQ ID NO:10), nucleotides 37–186 of FIG. 9 (nucleotides 37–186 of SEQ ID NO:10), FIG. 10 (SEQ ID NOS:12–14), nucleotides 1421–1566 of FIG. 10 (nucleotides 1421–1566 of SEQ ID NOS:12–13), nucleotides 1457–1566 of FIG. 10 (nucleotides 1457–1566 of SEQ ID NOS:12–13), FIG. 15 (SEQ ID NOS:21 and 23) or FIG. 16 (SEQ ID NO:10). The nucleic acid molecule can also comprise a nucleotide sequence which encodes a polypeptide comprising an amino acid sequence depicted in a row of FIG. 1 (SEQ ID NOS:1–8), amino acids 12–48 of a row of FIG. 1 (amino acids 12–48 of SEQ ID NOS:1–8), the top row of FIG. 3C (SEQ ID NO:9), FIG. 9 (SEQ ID NO:11), amino acids 12–48 of a row of FIG. 9 (amino acids 12–48 of SEQ ID NO:11), FIG. 10 (SEQ ID NOS:15–17), amino acids 12–88 of FIG. 10 (amino acids 12–88 of SEQ ID NOS:15–17), FIG. 11B (SEQ ID NOS:18–20) or FIG. 17 (SEQ ID NO:25). Also included are complementary strands of these sequences, DNA sequences that hybridize to the sequences, RNA sequences transcribed from the sequences, or a fragment or mutation thereof, which encodes a coiled-coil oligomer.

An isolated nucleic acid molecule can be a fusion molecule described herein. The invention also includes fusion genes comprising an HDAg nucleic acid molecule operably linked to a nucleic acid molecule encoding a heterologous (non-HDAg) peptide.

Also encompassed in the scope of the invention are isolated, purified and/or recombinant peptides and molecules comprising peptides. In one embodiment, a polypeptide comprises an amino acid sequence encoded by an HDAg nucleic acid molecule. The molecules can comprise a polypeptide having an amino acid sequence selected from the group consisting of an amino acid sequence depicted in a row of FIG. 1 (SEQ ID NOS:1–8), amino acids 12–48 of a row of FIG. 1 (amino acids 12–48 of SEQ ID NOS:1–8), amino acids 12–60 of a row of FIG. 1 (amino acids 12–60 of SEQ ID NOS:1–8), the top row of FIG. 3C (SEQ ID NO:9), FIG. 9 (SEQ ID NO:11), amino acids 12–48 of FIG. 9 (amino acids 12–48 of SEQ ID NO:11), amino acids 12–60 of FIG. 9 (amino acids 12–60 of SEQ ID NO:11), FIG. 10 (SEQ ID NOS:15–17), FIG. 11B (SEQ ID NOS:18–20) and FIG. 17 (SEQ ID NO:25), or a fragment or derivative thereof which forms a coiled-coil oligomer. The peptide can be a derivative peptide wherein a serine residue is substituted with cysteine. The molecules can comprise a polypeptide comprising an amino acid sequence of amino acids 12–88 of HDAg, or a fragment or derivative thereof which forms a coiled-coil oligomer and nuclear localization signal. The polypeptides can be encoded by fusion genes comprising HDAg. It is possible that the molecule can be larger than the 12–48 or 12–60 or 12–88 amino acids, for example. It may be desirable to make a 12–65 or 10–93 peptide, for example.

The invention also includes vectors which can express HDAg. The vectors can comprise a nucleic acid molecule which encodes a subunit of an HDAg coiled-coil octamer. The nucleic acid molecule can comprise a sequence listed above. The nucleic acid molecule can encode a fusion molecule. The vector can be a nucleic acid molecule encoding HDAg and at least one multiple cloning site. The multiple cloning site(s) can be located 3' to the nucleic acid molecule encoding HDAg or 5' to the nucleic acid molecule encoding HDAg. There can be two or more multiple coding sites, wherein at least one multiple coding site is located in a flanking region 3' to the nucleic acid molecular encoding HDAg and/or at least one multiple coding site is located in a flanking region 5' to the nucleic acid molecule encoding HDAg. The vector can further comprise a nucleic acid molecule encoding a nuclear localization signal. A vector can further comprise a nucleic acid molecule which encodes a heterologous gene. The vector can express a fusion molecule of HDAg wherein a first heterologous gene encodes a first binding moiety and a second heterologous gene encodes a second binding moiety.

The invention also encompasses host cells which comprise a nucleic acid molecule which encodes a molecule of HDAg, including a fusion molecule.

The invention also includes methods of manufacturing such a host cell comprising a nucleic acid molecule encoding a fusion molecule comprising HDAg and at least one binding moiety, by introducing a vector of the invention into the host cell.

The invention also relates to methods of using the molecules, i.e., peptides, nucleic acids, and vectors of the invention. One method comprises expressing a high valency display of at least one binding moiety comprising introducing into a cell with a vector comprising a nucleic acid molecule encoding HDAg and a nucleic acid molecule encoding the binding entity and culturing the cell under conditions sufficient to permit expression of the binding moiety and HDAg.

The invention also encompasses a method of enhancing interaction between binding partners comprising contacting a fusion molecule of HDAg with a second binding moiety wherein the first and second moieties are binding partners. The fusion molecule can present the first and second moieties. The interaction between ligands can occur in solution, on membranes or on surfaces. The fusion molecule can be a subunit of a coiled-coil oligomer, e.g., an octamer, and the first and second moieties are bound to the oligomer. In one embodiment, fusion of a first cell and a second cell is enhanced.

The invention also includes a method for delivering molecules to a cell comprising contacting them with an HDAg fusion molecule. In one embodiment, the binding moiety is an oligonucleotide. The oligonucleotide can hybridize to a nucleic acid molecule in the cell. The fusion molecule can further comprise a double-stranded nuclease. In one embodiment, the fusion molecule comprises a first binding moiety and a second binding moiety wherein the first binding moiety interacts with a binding partner and the second binding moiety functions as an effector. The first binding moiety can interact with a cell surface receptor on a cell and the second binding moiety can kill the cell.

The invention also includes a method of amplifying a signal in a solid phase assay comprising coupling an HDAg octamer with at least one copy of a domain which interacts with a ligand and at least two copies of a label. The label can be, for example, alkaline phosphatase, a radiolabel, streptadavin, and green fluorescent protein. In one embodiment, the solid phase assay is an ELISA assay. The invention also encompasses a method of facilitating exchange of substrates and products comprising coupling an HDAg oligomer to at least two enzymes which function in a linked pathway.

The invention also encompasses a method of enhancing a reaction between at least two binding partners comprising coupling the binding partners to an HDAg oligomer. In a different embodiment, the method of enhancing a reaction between two binding partners comprises coupling one binding partner to an HDAg oligomer and contacting the oligomer to a second binding partner.

BRIEF DESCRIPTION OF THE DRAWINGS

FIG. 1 depicts sequence alignment of 11 serotypes of hepatitis delta antigen (HDAg) between amino acids 12 to 60 (SEQ ID NOS:1–8). Asterisks, *, indicate residues which make up the a and d positions in the heptad repeat in the predicted coiled-coil region. Bold pink and purple indicate residues involved in the hydrophobic interactions in the dimer between the two termini. The "ds" indicate residues involved in the dimer-dimer interface. A region (pink), B (green), C (purple).

FIG. 2 depicts the final atomic model superimposed upon a portion of the final 1.8 Å resolution $2F_o$-$F_c$ map. The map is contoured at 1.2σ and shows the residues involved in the interaction between monomers at the A and C regions. Orientation is similar to that in FIG. 4. Yellow indicates carbon, red indicates oxygen and blue indicates nitrogen. The figure was produced using BOBSCRIPT.

FIG. 3A depicts Cα trace of the peptide δ12–60(Y). A region pink, B region green, and C region purple. The individual helix takes a sharp bend at proline 49 (Pro49). FIG. 3B is a ribbon diagram of the view in FIG. 3A rotated 90° along the horizontal axis. The sidechains have been added and the C region of the peptide (residues 50–60(Y)) has been removed for clarity. Sidechains are colored as follows: hydrophobic gray, polar yellow, acidic red and basic blue. FIG. 3C (SEQ ID NO:9) is the amino acid sequence of the long helix formed from residues 12 to 48 displayed in the antiparallel orientation of the peptide. The letters above the amino acid sequence represent the heptad repeat (abcdefg)n where the a and d residues tend to be hydrophobic. The residues involved in the heptad repeat at the a and d positions are shown in bold.

FIG. 4 depicts the monomer-monomer interactions. The regions are colored as follows: A region pink, B region green, and C region purple. The white row of X's indicates a hydrogen bond between the sidechain of Glu45 (E45) and the indole nitrogen of Trp20 (W20). This figure was produced using RIBBONS, Carson, M. & Bugg, C. E., *J. Mol. Graphics*, 4:121–122 (1986).

FIG. 5 depicts the interactions of dimers in the $P2_12_12$ unit cell. The unit cell is outlined in black and the directions of the A and B axes are shown. The two independent copies of the dimer in the asymmetric unit are colored orange and blue. The view is looking down the crystallographic 2-fold axis. This figure was produced using the program MOLSCRIPT (Kraulis, P. J. *J. Appl. Cryst*. 24:946–950 (1991)).

FIG. 6 depicts the dimer-dimer interface. FIG. 6A illustrates that the dimer-dimer interface is composed of a four-helix bundle made of the N and C termini of two dimers, one from across the crystallographic two-fold axis. One (unlabeled) dimer is colored yellow and the other (labeled) dimer is colored according to the scheme used in FIG. 1. FIG. 6B depicts the view in FIG. 6A rotated 90° around the y axis. This figure was created with RIBBONS (Carson, M. & Bugg, C. E., *J. Mol. Graph*. 4:121–122 (1986)).

FIG. 7A is a GRASP electrostatic potential surface of the octameric σ12–60(Y) peptide contoured at=10 kT/e (positive potential blue) and10 K/e (negative potential in red)(K is Boltzman's constant and T is temp ° K. The edges and the lining of the large 50 Å hole are basic. FIG. 7B illustrates the hole formed by the octamer.

FIG. 8 graphically illustrates MALDI-TOF mass spectrometry analysis of recombinant small delta antigen (r-HDAg-S)(FIG. 8A), and the glutaraldehyde cross-linked protein (FIG. 8B).

FIG 9 (SEQ ID NOS:10 and 11) depicts the sequence of a synthetic gene for optimized expression of HDAg-S in E.coli. The synthetic gene (SEQ ID NO:10) has been modified such that the codon usage which is unusual in the natural gene is assistant with the known preferences for codon usage in E. coli. The underlined sequences correspond to the eight primers used in the first round of PCR. The primers used in the second round are indicated with a dotted underline. The amino acid sequence (SEQ ID NO:11) is shown above the DNA sequence by the one-letter amino acid code. The restriction sites used in cloning are shown in italics.

FIG. 10 (SEQ ID NOS:12 –17) depicts the complete sequence of human HDV cDNA (SEQ ID NO:13), and the predicted amino-acid sequence (SEQ ID NO:15) of human HDV delta antigen.

FIG. 11 depicts synthetic peptides from the multimer-forming domain of HDAg. (A) Structural organization of HDAg. The lightly stippled region is the multimer-forming domain (amino acid residues 12–60)(SEQ ID NO:1), the solid regions are the RNA-binding domains, and the heavily stippled region is the C-terminal extension of large HDAg. Hydrophobic residues contributing to the heptad repeat are shown in boldface type, (B) Amino acid sequences of three HDAg peptides (SEQ ID NOS:18–20).

FIG. 12 depicts use of the delta antigen as a scaffold. A construct containing eight appended protein domains on the octameric framework. FIG. 12A depicts an oligomerization domain and spheres which represent potential effectors/ligands/nucleic acid binding domains etc. that have been fused to the C-terminus of the oligomerization domain of the delta antigen. FIG. 12B depicts binding domain which is a multimer, specifically a tetramer. A similar fusion of up to eight effector/legands/nucleic acid binding domains could be made at the N-terminus, and constructs with fusion domains at up to eight N-termini and up to eight C-termini could also be made.

FIG. 13 depicts plasmids comprising HDAg for expression in bacteria. "DAg" refers to a delta antigen sequence (with or without nuclear localization sequence); "MCS1" refers to a multiple cloning site for insertion of a heterologous gene at N-terminal end of delta antigen; "MCS2" refers to a multiple cloning site for insertion of a heterologous gene a C-terminal end of delta antigen; "Ori" refers to the origin of replication for the bacteria; "drug" refers to a drug marker; "fl ori" refers to origin of replication of single-stranded DNA by a bacteriophage; "promoter" refers to bacterial promoter. FIG. 13A depicts MCS1 3' to HDAg; FIG. 13B depicts MCS1 5' to HDAg; and FIG. 13C depicts MCS1 3' and MCS2 5' to HDAg.

FIG. 14 depicts a plasmid comprising HDAg for expression in eukaryotic cells. "DAg refers to a delta antigen sequence (with or without nuclear localization sequence). "MCS1" refers to plasmids comprising replication of plasma in bacteria; "Ori" refers to origin of expression or replication of the plasmid in bacterial cells; "drug1" refers to a drug marker (e.g. ampicillin, kanamycin) for propagation of plasmid in E. coli, "drug2" refers to a drug marker or eukaryotic drug resistance (e.g. neomycin, zeocin, hybromycin), for propagation of plasmid in a eukaryotic cell; "fl ori" refers to origin of replication of single-stranded DNA by bacteriophage; "promoter" refers to eukaryotic promoter.

FIG. 15 (SEQ ID NOS:21–24) is a comparison of the wildtype nucleotide sequence of HDAg-S (SEQ ID NO:23) and the sequence of the synthetic HDAg gene for optimized expression in E. coli (SEQ ID NO:21).

FIG. 16 is the nucleotide sequence of the synthetic open reading frame (ORF) for the synthetic HDAg (SEQ ID NO:10).

FIG. 17 is a comparison of the protein amino acid sequence (SEQ ID NO:25) encoded by the wildtype ORF and the synthetic ORF, showing complete (100%) identity.

FIG. 18 depicts the nucleotide sequences of the primers used for the two polymerase chain reactions (PCR) to create the synthetic gene. Primer1–primer8 (SEQ ID NOS:26–33) were used in the first round of PCR and primer9 –primer10 (SEQ ID NOS:34–35) were used in the second round of PCR.

DETAILED DESCRIPTION OF THE INVENTION

Figure 3A:
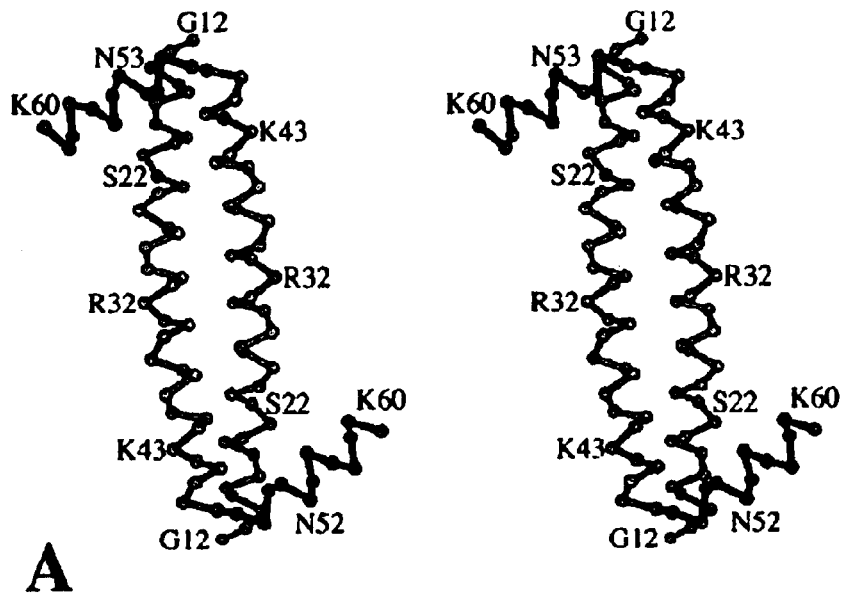

As set forth above, the present invention relates to the discovery of the oligomeric structure of the hepatitis delta antigen (HDAg) which serves as a convenient high-valency framework for linking a variety of binding partners, including functional peptides and domains. The structure of the antigen includes a doughnut-shaped octamer comprising N-terminal antiparallel coiled-coil domains and stabilizing C-terminal domains. The invention includes HDAg proteins, including derivatives, mutants and fragments, and nucleic acid molecules encoding HDAg. It also includes an altered HDAg gene for the capsid protein wherein the codons conform to use preferences for E. coli. Included in the derivatives are fusion molecules, e.g., fusion proteins, in which one or more binding moieties are attached to one or both termini of a monomer and coiled-coil oligomers (e.g., octamers) formed from the monomers. Coiled-coil oligomers of the present invention can comprise one or more fusion molecules as described herein. The binding moieties can be, for example the same (homologous) or different (heterologous) binding partners. The invention also includes vectors and cassette expression systems which can be used to produce the fusion molecules. The vectors comprise HDAg and one or more binding moieties which are operably linked to HDAg. The invention also relates to cells comprising HDAg nucleic acid, e.g. cells transformed with such vectors, and to methods of producing such cells. The invention also includes therapeutic and diagnostic methods involving HDAg.

HDAg Peptides

HDAg, as defined herein, includes both the large and small delta antigens (HDAg-S and HDAg-L). HDAg encompasses native ("wild type") proteins and also includes derivatives, mutations, and functional protein or polypeptide fragments of the native protein and/or proteins or polypeptides where one or more amino acids have been deleted, added or substituted.

HDAg can be isolated and/or purified, or it can be recombinant or prepared by synthetic techniques described herein or known to those of skill in the art. HDAg proteins or fragments can be isolated from the cell of origin or produced synthetically or recombinantly. In a preferred embodiment, the protein is isolated to the substantial absence of conspecific proteins. A conspecific protein is a protein other than HDAg which can be obtained from the cell of origin for the protein or its nucleic acid. The proteins (and nucleic acids) described herein can be preferably isolated, by known methods, to a purity of at least about 50% by weight, more preferably at least about 75% and most preferably to substantial homogeneity. "Substantial homogeneity" refers to the substantial absence of conspecific proteins.

An HDAg peptide can, e.g., include all or a portion of the amino acids depicted in FIGS. 1, 3C, 10, 11B or 17 (SEQ ID NOS:1–8, 9, 15–17, 18–20 and 25). An HDAg peptide can be encoded by an isolated and/or purified or recombinant nucleic acid molecule or a fusion gene (nucleic acid molecule) such as those described herein. In a preferred embodiment, an isolated and purified polypeptide has an amino acid sequence depicted in a row of FIG. 1 (SEQ ID NOS:1–8), amino acids 12–48 of a row of FIG. 1 (amino acids 12–48 of SEQ ID NOS:1–8), amino acids 12–60 of a row of FIG. 1 (amino acids 12–60 of SEQ ID NOS:1–8), a row of FIG. 3C (SEQ ID NO:9), FIG. 9 (SEQ ID NO:11), amino acids 12–48 of FIG. 9 (amino acids 12–48 of SEQ ID NO:11), amino acids 12–60 of FIG. 9 (amino acids 12–60 of SEQ ID NO:11), FIG. 10 (SEQ ID NOS:15–17), FIG. 11B (SEQ ID NOS:18–20), FIG. 17 (SEQ ID NO:25) or a fragment or derivative thereof, which forms a coiled-coil oligomer.

In another embodiment, an isolated and purified polypeptide has the amino acid sequence of amino acids 12–88 of HDAg, or a fragment or derivative thereof, which forms a coiled-coil oligomer and nuclear localization signal.

"Homology" is defined herein as sequence identity. Preferably, the protein or polypeptide shares at least about 50 % sequence identity or homology and more preferably at least about 75 % identify or at least about 90% identity with the corresponding sequences of the native protein, for example, with FIG. 10 (SEQ D NOS:15–17). The phrase "substantially the same sequence" is intended to include sequences which bind the viral protein and possess a high percentage of (e.g., at least 90%, preferably at least about 95%) amino acid sequence identity with the native sequence. For example, a derivative, e.g., a mutant or variant can possess substantially the same amino acid sequence as the native protein.

The modifications to the amino acid sequence (substitutions) can be conserved or non-conserved, natural or unnatural amino acids. The residues that function to form or stabilize the coiled-coil domain or binding sites thereof can be substituted, e.g., conservatively, or they can be maintained. Amino acids of the native sequence for substitution, deletion or conservation can be identified, for example, by a sequence alignment between proteins from different serotypes from related species or other related proteins. In one embodiment, the amino acids which are deleted, added or substituted are amino acids which are not "conserved" between serotypes or species, for example, the amino acids so identified in the sequence alignment exemplified in FIG. 1 (SEQ ID NOS:1–8). Conserved amino acids may also be substituted. In one embodiment they are substituted conservatively, for example, substituted by structurally similar amino acids. The phrase "conservative amino acids substitutions" is intended to mean substitutions of amino acids which possess similar side chains (e.g., hydrophobic, hydrophilic, basic acidic, aromatic, and aliphatic) as is known in the art. See, for example, Hermanson, G. I. Bioconjjugate Techniques, Academic Press, Inc. San Diego, Calif.(1996). Conservative substitutions include amino acid substitutions of one hydrophobic amino acid for another, for example within the following grouping: W, F, A, P, L, M, I, V. Acidic amino acids include E and D; basic amino acids include K, R, and H. Polar amino acids include S, T, N, Q and G and amide residues include Q and N. An example of a suitable derivative or mutant of the HDAg protein is a protein possessing a consensus sequence of the originating species.

In one embodiment, the derivative does not contain substitutes of the residues of Arg13, Leu17, Trp20 , Arg24, Trp50 or Leu51. In another embodiment, it contains only conservative substitutions in this region. Hydrophobic residues, for example Ile16, Leu17, Trp20 , Trp50 and Leu51 can be maintained, or they can be replaced with other hydrophobic amino acids, for example, those from the group consisting of Trp, Phe, Ala, Pro, Leu, Met, Ile and Val. In another example, the residues Glu31, Lys38, Trp20 and Glu45 are not substituted or are substituted conservatively. In addition, Arg13 and Arg24 can be maintained (not substituted) or substituted conservatively. In another embodiment, the residues of FIG. 1 (SEQ ED NOS:1–8) which are involved in hydrophobic interactions are substituted with other hydrophobic residues. In FIG. 3A, hydrophobic residues can be substituted for other hydrophobic residues, polar residues can be substituted for other polar residues, acidic residues can be substituted for other acidic residues, and/or basic residues for other basic residues. In one example, the residues labeled in FIG. 3A can be maintained (not substituted) or can be replaced with amino acids with similar characteristics. The amino acids at the 'a' and 'd' positions of the heptad repeat (for example, those indicated with an asterisk in FIG. 1 (SEQ ID NOS:1–8) or those listed in bold in FIG. 3C (SEQ ID NO:9), can be conserved (maintained), or they can be substituted conservatively, e.g., replaced with hydrophobic amino acids. The residues involved with the dimer-dimer interface (e.g., residues marked with a 'd' in FIG. 1 (SEQ ID NOS:1–8) or residues labeled in FIG. 6) can be maintained. The residues indicated in FIG. 4 can be maintained. The derivatives, e.g. mutant and wild-type peptides, can crystallize isoniorphously. In one preferred embodiment, at least one serine residue, e.g., Ser22, is replaced with a cysteine. In another embodiment, Trp20 is replaced with Ala20.

A variety of substitutions based on amino acid characteristics can be made. For example, the polar amino acid residues can be substituted and the hydrophobic amino acids can be maintained. In addition the nonhydrophobic residues can be substituted and the hydrophobic residues can be maintained. In one embodiment, a derivative can comprise substitutions of any or all of the amino acid residues in the following positions: 14, 15, 18, 19, 22, 24, 25, 26, 28, 29, 31, 32, 33, 35, 36, 38, 39, 40, 42, 43, 45, 46 and 47. The nonhydrophobic residues can be substituted such that acidic amino acids are alternated with basic amino acids. The hydrophilic residues in the C terminal region can be substituted to optimize stability of the helix, for example by presenting one or more amino acids which form disulfide bonds, strong ionic bonds or cross-linked moieties, with the corresponding amino acid of another subunit. In one embodiment, residues 53, 55 and 60 are substituted.

Especially preferred are derivatives, e.g., coiled-coil subunits, which improve (e.g., optimize) stability of the coiled-coil structure or which improve cross-linkage involving the structure, or which improve the ability of the structure to be immobilized on a solid substrate.

The term derivative is also intended to include proteins which have been labeled, such as with a radioactive or colorimetric label. Such derivatives are more readily detected in an assay. In one embodiment, a peptide is synthesized that corresponds to residues 12–60 of HDAg, and includes a C-terminal tyrosine, enabling the peptide to be labeled, e.g., with $I^{25}$, for use in a radioimmunoassay. In one embodiment, the peptide is δ12–60(Y). Yet other derivatives are proteins which consist essentially of the amino acid sequence of a given protein (e.g., possess the relevant sequence and, optionally, other amino acids residing at the termini which do not significantly alter or detract from the properties of the protein).

A "functional" fragment, derivative, mutant, or allelic variant is of sufficient length and/or structure as to possess one or more biological activities of the protein. One example of such a biological activity of the protein is formation of a coiled-coil oligomer, e.g., an octamer, for example, an octamer doughnut-shaped structure. In one embodiment, the protein derivative is conserved within the coiled-coil regions but is lacking in or mutated within one or more other regions (e.g., sequences not within the coiled-coil. Examples of suitable fragments include peptides lacking fragments which encode or stabilize the coiled coil, for example, amino acids 12–48, or the peptides depicted in FIG. 11B (SEQ ID NOS:18–20). One example includes fragments which lack all or part of the region C-terminal to the proline bend (e.g. C-Terminal to Pro49). Another fragment includes the coiled coil and nuclear localization signal (e.g., amino acids 12–88); or solely the nuclear localization signal (amino acids 68–88). Xia et al., J. Virol. 66:914–21 (1992). Yet another example includes HDAg which encodes the coiled-coil region but is lacking all or a portion of the nuclear localization signal. In one embodiment, all or a portion of one or both termini of a monomer is absent or mutated. For example, the C region of the peptide (e.g., residues 50–60) can be mutated or all or a portion can be eliminated. Yet another example of derivatives includes peptides which possess amino acid modifications or additions which are characterized by a functional group which can react with a compound substituted by a "binding moiety", such as those described above or with a cross-linking agent.

Yet other biologically activities are the ability of HDAg-S to function as a trans activator of replication and the ability of HDAg-L to act as an inhibitor of replication. In yet another embodiment, the biological activity of the protein is antigenic or immunogenic activity.

Fragments of the protein can possess at least about 10 amino acids from the 12–48 amino acid region, preferably at least about 20 amino acids. In other embodiments, the fragment possesses essentially all of the amino acids of the full-length protein (e.g., at least about 85%, or at least about 95%).

HDAg includes monomers and oligomers, e.g., dimers and octamers, comprising the monomers as subunits. The invention encompasses HDAg coiled-coil oligomers, e.g. octamers.

Fusion Molecules

Fusion molecules are intended to be included within the definition of HDAg derivatives and can be made by linking one or more binding moieties, e.g., chemicals or peptides, to the HDAg protein or fragment, for example, through a covalent bond or preferably a peptide bond or cysteine group. As such, derivatives, such as fusion proteins, can comprise the amino acid sequence of the HDAg protein or fragment and a binding moeity such as a given protein, e.g., a native protein.

A "binding moiety," as the term is defined herein, includes a chemical entity which is bound to HDAg. The binding can be via a covalent bond (e.g. through a cysteine group), ionic bonding, hydrogen bonding or other mechanism. The binding moiety and the HDAg can be expressed as a single unit. The binding moiety can be a peptide (including post-translationally modified proteins, such as amidated, demethylated, glycosylated or phosphorylated proteins), sugar, lipid, steroid, nucleic acid, small molecule, anion or cation, drug, chemical or combination thereof which binds the specified binding partner (e.g., a target molecule). Preferably, the binding will possess a high affinity. Examples of high affinity can have a dissociation constant of $10^{-5}$M (preferably $10^{-8}$M) or lower. Examples of binding moieties include an antigen, an antibody, a ligand, a receptor, an enzyme, a (ligand) interaction peptide, a chemical, an effector, an oligonucleotide, a signal amplification peptide, an enhancer recognition protein, a promoter binding protein, a label, a growth factor, a cytokine, a nuclease, a small organic molecule, a test substance, a cytotoxic agent, a substrate, a solid substrate, a drug or a fragment thereof.

Where there are two or more binding moieties, the binding moieties can be the same (homologous) or different (heterologous). The binding moieties can be binding partners. Examples of binding partners include, but are not limited to, antigen-antibody and ligand-receptor. First and second binding moieties can also include the following pairs: enzyme1–enzyme2, (ligand) interaction peptide-effector peptide (or chemical), oligonucleotide-nuclease, interaction agent (e.g. peptide signal amplification agent, (e.g. peptide), enhancer recognition agent (e.g. protein)-promoter-binding agent (e.g. protein), enhancer recognition agent-promoter binding agent, ligand-label, test substance-label, targeting agent—effector agent, drug (or hormone)—label, or any other combination.

In one embodiment, a first binding moiety binds, a target molecule on a target cell (e.g. a surface protein) and the binding partner is the surface protein or target cell. The "target cell" is defined as the cell which is intended to be contacted by the fusion cell. Typically, the target cell is of animal origin and can be a stem cell or somatic cell. Suitable animal cells for use on the claimed invention can be of, for example, mammalian and avian origin. Examples of mammalian cells include human, bovine, ovine, porcine, murine, rabbit cells. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

Typically, cells isolated from a specific tissue (such as epithelium, fibroblast or hematopoietic cells) are categorized as a "cell-type." The cells can be obtained commercially or from a depository or obtained directly from an animal, such as by biopsy. Alternatively, the cell need not be isolated at all from the animal where, for example, it is desirable to deliver the vector to the animal in gene therapy.

Cells can typically be characterized by markers expressed at their surface that are termed "surface markers". These surface markers include surface proteins or target molecules, such as cellular receptors, adhesion molecules, transporter proteins, components of the extracellular matrix and the like. These markers, proteins and molecules also include specific carbohydrates and/or lipid moieties, for example, conjugated to proteins. In one embodiment, a binding moiety on a fusion molecule can bind to one or more surface proteins on the target cell. Surface proteins can be tissue- or cell-type specific (e.g. as in surface markers) or can be found on the surface of many cells. Typically, the surface marker, protein or molecule is a transmembrane protein with one or more domains which extend to the exterior of the cell (e.g. the extracellular domain). Where cell-type specific delivery is desired (as in in vivo delivery of a drug), the surface protein selected for the invention is preferably specific to the tissue. By "specific" to the tissue, it is meant that the protein be present on the targeted cell-type but not present (or present at a significantly lower concentration) on a substantial number of other cell-types. While it can be desirable, and even preferred, to select a surface protein which is unique to the target cell, it is not required for the claimed invention. It is to be appreciated, however, that specific delivery may not be required where the cell or cells are contacted with the viral vector in pure or substantially pure form, such as can be the case in an in vitro gene transfer. As such, the surface protein or targeted protein for the first binding moiety may be present on many different cell-types, specific or even unique to the targeted cell-type.

As set forth above, the surface protein can be a cellular receptor or other protein, preferably a cellular receptor. Examples of cellular receptors include receptors for cytokines, growth factors, and include, in particular epidermal growth factor receptors, platelet derived growth factor receptors, interferon receptors, insulin receptors, proteins with seven transmembrane domains including chemokine receptors and frizzled related proteins (Wnt receptors), immunoglobulin-related proteins including MHC proteins, CD4, CD8, ICAM-1, etc., tumor necrosis factor-related proteins including the type I and type II TNF receptors, Fas, DR3, DR4, CAR1, etc., low density lipoprotein receptor, integrins, and, in some instances, the Fc receptor.

Other examples of surface proteins which can be used in the present invention include cell-bound tumor antigens. Many of these surface proteins are commercially available and/or have been characterized in the art, including the amino acid and nucleic acid sequences, which can be obtained from, for example, GENBANK, as well as the specific binding characteristics and domains. Cytokine and chemokine receptors are reviewed for example, in Miyama, et al. *Ann. Rev. Immunol.*, 10:295–331 (1992), Murphy, *Ann. Rev. Immunol.* 12:593–633 (1994) and Miller et al. *Critical Reviews in Immunol.* 12:17–46 (1992).

The binding moiety can be selected or derived from native ligands or binding partners to the surface protein of the target cell. In the case of a cellular receptor, for example, for a cytokine or growth factor, the binding moiety can be a polypeptide comprising at least the receptor-binding portion of the native ligand. A "native ligand" or "native binding partner" is defined herein as the molecule naturally produced by, for example, the animal or species which binds to the surface protein in nature. Preferably, the binding moiety is a polypeptide or protein. As such, the native ligand of a cytokine receptor can be the native cytokine. In another embodiment, the binding moiety can comprise a binding fragment of an antibody, such as the variable region or a single chain antibody.

Where a binding moiety comprises a binding fragment of an antibody, many antibodies to surface proteins are known or are commercially available, as are the amino acid sequences which are responsible for binding. Alternatively, novel antibodies can be prepared by methods known in the art, such as by Harlow and Lane, "Antibodies, A Laboratory Manual," Cold Spring Harbor Laboratory (1988). The binding fragment can comprise an antibody fragment, for example, the constant region or, the variable region (e.g., Fc fragment or FAb' fragment).

A binding moiety can be a polypeptide ligand to a cellular receptor. Examples of preferred ligands are growth factors, epidermal growth factor, interleukins, GM-CSF, G-CSF, M-CSF, EPO, TNF, interferons, and chemokines. In one embodiment, the receptor is a transferon receptor.

The binding moiety can have an amino acid sequence which is the same or substantially the same as an amino acid sequence of at least the receptor-binding portion of a native ligand for the cellular receptor. Similar to cellular receptors, many of the corresponding ligands have been identified, sequenced and characterized, including the portions thereof which bind to the receptor. The binding moiety can, therefore, include the same or substantially the same sequence of the entire native ligand. Alternatively, binding moiety comprises the receptor binding portion of the native ligand, eliminating, in some cases, the effector function of the ligand.

In another embodiment, the binding moiety is selected or derived from native ligands or binding partners to a cellular surface molecule of a target cell. A "cellular surface molecule" as defined herein can be a peptide (including post-translationally modified proteins, such as amidated, demethylated, methylated, prenylated, palmitoylated, glycosylated, myristylated, acetylated or phosphorylated proteins), sugar, lipid, steroid, anion or cation, or a combination thereof which binds the first binding moiety. Preferably, the binding of the cellular surface molecule to the binding moiety of the bifunctional molecule will be of high affinity. Examples of high affinity have a dissociation constant of $10^{-5}M$ (preferably $10^{-8}M$) or better.

The cellular surface molecule need not be "specific" for the target cell. However, the cellular surface molecule is specific for a desired viral vector. For example, specific delivery of Influenza A viral vectors can employ sialic acid cellular surface molecules for entry into a target cell whereas targeting of VSV viral vectors can employ a phospholipid as the surface molecule. As such, the cellular surface molecule for the first binding moiety can be present on many different cell-types, specific or even unique to the target cell.

In other embodiments, the effector function can be desirable, thereby stimulating or modulating the cellular activity of the target cell which can enhance therapy. An example of where such a therapy can be desirable is in the delivery of a negative selection marker or suicide protein to a tumor where the target cell is a lymphokine and the ligand is a cytokine. Where the lymphokine is stimulated, the cell, can also possess therapeutic value in the recruitment of an endogenous immune response against the tumor, thereby increasing the therapeutic benefit of the therapy.

The phrase "substantially the same sequence" is intended to include sequences which bind the surface protein and possess a high percentage of (e.g., at least about 90%, preferably at least about 95%) sequence identity with the native sequence. The modifications to the sequence can be conserved or non-conserved, natural and unnatural, amino acids and are preferably outside of the binding domain. Amino acids of the native sequence for substitution, deletion, or conservation can be identified, for example, by a sequence alignment between proteins from related species or other related proteins.

In addition to the first binding moiety, there can be a second binding moiety which is a chemical entity which binds to HDAg. The binding can be via a covalent bond, ionic bonding, hydrogen bonding or other mechanism. The second binding moiety can be the same or different from the first. For example, it can be a peptide, sugar, lipid, steroid, nucleic acid, small molecule, anion or cation, or combination thereof which binds the HDAg. In one embodiment, the second binding moiety of the fusion protein is also a polypeptide. One embodiment of the second binding moiety comprises an antigen-binding fragment of an antibody which recognizes and binds to an antigen.

Ligand receptors which are cellular receptors can be transmembrane proteins comprising intracellular, transmembrane (characterized by highly hydrophobic regions in the sequence) and extracellular domains. In one embodiment, the second binding moiety can comprise the native extracellular domain of a receptor molecule.

Fusion proteins can be made conveniently through known methods, e.g. recombinantly. The binding moieties can be directly bonded to HDAg or can be bonded to HDAg through a linking moiety. Where one or both of the moieties are polypeptides, a peptide bond or peptide linker may be preferred, thereby obtaining a "fusion protein". The "fusion protein" of the HDAg and one or more moieties can be expressed by a single nucleic acid construct in series. One or more moieties and HDAg alternatively be linked directly or indirectly other than via a peptide bond or peptide linker, thereby obtaining a "conjugate".

Where the moieties and HDAg are directly bonded to each other, the bond can be covalent, as in a peptide bond, ionic bond or hydrogen bond. Where the bond is a peptide bond, a binding moiety can be bonded to the N terminus of HDAg via the C terminus, or vice versa, or both. It is acknowledged that one fusion protein may possess greater activity than a second fusion protein due to conformational or steric considerations. The binding moieties can be, for example, monomers, dimers and tetramers.

Where one or more of the binding moieties are not polypeptides, they can be joined via chemical reaction through functional groups present on each moiety which, under the appropriate conditions, will react with each other. For example, acid groups (or activated derivatives thereof) can be reacted with amines, alcohols or thiols to form amide or ester bonds, as is known in the art.

Alternatively and advantageously, a linking moiety is employed to link the binding moieties, e.g. binding partners, to HDAg. The linker can preferably be a flexible linker and sufficient in length to separate the moieties in space, thereby not restricting the ability of the fusion molecule to bind independently and maintain the proper conformation. Again, where both moieties are polypeptides, the linker moiety will generally be a peptide, polypeptide, or a "pseudopeptide". A "pseudopeptide" is a bifunctional linker which contains at least one non-amino acid and reacts to form a peptide bond, or other bond, with the terminal amine or carboxyl group of the moiety. For example, a peptide characterized by substitution of the terminal amine for a carboxyl group can function to react with the amine terminus of each moiety. Such as linker is considered to be a "pseudopeptide." Similarly, a peptide characterized by substitution of the terminal carboxyl for an amine group can function to react with the carboxyl terminus of each moiety.

Generally, however, the linker will be a peptide linker which will link the amine terminus of a moiety to the carboxyl terminus of HDAg or vice versa. One advantage to such a molecule is the ability to express the fusion protein in a recombinant host cell with a single nucleic acid construct.

Peptide linkers can be obtained from immunoglobulin hinge regions, such as a proline-rich region. Also, linkers can be characterized by little steric hindrance, thereby permitting maximal independent movement of the two moieties, such as with a polyglycine linker. Alternatively, the linker selected to be reactive to or inert to cellular proteases can be desirable. In another embodiment, the linker can be selected to avoid or minimize an immune response against the fusion molecule. The length of the linker also is not particularly critical. Typically, the length of the linker can be between about 2 and about 20 amino acids. As can be seen, the selection of the particular linking group is not critical to the invention.

In yet another embodiment, the linker can be a bifunctional compound which will react with other functional groups on the binding moieties or HDAg, such as in the reaction of acids and amines or alcohols (as present in peptides, carbohydrates and lipids, for example) in the formation of amides or esters.

A preferred combination of the above first and second binding moieties includes one binding partner, e.g. a polypeptide ligand to a cell-type specific cellular receptor linked, via a peptide linker, through a terminus of the ligand to the terminus of HDAg. A second binding partner, e.g. a extracellular domain of a cellular receptor or a mutant thereof, can be linked to the same or different HDAg subunit in the same manner.

For example, the C terminus of a binding polypeptide is linked to the N terminus of HDAg via the polypeptide linker or the N terminus of the first binding polypeptide is linked to the C terminus of the HDAg via the polypeptide linker.

In another aspect of the invention, peptidomimetics (molecules which are not polypeptides, but which mimic aspects of their structures to bind to the same site) that are based upon the above-described polypeptides, can also be used. For example, polysaccharides can be prepared that have the same functional groups as the polypeptides of the invention, and which interact with binding partners in a similar manner. Peptidomimetics can be designed, for example, by establishing the three=dimensional structure of the polypeptide in the environment in which it is bound or will bind to the binding partner. The peptidomimetic can comprise at least two components, a binding entity or entities and a backbone or supporting structure entity.

The binding entities of the peptidomimetic are the chemical atoms or groups which will react or complex (as in the formation of a hydrogen or covalent bond) with a binding partner. In general, the binding entities in a peptidomimetic are the same as the polypeptide moieties. Alternatively, the binding entities can be an atom or chemical group which will react with the binding partner in the same or similar manner as the polypeptide. Examples of binding entities suitable for use in designing a peptidomimetic for a basic amino acid in a polypeptide are nitrogen containing groups, such as amines, ammoniums, guanidines and amides or phosphoniums. Examples of binding entities suitable for use in designing a peptidomimetic for an acidic amino acid in a polypeptide can be, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides and polymers (such as, polyvinyl alcohol or polylactide). It is preferred that the supporting structure possess substantially the same size and dimensions as the polypeptide backbone or supporting structure. This can be determined by calculating or measuring the size of the atoms and bonds of the polypeptide and peptidomimetic. For example, the nitrogen of the peptide bond can be substituted with oxygen or sulfur, thereby forming a polyester backbone. Likewise, the carbonyl of the peptide bond can be substituted with a sulfonyl group or sulfonyl group, thereby forming a polyamide.

Reverse amides of the peptide can be made (e.g., substituting one or more —CONH— groups for a —NBCO— group). In addition, the peptide backbone can be substituted with a polysilane backbone.

These peptidomimetic compounds can be manufactured by art-known and art-recognized methods. For example, a polyester corresponding to a given peptide can be prepared by the substituting a hydroxyl group for each corresponding amine group on the amino acids, thereby preparing a hydroxyacid and sequentially esterifing the hydroxyacids, optionally blocking the basic side chains and acids to minimize side reactions. Determining an appropriate chemical synthesis route can generally be readily identified upon determining the chemical structure using no more than routine skill.

The fusion molecules can be manufactured according to methods generally known in the art. For example, where one or both of the binding moieties is a nonpeptide, the fusion molecule can be manufactured employing known organic synthesis methods useful for reacting a functional or reactive group on the moiety with a functional or reactive group on the other moiety or, preferably, a linker. In carrying out the synthesis, derivation or inactivation of the functional group (s) required for binding to the moiety's binding partner should be avoided. Appropriate syntheses are highly dependent upon the chemical nature of the binding moiety and, generally, can be selected from an organic chemistry text, such as March et al. *Advanced Organic Chemistry*, 3rd Edition (1985) John E. Wiley & Sons, Inc., New York, N.Y., or other known methods.

Where the binding moieties are polypeptides, the fusion molecule can be a conjugate or a fusion protein and manufactured according to known methods. Where a fusion protein is desired, the molecule can be manufactured according to known methods of recombinant DNA technology. For example, the fusion protein can be expressed by a nucleic acid molecule comprising sequences which code for both moieties, such as by a fusion gene (nucleic acid molecule). Thus, the invention further relates to nucleic acid molecules, including fusion genes, which encode HDAg fragments, mutants and derivatives.

Nucleic Acid Molecules

Recombinant or isolated nucleic acid molecules of the invention, in one embodiment, encode an HDAg protein (including the e.g., native proteins, fragments, derivatives, mutants and allelic variants) as defined herein. A nucleic acid molecule of the present invention can be double-stranded or single-stranded and can be a DNA molecule, such as cDNA or genomic DNA, or an RNA molecule. The nucleic acid molecule can be placed in a construct, which can be inserted into a vector. As such, the nucleic acid molecule can include one or more exons, with or without, as appropriate, introns. In one embodiment, the nucleic acid molecule contains a single open reading frame which encodes HDAg and one or more binding moieties and, optionally, a signal sequence and/or a polypeptide linker, when present. By way of example in a multi-exon construct, the nucleic acid molecule contains a first exon which begins with an ATG, encodes a binding moiety, and optionally the polypeptide linker, and ends with a splice donor site. The construct would also contain an HDAg-coding nucleic acid sequence and would further would contain an intron followed by a second exon which begins with a splice acceptor site and, optionally, a polypeptide linker, coding sequences for a second binding moiety and ending with a stop codon. Alternative combinations of these elements would be apparent to the person of skill in the art.

As such, the nucleic acid molecule can include sequences which encode HDAg, and one or more moieties, as well as one or more of the following optional sequences, in a functional relationship: regulatory sequences (as will be discussed in more detail below) a start codon, a signal or leader sequence, splice donor sites, splice acceptor sites, introns, a stop codon, transcription termination sequences, 5' and 3' untranslated regions, polyadenylation sequences, negative and/or positive selective markers, and replication sequences.

The coding regions of the nucleic acid molecule code for HDAg and the binding moeity or moieties and any polypeptide linkers present. Where the binding moiety is a native ligand or cellular surface protein (e.g. a cellular receptor), or a binding fragment thereof, the nucleic acid molecule coding regions can correspond to the native sequences which encode a binding moiety. Because many amino acids are encoded by a plurality of codons, the coding sequence can be mutated to result in the same amino acid sequence. This may be advantageous where a codon is preferred by the selected host cell. In one embodiment, the HDAg gene can be altered such that the codons conform to the known codon use preferences for *E. coli*. See FIG. 9 (SEQ ID NO:10) and FIGS. 15–17 (SEQ ID NOS:21, 10 and 25). The gene can be inserted into a convenient expression vector which allows production of several forms of the capsid protein including residues 1–84 (terminated in the middle domain), the short isoform and the long isoform. Dingle et al., J. Virol, (1998). All three forms express well. Preferably, the nucleic acid molecule comprises the or corresponding coding nucleotide sequence of FIGS. 9, 10, 15–16 (SEQ ID NOS:10, 12–14, 21, 23), or substantially the same sequences thereof, or the complement thereof. In another embodiment, the nucleic acid molecule does not possess the nucleotide sequence of GenBank Accession #M28267. The nucleic acid molecule can be, for example, isolated and/or purified or recombinant.

In a preferred embodiment, the nucleic acid molecule comprises the nucleotide sequence depicted in FIG. 9 (SEQ ID NO:10), nucleotides 37–150 of FIG. 9 (nucleotides 37–150 of SEQ ID NO:10), nucleotides 37–186 of FIG. 9 (nucleotides 37–186 of SEQ ID NO:10), FIG. 10 (SEQ ID NOS:12–14), nucleotides 1421–1566 of FIG. 10 (nucleotides 1421–1566 of SEQ ID NOS:12–13) or nucleotides 1457–1566 of FIG. 10 (nucleotides 1457–1566 of SEQ ID NOS:12–13), FIG. 15 (SEQ ID NOS:21 and 23), FIG. 16 (SEQ ID NO:10); or a fragment or mutation thereof, which encodes a coiled-coil oligomer. In another preferred embodiment, the nucleic acid molecule comprises a nucleotide sequence encoding a polypeptide comprising an amino acid sequence depicted in a row of FIG. 1 (SEQ ID NOS:1–8), amino acids 12–48 of a row of FIG. 1 (amino acids 12–48 of SEQ ID NOS:1–8), FIG. 3C (SEQ ID NO:9), FIG. 9 (SEQ ID NO:11), amino acids 12–48 of FIG. 9 (amino acids 12–48 of SEQ ID NO:11), FIG. 10 (SEQ ID NOS:15–17), amino acids 12–88 of FIG. 10 (amino acids 12–88 of SEQ ID NOS:15–17), or δ12–60(Y). Also encompassed in the invention are complementary strands of these sequences, DNA sequences that hybridize to these sequences and RNA sequences transcribed from these sequences. Also included are fragments or mutations thereof, which encode a coiled-coil oligomer.

In one embodiment, the nucleic acid molecule encodes a polypeptide of a fusion molecule described herein.

Also included are fusion nucleic acid molecules (e.g. fusion genes) comprising an HDAg nucleic acid molecule operably linked to a heterologous nucleic acid molecule ("heterologous gene"), which encodes a peptide which is not HDAg and not derived therefrom (i.e., "heterologous protein"). Where the binding moiety is a mutation or variant of a native sequence, as provided above, generally, the nucleic acid sequence can be mutated correspondingly. It may also be preferred for ease of manufacture of the nucleic acid sequence to maintain as much of the native sequence as possible. In one embodiment, the nucleic acid molecule shares at least about 50% sequence identity with the corresponding native sequence such as the coding region, for example, the coiled-coil region, e.g., amino acids 12–48 or amino acids 12–60. In one embodiment, the sequence identity is at least about 65%, more preferably, 75%. In a more preferred embodiment, the percent sequence identity is at least about 90%, and still more preferably, at least about 95%.

Recombinant nucleic acid molecules meeting these criteria comprise nucleic acids having sequences identical to sequences of naturally occurring genes, including polymorphic or allelic variants, and portions (fragments) thereof, or variants of the naturally occurring genes. Such variants include mutants differing by the addition, deletion or substitution of one or more residues, modified nucleic acids in which one or more residues are modified (e.g., DNA or RNA analogs), and mutants comprising one or more modified residues.

Many nucleic acid molecules coding for suitable binding moieties are known in the art and can be obtained from, for example, GENBANK. Alternatively, other sequences can be employed, such as homologs of known genes.

Such homologous nucleic acids, including DNA or RNA, can be detected and/or isolated by hybridization (e.g., under high stringency conditions or moderate stringency conditions). "Stringency conditions" for hybridization is a term of art which refers to the conditions of temperature and buffer concentration which permit hybridization of a particular nucleic acid to a second nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, containing supplements up through Supplement 29, 1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

By varying hybridization conditions from a level of stringency at which no hybridization occurs to a level at which hybridization is first observed, conditions which will allow a given sequence to hybridize (e.g. selectively) with the most similar sequences in the sample can be determined.

Exemplary conditions are described in Krause, M. H. and S. A. Aaronson, *Methods in Enzymology*, 200:546–556 (1991). Also, see especially page 2.10.11 in *Current Protocols in Molecular Biology* (supra), which describes how to determine washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought. The following table provides an example of each condition of stringency.

| Stringency | % Allowed mismatch | ° C. Temperature | % Formamide |
| --- | --- | --- | --- |
| High | 6.6 | 52 | 50 |
| Medium | 13 | 45 | 50 |
| Low | 27 | 45 | 22 |

"Selective isolation", or "selective hybridization", is defined herein as embracing the isolation of a sufficiently few number of molecules (preferably one) as to readily permit the identification of the nucleic acid of interest.

The nucleic acid molecule also preferably comprises regulatory sequences. Regulatory sequences include cis-acting elements that control transcription and regulation such as, promoter sequences, enhancers, ribosomal binding sites, and transcription binding sites. Selection of the promoter will generally depend upon the desired route for expressing the protein. For example, where the molecule will be introduced (e.g. transformed) into a cell by a viral vector, e.g. a plasmid, preferred promoter sequences include viral, such as retroviral or adenoviral, promoters. Examples of suitable promoters include the cytomegalovirus immediate-early promoter, the retroviral LTR, SV40, and TK promoter. Where the molecule is to be expressed in a recombinant eukaryotic or prokaryotic cell, the selected promoter is recognized by the host cell. In one embodiment the construct is a cassette expression system. A suitable promoter which can be used can include the native promoter for the binding moiety which appears first in the construct.

The elements which comprise the nucleic acid molecule can be isolated from nature, modified from native sequences or manufactured de novo, as described, for example, in the above-referenced texts. The elements can then be isolated and fused together by methods known in the art, such as exploiting and manufacturing compatible cloning or restriction sites.

Vectors and Host Cells

The nucleic acid molecules can be inserted into a construct, e.g. a vector, such as a plasmid or cassette expression system, which can, optionally, replicate and/or integrate into a recombinant host cell, by known methods.

The vectors of the present invention comprise a nucleic acid molecule which encodes HDAg (e.g. an HDAg monomer). The monomer can be a subunit of an HDAg coiled-coil oligomer, e.g. an octamer. The oligomer can comprise an HDAg polypeptide as described herein. The nucleic acid molecule thus includes any of the nucleic acid molecules described herein, for example, a native (wild type) nucleic acid, or a fragment, mutant or derivative. Especially preferred are nucleic acids encoding full-length HDAg (e.g. HDAg-S or HDAg-L) or a fragment or derivative thereof, (e.g. a functional fragment) capable of forming a coiled-coil octamer (e.g. an N-terminal coiled-coil octamer). Preferred vectors comprise a nucleic acid molecule comprising nucleotide sequence depicted in FIG. 9 (SEQ ID NO:10), nucleotides 37–150 of FIG. 9 (nucleotides 37–150 of SEQ ID NO:10), nucleotides 37–186 of FIG. 9 (nucleotides 37–186 of SEQ ID NO:10), FIG. 10 (SEQ ID NOS:12–14), nucleotides 1421–1566 of FIG. 10 (nucleotides 1421–1566 of SEQ ID NOS:12–13) or nucleotides 1457–1566 of FIG. 10 (nucleotides 1457–1566 of SEQ ID NOS:12–13), FIG. 15 (SEQ ID NOS:21, 23) and FIG. 16 (SEQ ID NO:10). Preferred vectors also comprise a nucleic acid comprising a nucleotide sequence encoding a polypeptide comprising an amino acid sequence depicted in a row of FIG. 1 (SEQ ED NOS:1–8), amino acids 12–48 of a row of FIG. 1 (amino acids 12–48 of SEQ ID NOS:1–8), the top row of FIG. 3C (SEQ ID NO:9), FIG. 9 (SEQ ID NO:11), amino acids 12–48 of FIG. 9 (amino acids 12–48 of SEQ ID NO:11), FIG. 10 (SEQ ID NOS:15–17), amino acids 12–88 of FIG. 10 (amino acids 12–88 of SEQ ID NOS:15–17), FIG. 11B (SEQ ID NOS:18–20), FIG. 17 (SEQ ID NO:25) or δ12–60(Y). Other preferred vectors comprise nucleic acids comprising sequences which are the complementary strands of the above, DNA sequences which hybridize to these sequences, RNA sequences transcribed from these sequences, and fragments and mutations thereof, which encode a coiled-coil oligomer, e.g. an octamer. Vectors can also comprise fusion molecules comprising HDAg and at least one binding moiety, as described herein.

In a preferred embodiment, the vector additionally comprises at least one multiple cloning site. A multiple cloning site comprises a cleavage sites for commonly used restriction sites to facilitate incorporation of foreign (non-HDAg) gene, e.g. a cassette. A multiple cloning site can be located 3' or 5' to the nucleic acid molecule encoding HDAg. There can be multiple cloning sites, for example, there can be a multiple, cloning site 3' of the HDAg nucleic acid molecule and another multiple cloning site 5' to the HDAg nucleic acid molecule. The multiple cloning site can be located in a flanking region.

The vector can further comprise nucleic acid encoding a nuclear localization signal, e.g. an HDAg nuclear localization signal, for example, amino acids 68–88 of HDAg, as shown in FIG. 9 (amino acids 68–88 of SEQ ED NO:11). The vector can also comprise an HDAg nucleic acid molecule comprising a sequence encoding a coiled coil and a nuclear localization signal.

The vectors of the invention can be used for the expression of a fusion molecule as described herein. A heterologous (non-HDAg) nucleic acid molecule, e.g., a gene, encoding a binding moiety of a fusion molecule can be inserted into a vector comprising HDAg, e.g., into a multiple cloning site. A vector can comprise one heterologous gene or more than one heterologous gene. The genes can be the same or different. A first heterologous gene can encode a first binding moiety and a second heterologous gene can encode a second binding moiety. The first and the second binding moieties can be binding partners as described herein (for example, single chain antibody and antigen, ligand and receptor, components of a linked pathway, etc). The heterologous gene or genes and the nucleic acid encoding HDAg can be operably linked, e.g., in the same open reading frame. Where HDAg nucleic acid and a heterologous gene encoding a binding moiety are operably linked, they are expressed as a single protein unit, i.e., a fusion molecule.

In one embodiment, a vector comprises an HDAg nucleic acid molecule (e.g. a nucleic acid cassette) encoding a monomer capable of being a unit of a coiled-coil octamerization scaffold and a heterologous gene encoding a binding moiety, wherein the expressed binding moiety is bound to one terminal of the monomer, e.g. the N terminus or the C terminus. Where there are two expressed heterologous genes, each end of the monomer can be bound to an expressed binding moiety.

Vectors can additionally comprise a nucleic acid molecule encoding a nuclear localization signal, which can transport protein expressed by the vector to the nucleus of a cell.

The vectors described herein can express nucleic acid, e.g. a fusion gene, in a host cell, e.g. a procaryotic or eukaryotic cell. In one embodiment, the vector can be expressed in a bacteria cell, for example, *Escherischia*, e.g. *E. coli*. The nucleic acid in the vector can also be expressed in *Bacillus*. It can also be expressed in baculoviruses, *pichia* expressions systems, and animal tissue or cells, for example insect, mammal, e.g., a human, or yeast (such as *Saccharomyces*). Examples of specific cells include somatic or embryonic cells, HeLa cells, human 293 cells, monkey COS-7 cells, etc.

The vector can comprise a number of other components. For example, the vector can comprise a marker, for example a positive or negative selection marker, e.g. ampicillin or kanamycin. The vector can comprise two markers, wherein the first marker is capable of detecting propagation of a vector (e.g. a plasmid) in a bacterial cell and a second marker is capable of detecting propagation of the vector in a eukaryotic cell. The vector can comprise an origin of replication for bacteria and an origin of replication that is capable of mediating production of a single-stranded DNA by a bacteriophage, such as fl phage or M13 phage.

The vector can comprise a promoter. In one embodiment, the promoter is a viral promoter, such as a retroviral or adenoviral promoter. Examples of suitable promoters include T7, lac, trc, tac, CMV, SV40, the cytomegalovirus immediate-early promoter, the retroviral LTR and the TK promoter. In a preferred embodiment, the promoter can be selected for high-level expression. A promoter can be selected for optimal expression in bacteria, (e.g. T7, lac, trc, tac etc.) or in a eukaryotic cell (e.g. CMV or SV40).

Figure 13A:
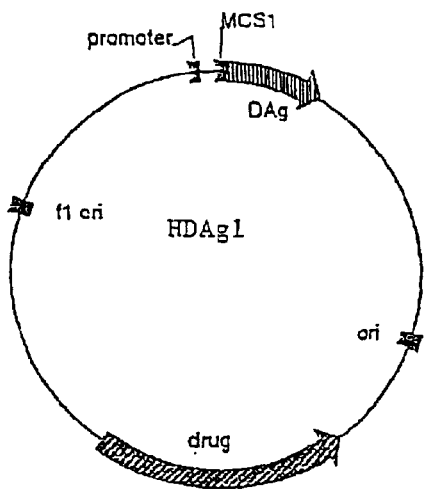
Figure 13B:
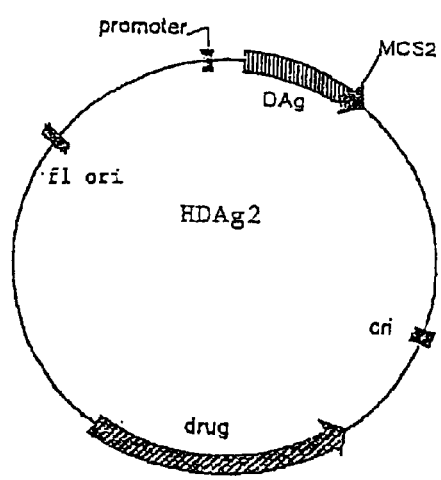
Figure 13C:
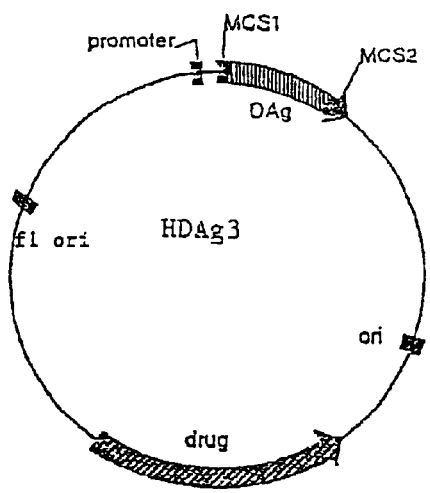
Figure 14:
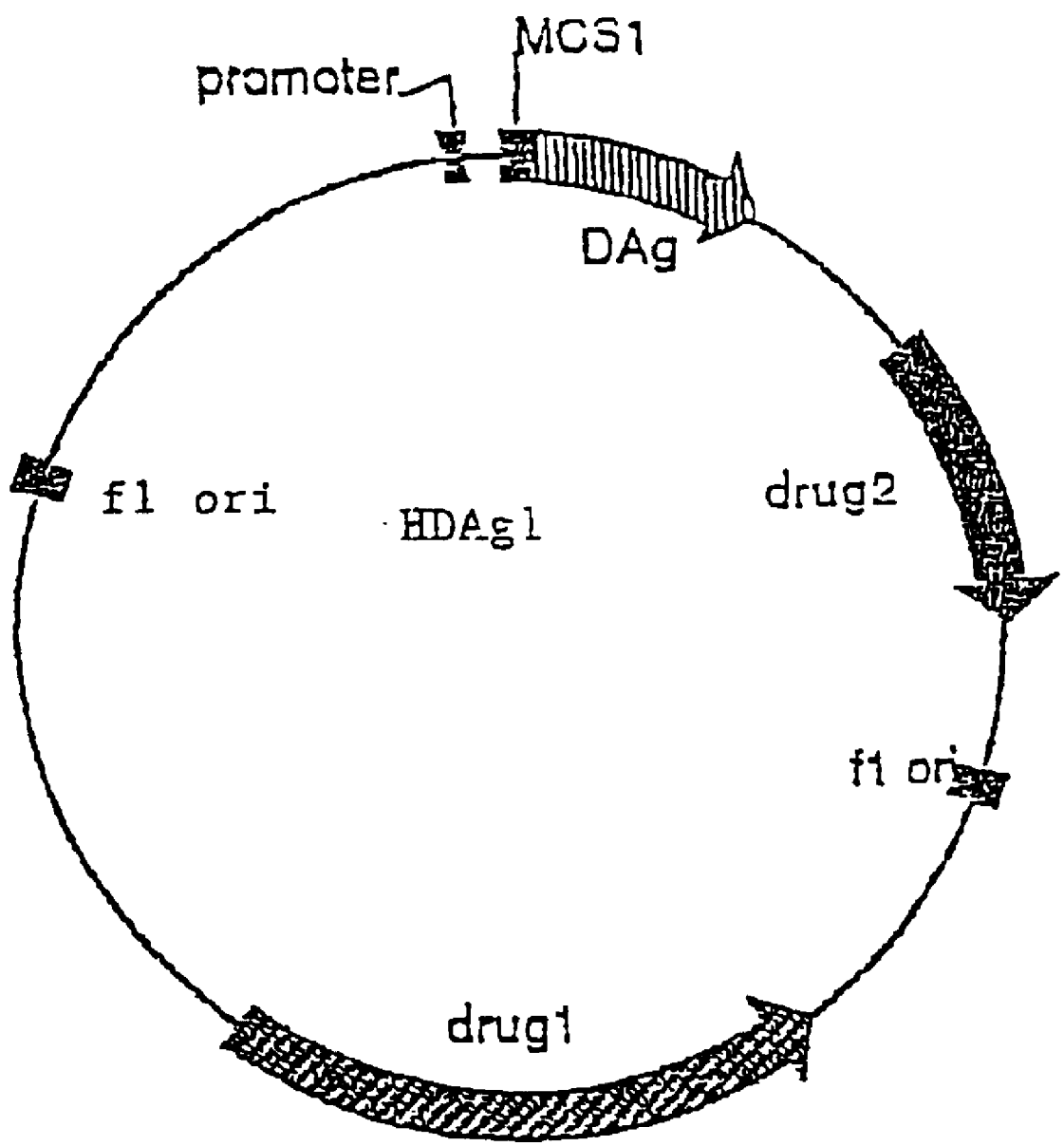

The vector can also comprise enhancers, ribosomal binding sites and transcription binding sites. In one embodiment is a vector depicted in FIG. 13A, B or C or FIG. 14. In one embodiment, a vector comprises HDAg nucleic acid (with or without a nuclear local signal), a heterologous gene, a marker, an origin of replication for a host cell, an origin of replication capable of mediating production of single-stranded DNA by a bacteriophage, a promoter, and a ribosome binding site. In one embodiment, the origin of replication is selected for maintaining plasmid expression is *E. coli*.

Figure 12A:
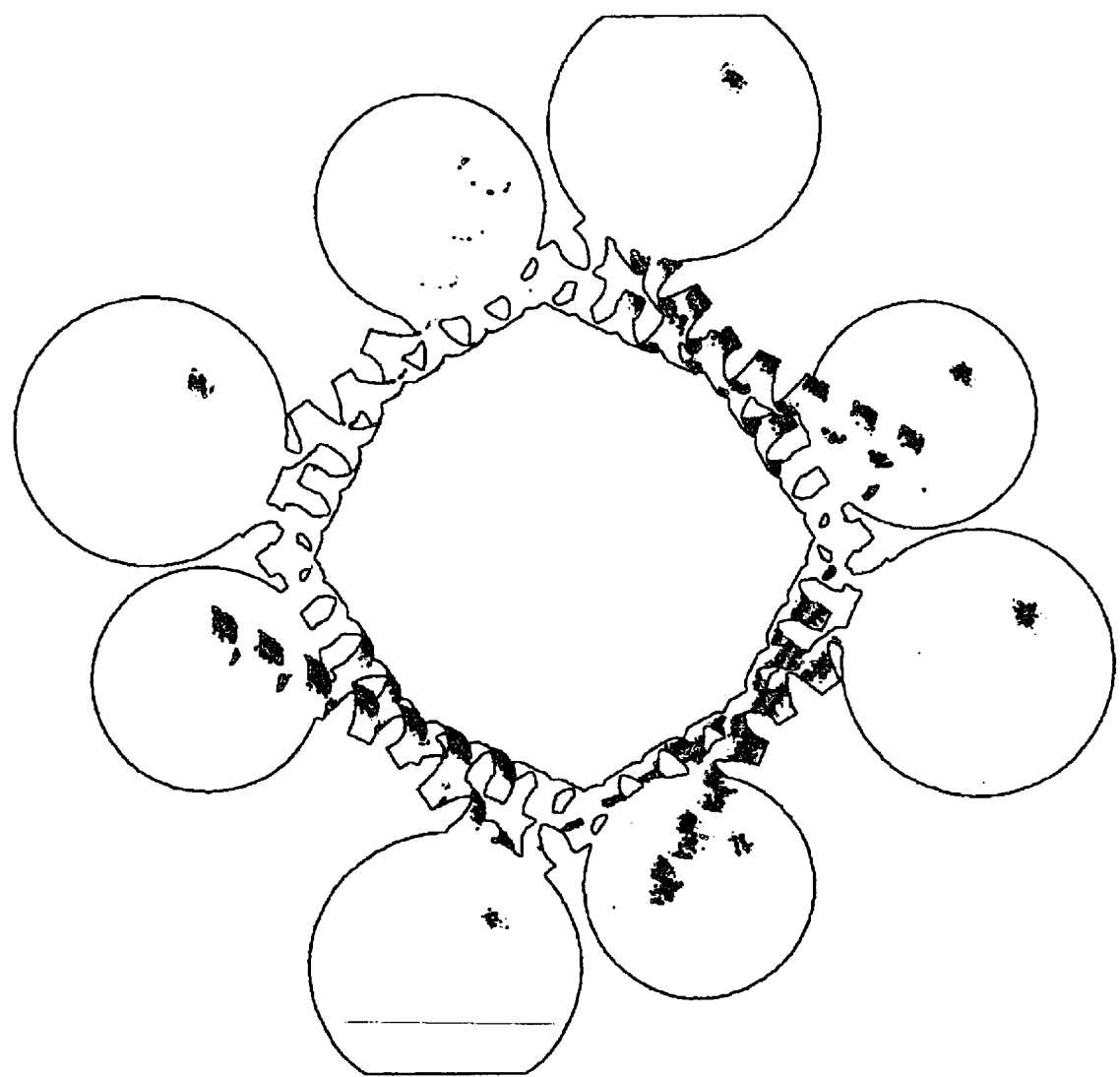
Figure 12B:
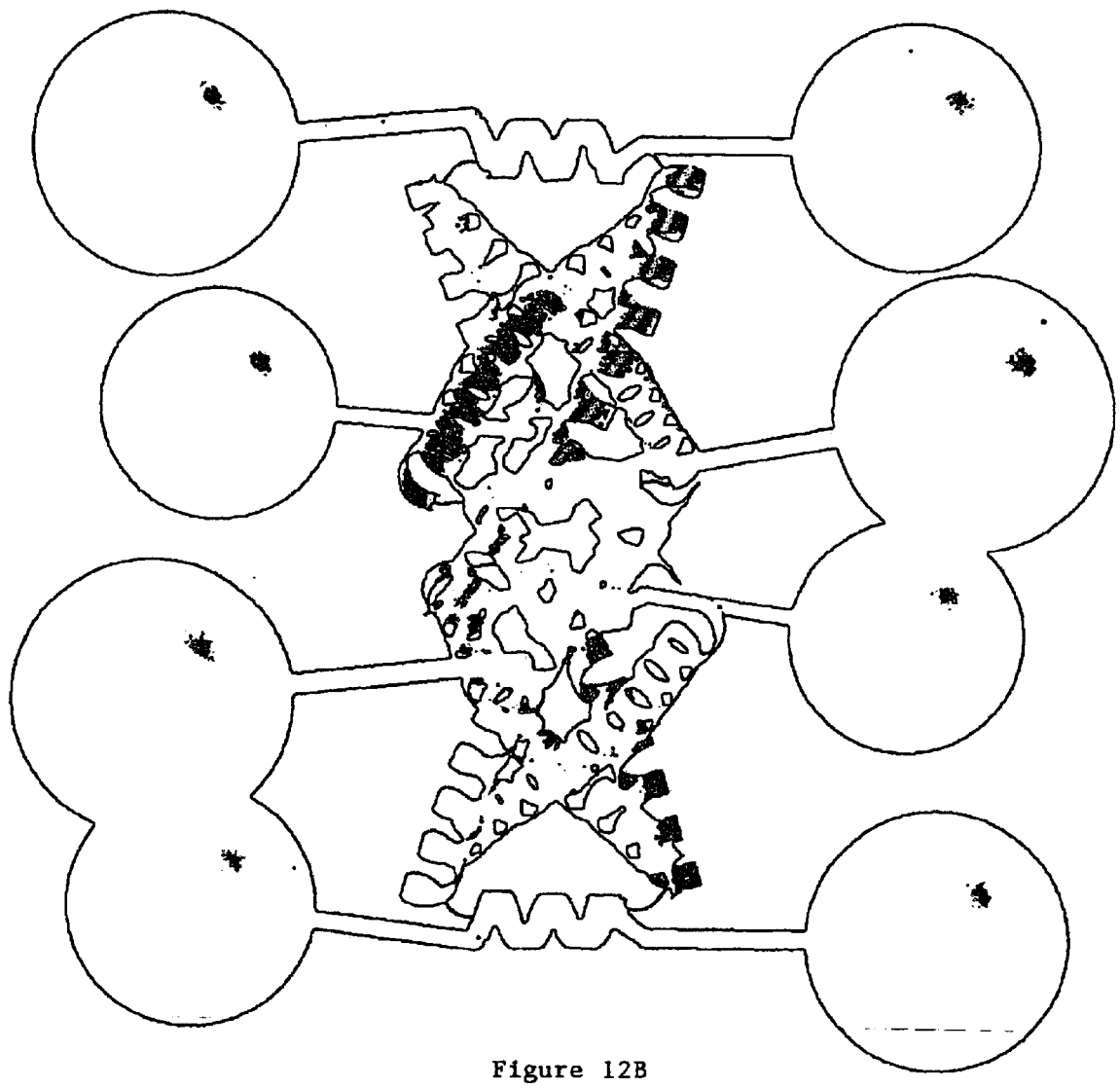

Especially preferred is a vector for overexpression of hepatitis delta antigen in *E. coli*, for example, a vector produced by the method as herein described in Example 2, below, e.g. a vector comprising a nucleic acid molecule sequence optimized for expression of HDAg in *E. coli*. The gene can be inserted into a vector which allows production of several forms of the capsid protein including residues 1–84 (terminated in the middle domain), the short isoform and the long isoform. In a preferred embodiment, the vector is pR5δV5. Another preferred embodiment is a cassette expression system which allows any expressed sequence or sequences (e.g. a binding moiety) to be appended to the N-terminus of C-terminus of the HDAg octamerization scaffold. In a preferred embodiment, the HDAg gene is mutated such that in the expressed peptide, a serine residue of HDAg is replaced with (substituted by) a cysteine to allow for convenient chemical cross-linking of the octamerization domain, e.g., to an inert support matrix (e.g. polyethylene glycol), to a synthetic peptide, to an oligosaccharide, to a small organic molecule, or to lipids. FIG. 12(A and B) depicts a representation of a construct containing eight appended protein domains on an HDAg octameric framework.

The vector can be viral. Viral vectors include baculovirus, retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus. Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Fundamental Virology, Third Edition, edited by B. N. Fields, D. M. Knipe, P. M. Howley, et al. Lippincott-Raven Publishers, Philadelphia (1996) and additional examples of viruses are described in detail in *Fields Virology*, Third Edition edited by B. N. Fields, D. M. Knipe, P. M. Howley et al., Lippincott-Raven Publishers, Philadelphia, Pa. (1996).

A nucleic acid molecule described herein can be introduced (incorporated or inserted) into the host cell, by known methods. Such cells, comprising such nucleic acid molecules, are encompassed in the invention. The host cell can be a eukaryotic or prokaryotic cell and includes, for example, baculoviruses, *Pichia* expression systems, yeast (such as *Saccharomyces*), bacteria (such as, *Escherichia* or *Bacillus*), animal cells or tissue, including insect or mammalian cells (such as somatic or embryonic human cells, Chinese hamster ovary cells, HeLa cells, human 293 cells and monkey COS-7 cells, etc.). Examples of suitable methods of transfecting or transforming cells include calcium phosphate precipitation, electroporation, microinjection, infection, lipofection and direct uptake. Methods for preparing such recombinant host cells are described in more detail in Sambrook et al., "Molecular Cloning: A Laboratory Manual," Second Edition (1989) and Ausubel, et al. "Current Protocols in Molecular Biology," (1992), for example.

The host cell is then maintained under suitable conditions for expression and recovering the molecule, e.g. a fusion molecule. Generally, the cells are maintained in a suitable buffer and/or growth medium or nutrient source for growth of the cells and expression of the gene product(s). The growth media are not critical to the invention, are generally known in the art and include sources of carbon, nitrogen and sulfur. Examples include Dulbeccos modified eagles media (DMEM), RPMI-1640, M199 and Grace's insect media. Again, the selection of a buffer is not critical to the invention. The pH which can be selected is generally one tolerated by or optimal for growth for the host cell.

The cell is maintained under a suitable temperature and atmosphere. Anaerobic host cells are generally maintained under anaerobic conditions. Alternatively, the host cell is aerobic and the host cell is maintained under atmospheric conditions or other suitable conditions for growth. The temperature should also be selected so that the host cell tolerates the process and can be for example, between about 30° and 40° C. for mammilian cells and between 20 and 40° C. for bacteria, yeast and insect cells.

The recombinant molecules, including fusion molecules, produced by the processes described herein can be isolated and purified by known means. Examples of suitable purification and isolation processes are generally known and include ammonium sulfate precipitation, dialysis, gel filtration, immunoaffinity, chromatography, electrophoresis, ultrafiltration, microfiltration or diafiltration.

In addition the fusion molecule can incorporate commonly used sequence tags e.g. his, tag or fla to facilitate purification via ligand affinity chromatograph. The fusion molecule is preferably purified substantially prior to use, particularly where the protein will be employed as an in vivo therapeutic, although the degree of purity is not necessarily critical where the molecule is to be used in vitro. In one embodiment, the bifunctional molecule can be isolated to about 50% purity (by weight), more preferably to about 80% by weight or about 95% by weight. It is most preferred to employ a molecule which is essentially pure (e.g., about 99% by weight or to homogeneity).

Fusion molecules which are prepared according to the above method can be used directly in the disclosed methods or can be screened for an activity prior to use. To screen the fusion molecule for activity, for example, in vitro, the fusion molecule (or mixtures of fusion molecules) can be contacted with, for example, the binding partner of a binding moiety of the fusion molecule under conditions suitable for binding and then assayed for binding. For example, a fusion molecule comprising a ligand can be screened for the ability to bind the ligand's receptor, or the binding protein of the ligand's receptor, in vitro, by contacting the receptor (or portion thereof) and the fusion molecule under conditions suitable for binding and detecting binding.

Methods

The HDAg molecules of the invention are useful in a variety of methods. The N-terminal octamer may serve as a convenient high valency framework for linking, presenting or delivering a variety of binding moieties, e.g. as described above. For example, the molecules are useful in the delivery of one or more therapeutic agents, such as drugs, proteins or polynucleotides (e.g., genes) or products thereof to a patient. The polynucleotide or the product thereof can be a therapeutic agent. In one embodiment, therapeutic polynucleotide includes RNA (e.g., ribozymes) and antisense DNA that prevents or interferes with the expression of an undesired protein in the target cell. The polynucleotide can also encode a heterologous therapeutic protein. A heterologous protein or polynucleotide is one which is not HDAg. Examples of therapeutic proteins include antigens or immunogens such as a polyvalent vaccine, cytokines, tumor necrosis factor, interferons, interleukins, adenosine deaminase, insulin, T-cell receptors, soluble CD4, epidermal growth factor, human growth factor, blood factors, such as Factor VIII, Factor IX, cytochrome b, glucocerebrosidase, ApoE, ApoC, ApoAI, the LDL receptor, negative selection markers or "suicide proteins", such as thymidine kinase (including the HSV, CMV, VZV TK), anti-angiogenic factors, Fc receptors, plasminogen activators, such as t-PA, u-PA and streptokinase, dopamine, MHC, tumor suppressor genes such as p53 and Rb, monoclonal antibodies, antigen binding fragments or constant regions thereof, drug resistance genes, ion channels, such as a calcium channel or a potassium channel, and adrenergic receptors, etc.

Also encompassed by the present invention are the use of HDAg fusion molecules for high through put screening assays, such as for detecting ligand and cell specific receptor binding pairs. The ligand and/or receptor can be peptides (including post-translationally modified proteins) and/or small molecules (including sugars, steroids, lipids, anions or cations). The ligands and ligand-cell specific receptors can be known or unknown. Where the ligand is known and the receptor is unknown, ligand-cell specific receptors can be identified, for example, by screening for host cells transfected with nucleotides encoding potential receptors. For example, the ligands can be secreted (such as chemokines) or non-secreted (such as the extracellular domains of chemokines receptors) proteins.

A library of host cells displaying putative ligand-cell surface receptors can be obtained by transfecting suitable host cells with nucleic acid constructs, including but not limited to cDNA or genomic libraries, under appropriate regulatory control to result in the expression of cell-surface receptors on the host cell. The fusion molecule with ligand is added to the population of host cells under conditions suitable for introduction. Introduction can be detected, for example, with a label. A similar approach can be used to select unknown ligands in the case where the ligand-cell specific receptors are known and the ligand is unknown. In this embodiment, a library of fusion molecules with putative ligands (e.g., chemokines) can be obtained and contacted with one or more host cells displaying cell surface receptors.

A similar approach can be used to identify unknown ligands, test substances, drugs wherein the cell surface receptor is known, where the fusion molecule comprises a binding moiety which is a receptor which binds a surface molecule. The host cell expresses a distinct ligand or a collection of recombinant ligands. Ligand-receptor binding can be detected following introduction of the molecule to the host cell.

The invention is also particularly useful for vaccine delivery. In this embodiment, an antigen or immunogen can be expressed heterologously (e.g., by recombinant insertion of a nucleic acid sequence which encodes the antigen or immunogen (including antigenic or immunogenic fragments) into a vector comprising HDAg). Alternatively, the antigen or immunogen and HDAg can be expressed in a live attenuated, pseudotyped virus vaccine, for example. Generally, the methods can be used to generate humoral and cellular immune responses, e.g. via expression of heterologous pathogen-derived proteins or fragments thereof in specific target cells.

The dosage administered (e.g., the effective amount) will, of course, vary depending upon known factors such as the pharmacodynamic characteristics of the particular agent, e.g., the therapeutic binding entity, and its mode and route of administration; age, health, and weight of the recipient; nature and extent of symptoms, kind of concurrent treatment, frequency of treatment, and the effect desired.

It can be administered one to several times per day, depending on the mode of administration. Effective doses can be determined by those of skill in the art. An effective dose of an agent is an amount sufficient to relieve the individual of the symptoms of the disorder which the agent is intended to treat.

Methods of introduction of the agent at the site of treatment include, but are not limited to, intradermal, intramuscular, intraperitoneal, intravenous, subcutaneous, oral, intranasal, gene therapy, cellular implantation or particle bombardment. Other suitable methods include or employ biodegradable devices and slow release polymeric devices.

Because proteins are subject to being digested when administered orally, parenteral administration, e.g., intravenous, subcutaneous, or intramuscular, would ordinarily be used to optimize absorption.

For parenteral administration, particularly suitable are injectable, sterile solutions, preferably oily or aqueous solutions, as well as suspensions, emulsions, or implants, including suppositories. The molecule comprising the agent can be administered in a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques. Suitable pharmaceutical carriers are described in the most recent edition of Remington's Pharmaceutical Sciences, A. Osol, a standard reference text in this field of art. Ampules are convenient unit dosages. Formulations for transdermal or transmucosal administration generally include penetrants such as fusidic acid or bile salts in combination with detergents or surface-active agents. The formulation can then be manufactured as aerosols, suppositories, or patches.

Oral agents may be administered if formulated as to be protected from digestive enzymes. If administered orally, the SCR-P will be administered in a therapeutic composition which may also include an appropriate carrier (e.g., a physiologically compatible carrier), a flavoring agent and a sweetener.

Suitable pharmaceutical carriers include, but are not limited to water, salt solutions, alcohols, polyethylene glycols, gelatin, carbohydrates such as lactose, amylose or starch, magnesium stearate, talc, silicic acid, viscous parafin, fatty acid esters, hydroxymethylcellulose, polyvinyl pyrolidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active agents, e.g., enzyme inhibitors, to reduce metabolic degradation.

Using procedures similar to those described above, HDAg molecules (e.g. fusion molecules) and vectors (e.g. cassette expression systems) comprising nucleic acid molecules, such as the vectors described herein, can be used for a variety of purposes. For example, the vector comprising all or part of a nucleic acid sequence of FIG. 9 (SEQ ID NO:10) or FIG. 15 (SEQ ID NO:21)(synthetic) can be used to overexpress the hepatitis delta antigen in bacteria.

In a preferred embodiment, multiple copies of a binding moiety (e.g. a peptide or domain) can be expressed using the vectors described herein, e.g., by inserting a nucleic acid cassette encoding the moiety into the vector, transforming a host cell with the vector and culturing the cell under conditions sufficient for expression of the moiety. Up to sixteen copies of the moiety (eight at the C terminus of the HDAg monomer and eight at the N terminus) can be made in this way. In a preferred embodiment, the vector is one depicted in a Figure selected from the group consisting of FIGS. 13A, 13B, 13C and 14.

In one embodiment, a vector or molecule described herein can be used for a high valency expression of a binding moiety, for example, a peptide or protein domain, e.g., an antigen. In another embodiment, the vector can be used to express a high valency display of at least two different peptides or protein domains, to enhance interaction between ligands. The interaction between ligands can occur in solution, on membranes or on surfaces.

In another embodiment, interaction (e.g., fusion) between two cells (or two cell types) can be mediated or enhanced by, for example, associating an HDAg octamer expressing multiple copies of a domain which interacts with a ligand on the surface of cell type one and multiple copies of a domain which interacts with a ligand on the surface of cell type two. This method could work for embodiments involving more than two cells or cell types as well. A fusion molecule, e.g., an octamer construct of the present invention, which can be coupled to a surface, for example, by chemical cross-linking or by inclusion of at least one copy of a second domain which interacts with a ligand displayed on a surface, can be used to display multiple copies of a domain on a surface. In another embodiment, the octamer can be used to express different enzymes from a linked pathway on a single framework, e.g., for facilitating rapid exchange of substrates and products between enzymes from a single pathway. The enzymes implicated Krebs in the can be cycle.

In another embodiment, the octamer can also be used to link a first binding moiety, e.g. a peptide or domain mediating (specifying) an interaction (an "interaction" domain) and a second binding moiety, which mediates an effect (an "effector" domain). In another embodiment, the effector domain is a chemical, e.g. a drug, linked to the octamer via a free —SH group on the octamer. In a preferred embodiment, the interaction domain mediates interaction with a specific receptor on a cell surface, and the effector domain generates a specific function, such as cell killing.

In another embodiment, the octamer can contain one or more copies of an domain for interaction with a ligand, and one or more copies of a domain which is a label (e.g. alkaline phosphatase, radiolabel, streptodevice, and green fluorescent protein) for amplifying a signal in a solid phase assay, e.g. an ELISA assay.

In another embodiment, an oligomer construct can be used to couple an oligonucleotide which interacts (e.g. hybridizes) with a nucleic acid molecule in the cell (e.g. a specific complementary DNA or RNA sequence) and one or more copies of an effector to target specific DNA or RNA sequences for cleavage. In a preferred embodiment, the effector is a double-stranded nuclease. In a preferred embodiment, the octamer is a mutant with a free sulfhydryl (—SH) group. An octamer construct can be used to couple multiple copies of a ligand in such a way that the interaction of the octamer with a cell triggers signaling or internalization by pathways which depend on the multimerization of a receptor or ligand on the cell surface. The vectors can be used to promote interaction between intracellular components in a signal transduction pathway, for example components which are upstream or downstream from each other.

In another embodiment, the system can be used to mediate efficient (drive) gene expression by coupling (e.g. covalently) an enhancer recognition protein and at least one promoter binding protein.

In another embodiment, the system can be used as a high valency trap to identify the vector can be used as a diagnostic. In one embodiment, the binding moiety is Sp120 and the molecule is used to test for the presence of Human Immunodeficiency Virus. In another embodiment, at least one binding moiety is a drug which has a therapeutic effect when administered to an animal. In another embodiment, a molecule of the present invention is used to screen test substances for an effect. In another embodiment, an agent can be administered to a patient, wherein the agent will inhibit formation of the coiled coil HDAg oligomer. Peptides (e.g. proteins) and nucleic acids, as discussed above, the inventions described herein are based upon the discovery that the HDAg protein oligomerizes to a coiled-coil octamer. The HDAg protein is derived from the Hepatitis D virus which bind to peptides or protein domains.

In another embodiment, at least one binding moiety is a drug which has a therapeutic effect when administered to an animal.

In another embodiment, a molecule of the present invention is used to screen test substances for an effect.

In another embodiment, an agent can be administered to a patient, wherein the agent will inhibit formation of the coiled coil HDAg oligomer.

As discussed above, the inventions described herein are based on the discovery that the HDAg protein oligomerizes to a coiled-coil octamer. The HDAg protein is derived from the Hepatitis D virus.

Whereas Hepatitis B virus infection alone generally causes mild, sometimes chronic, hepatitis, coinfection of hepatitis D virus (HDV) with hepatitis B virus (HBV) causes severe, and often fatal, liver disease in humans, and is the most common cause of fulminant viral hepatitis, Hoofnagle, J. H., *J. Am. Med. Assoc.*, 261:1321–1325 (1989). The virus is an obligatory subviral satellite of HBV, requiring the hepatitis B surface antigen (HBsAg) for assembly and cell-to-cell transmission. Rizzetto, M. et al., *Proc. Natl. Acad. Sci. USA*, 77:6124–6128 (1980). However, the viral genome can replicate in the absence of HBV. Kuo, M. Y. P et al., *J. Virol.* 63:1945–1950 (1989). Hepatitis delta encodes all of the information required to direct replication of its RNA genome by the host RNA Pol II. Efficient transmission of hepatitis delta virus requires that the viral RNA and the capsid protein be encapsidated within the hepatitis B virus surface antigen. The viral genome is a 1.7 kilobase single-stranded circular RNA, which is approximately 70% complementary to itself, Wang, K. S. et al., *Nature*, 323:508–513 (1986), and forms a rod-like structure, Kos., A. et al., *Nature*, 323:558–560 (1986). The virus is believed to replicate by a double rolling-circle mechanism in infected cells, Taylor, J., *Cell*, 61:371–373 (1990). Both the genomic and antigenomic strands of the virus contain ribozymes, Wu, H. et al., *Proc. Natl. Acad. Sci. USA* 86:1831–1835 (1989), Wu, H. N. et al, *Science* 243:652–654 (1989), Sharmeen, L. et al., *J. Virol.*, 62:2674–2679 (1988), Kuo, M. et al., *J. Virol.* 62:4439–4444, which are responsible for reducing multimeric viral genomes into unit length and for directing the religation of the linear genomes, Sharmeen, L. et al., *J. Virol.* 63:1428–1430 (1989). The antigenomic strand of the genome encodes the only viral protein known to be associated with HDV, the hepatitis delta antigen (HDAg)(also known as delta virus capsid protein). Wang, K. S. et al., *Nature* 323:508–513 (1986), Makino, S. et al., *Nature.* 329:343–346.

HDAg exists in two isoforms. Early in the life cycle of the virus, HDAg is expressed as a 195-amino acid protein, the small hepatitis delta antigen (s-HDAg), which functions as a transactivator of HDV RNA replication. This form predominates early in infection. Kuo, M. Y. P, et al., *J. Virol.* 63:1945–1950 (1989). Later in the life cycle of the virus, there is an RNA editing event that changes the UAG stop codon of the HDAg-S to a UGG codon, encoding a tryptophan. This allows translation to proceed for an additional 19 amino acids, resulting in a 214-amino acid residue form of the protein, the large delta antigen (HDAg-L). The 19 amino acids include a stop signal which allows the large isoform to be famesylated at its terminus. HDAg-L is a potent inhibitor (dominant repressor) of HDV replication, Chao, M. et al., *J. Virol.* 64:5066–5069 (1990), Glenn, J. S. & M. *J. Virol.* 65:2357–2361 (1991), and is also involved in packaging the viral RNA, Chang, F. L. et al. *Proc. Natl. Acad. Sci. USA* 88:8490–8494 (1991), Wang, C. J. et al., *J. Virol.* 65:6630–6636(1991), Ryu, W. S., et al., *J. Virol.* 66:2310–2315 (1992), and coencapsidation, i.e., the copackaging of the small antigens into the viral particle. It also directs association with the hepatitis B antigen. Chang, F. L. et al. *Proc. Natl. Acad. Sci. USA* 88:8490–8494 (1991), Ryu, W. S. et al., *J. Virol.* 66:2310–2315 (1992), Chang, M. F. et al., *J. Virol.*, 68:646–653 (1994). Both the large and small antigens are highly specific RNA-binding phosphoproteins. Chang, M. F. et al., *J. Virol.* 62:2403–241 0, Lin, J. H. et al., *J. Virol.* 64:4051–4058 (1990) and have been shown to recognize specifically the viral rod-like structure of the HDV viral genomes, Chao, M. et al., *J. Virol.* 65:4057–4062 (1991). Crosslinking studies have shown that both proteins can exist as either homomultimers (all small antigen or all large antigen) or as heteromultimeric structures (a mixture of small and large antigen) Xia, Y. P. & Lai, M. M. C., *J. Virol.* 66:6641–6848 (1992), Wang, J. G. & Lemon, S. M., *J. Virol.* 67:446–454 (1993), Chang, M. F. et al., *J. Virol.* 67:2529–2536 (1993).

There have been a number of structure-function studies of both the large and small delta antigens. The N-terminal third of the small delta antigen contains a putative coiled-coil sequence, Xia, Y. P. & Lai, M. M. C., *J. Virol.* 66:6641–6848 (1992), Wang, J. G. & Lemon, S. M., *J. Virol.* 67:446–454 (1993), Chang, M. F. et al., *J. Virol*, 67:2529–2536 (1993), comprising heptad repeats, which is followed by a linker domain which contains bipartite nuclear localization signal. Xia, Y. P. et al., *J. Virol.* 66:914–921 (1992). The middle portion of HDAg contains two arginine-rich motifs that have been shown to bind to the viral RNA. Lee, C. Z. et al., *J. Virol.*, 67:2221–2227 (1993). The C-terminal segment of s-HDAg is proline- and glycine-rich. Lazinski, D. W. & Taylor, J. M. *J. Virol.*, 67:2672–2680 (1993). L-HDAg is prenylated at the extreme C terminus and it is believed that this part of the molecule interacts with HBsAg and the membranes of the endoplasmic reticulum. Hwang, S. B. & Lai, M. M. C. *J. Virol.*, 67:7659–7662 (1993), de Bruin, W. et al., *Virus. Res.* 31:27–37 (1994). There is also some evidence that common segments of the large and small antigens may have subtly different conformations. Hwang, S. B. & Lai, M. M. C. *Virology* 193:924–931 (1993), Hwang S. B. & Lai, M M C, *J. Virol.* 68:2958–2964 (1994).

The coiled-coil domain has been shown to be required for a number of the functions of both small and large delta antigens. Mutations that destroy or alter the coiled-coil domain either greatly reduce or totally eliminate the ability of the HDAg-S to function as a trans activator of replication, Chang, M. F. et al., *J. Virol.*, 68:646–653 (1994), Chang, M. F. et al., *J. Virol.* 62:2403–2410 (1998), Lin, J. H. et al., *J. Virol.* 64:4051–4058 (1990), Chao, M. et al., *J. Virol.* 65:4057–4062 (1991), Xia, Y. P. et al., *J. Virol.*, 66:6641–6648 (1992). These same mutations also prevent the HDAg-L from inhibiting HDV RNA replication and inhibit its function in mediating the copackaging of the small antigen, Chang, M. F. et al., *J. Virol.*, 68:646–653 (1994), Chang, M. F. et al., *J. Virol.* 62:2403–2410, Lin, J. H. et al., *J. Virol.* 64:4051–4058 (1990), Chao, M. et al., *J. Virol.* 65:4057–4062 (1991). Transfection of cells undergoing HDV replication with a plasmid containing just the N-terminal one-third of the delta antigen (which contains the coiled-coil domain) inhibited HDV replication, Xia, Y. P. & Lai, M. M. C., *J. Virol.* 66:6641–6648 (1992). However, removal of the coiled-coil domain does not prevent the delta antigen from binding the viral RNA, Lin, J. H. et al., *J. Virol.*, 64:4051–4058 (1990) nor does it prevent the HDAg-L from packaging the viral RNA, Chen, P. J., et al., *J. Virol.*, 66:2853–2859 (1992). A "black sheep" model has been proposed for the mechanism of inhibition of the HDV replication. HDAg-L is believed to disrupt the homo-oligomeric small antigen multimers, essentially poisoning the HDAg-S complex. Xia, Y. P. & Lai, M. M. C., *J. Virol.*, 66:6641–6648 (1992). While the precise role of HDAg-S in replication of HDV is unknown, the protein is not a polymerase, and RNA amplification is thought to be mediated by host cell RNA polymerase II, MacNaughton, T. G. et al., *Virology* 184:387–390 (1991), Fu., T. B. & Taylor, J. et al., *J. Virol.* 67:6965–6972 (1993).

Biophysical studies were undertaken to examine the coiled-coil domain of HDAg. Rozzelle, J. E., Jr. et al., Proc. Natl. Acad. USA, 92:382–386 (1995). As described in Example 1, a peptide was synthesized that corresponded to residues 12 to 60 of the δ12–60(Y). This region includes the N-terminal heptad repeats. The peptide also included a C-terminal tyrosine so that the peptide could be labeled with I125 for use in a radioimmunoassay. The peptide sequence was conceptually divided into three segments based on the presence of two potential helix breakers Gly23 (G23) and Pro49 (P49); segments A (residues 12–24)(amino acids 1–13 of SEQ ID NOS:1–8), B (residues 25–49)(amino acids 14–38 of SEQ ID NOS:1–8), and C (residues 50–60) (amino acids 39–49 of SEQ ID NOS:1–8)(FIG. 1). The full-length peptide δ12–60(Y) and two shorter peptides that corresponded to regions A+B and B+C were synthesized. A number of biophysical experiments, including circular dichroism (CD), mass spectrometry, and analytical ultracentrifugation, clearly showed that the δ12–60(Y) peptide wa s largely helical and formed a coiled coil Rozzelle, J. E., Jr. et al., Proc. Natl. Acad. USA, 92:382–386 (1995). The shorter pepidese formed much less stable structures and were considerably less helical than δ12–60(Y). Human polyclonal antibodies from hemophilic patients who were chronic carriers of HBV and HDV reacted with the δ12–60 (Y) peptide, in both an ELISA and in a sandwich radioimmunoassay. Rozzelle, J. E., Jr. et al., Proc. Natl. Acad. USA, 92:382–386(1995), Wang, J. G. et al. J. Virol. 64:1108–1116. Subsequent studies indicated that monoclonal antibodies against the peptide recognized a conformational epitope only presented by the full-length peptide and not the shorter, extensively overlapping peptides, Rozzelle, J. E., Jr. et al., Proc. Natl. Acad. USA, 92:382–386 (1995).

Described herein for the first time is the crystal structure of the peptide δ12–60(Y) to 1.8 Å resolution. The structure reveals that the capsid protein dimerizes as an unusual antiparallel coiled coil. In the crystal structure, the dimers further oligomerize to form an octamer. The octamer forms an open, square planar structure with an antiparallel dimer forming each side of the square. Crosslinking and hydrodynamic studies suggest that both the peptide and the full-length short isoform exist as stable octamers in solution.

The structure of the peptide lends new insights into the mechanism by which HDAg dimerizes and further associates into higher ordered structures. The structure also explains why residues C-terminal to the predicted coiled-coil domain, and the helix-breaking proline residues are important for the stabilization of the coiled-coil structure. The peptide structure has important consequences for the in vivo oligomerization of HDAg. The unique octameric structure which is observed in the crystal structure also suggests that the N-terminus of the molecule may have a previously undetermined function.

When the HDAg open reading frame was originally examined, amino acids from residue 13 to 47 were identified as possibly forming a coiled coil. Glutaraldehyde cross-linking studies of full-length HDAg, as well as of the peptide, confirmed the formation of dimers, tetramers and higher-ordered structures, Wang, J. G. & Lemon, S. M., J. Virol., 67:446–454 (1993), Rozzelle, J. E., Jr. et al., Proc. Natl. Acad. USA, 92:382–386 (1995). The crystal structure of the peptide clearly shows how monomers come together to form antiparallel dimers as well as a higher-ordered octameric structure. The structure of a δ12–60(Y) also agrees well with previous circular dichroism studies of the peptide, which indicated that the two ends of the peptide (regions A and C) were important for the structural stability of the coiled coil. Rozzelle, J. E., Jr. et al., Proc. Natl. Acad. USA, 92:382–386 (1995). Shorter synthesized peptides that were missing either the A or C regions (A+B and B+C), were significantly less helical than the full-length peptide (A+B+C; 37%, 45% and 84% respectively at 37° C.). The peptide structure shows that hydrophobic residues from the N terminus of one monomer (region A), not involved in the heptad repeat, interact with residues outside of the predicted coiled-coil domain near the C terminus of the other monomer (region C) to form a hydrophobic core Trp20 (W20), Leu24 (L24), Trp50 (W50), Leu51 (L51) sandwiched between Arg13 (R13) and Arg24 (R24). This may stabilize the structure by keeping the ends of the helix from fraying. An additional stabilizing feature is a hydrogen bond between the sidechain of Glu45 (E45) and the indole nitrogen of Trp20 (W20). These hydrophobic residues, as well as the glutamic acid residue, are highly conserved in the 10 different strains of HDV identified to date (FIG. 1)(SEQ ID NOS:1–8). In fact, they are more conserved than those residues in the heptad repeat making up the hydrophobic core of the long helix (FIG. 1)(SEQ ID NOS:1–8).

As described in Example 3, cross-linking studies of full-length recombinant small delta antigen (r-HDAg-S or r-δAg-S) also demonstrated that the recombinant protein forms octamers in solution. This indicates that the octamer form seen in the crystal may not be an artifact of crystallization, but rather may represent the true state of the oligomerization of the delta antigen. A study by Chang and colleagues found that a deletion in the HDAg-L, just C terminal to the coiled-coil domain (residues 50 to 75), prevented the HDAg-S from being copackaged with the HDAg-L, Chang, M. F. J. Virol., 66:6019–6027 (1992). HDAg-L with this same deletion could not inhibit HDV replication, whereas a deletion in L-DHAg of residues 65 to 75 could. This suggested that the coiled-coil domain alone is not sufficient for the interaction between the large and small antigens, and that a subdomain between residues 50 and 65 is also necessary for this interaction. The crystal structure of δ12–60(Y) indeed shows the importance of residues between 50 and 60 in the formation of the peptide oligomer. They are not only involved in stabilizing the δ12–60(Y) dimer Trp50 (W50) and Leu51 (L51) but are also involved in the formation of the dimer-dimer interface Trp50 (W50), Ile54 (I54), and Ile58 (I58).

Prior to the studies described here, the overall organization of the HDAg oligomer was unknown. The structure of the δ12–60(Y) peptide suggests a number of interesting considerations about the function of the coiled-coil domain of the hepatitis delta antigen. For example, Lai and coworkers, Xia, Y. P. , et al. J. Virol. 66:6641–6648 (1992), inferring from previous data that showed that as little as 12% of HDAg-L is needed to inhibit 90% of viral activity, Chao, M., et al., J. Virol., 64:5066–5069 (1990), proposed that as little as one part of HDAg-L in eight parts of HDAg-S could inhibit viral replication. Their "black sheep model" proposed that the HDAg-L either disrupted the conformation of the oligomer of HDAg-S, therefore preventing it from binding to host factors, or that the presence of HDAg-L in the complex prevents the complex from interacting with host factors. This would seem in agreement with the peptide structure of octameric δ12–60(Y) and the results of the MALDI-TOF mass spectrometry analysis. If HDAg-L does disrupt the conformation of the oligomer of HDAg-S it probably does not do so directly through the multimerization domain, given that the large and small delta antigen share the same sequence within this region. Rather, it is possible that this $\alpha_7$ or $\alpha_n\beta_m$ structure can no longer interact with host factors. Also, since the C terminus of the L-HDAg interacts with the endoplasmic reticulum (ER) membrane and with HBsAg for assembly, it could redirect the complex elsewhere in the cell, preventing the nuclear translocation of s-HDAg which is required for HDV replication.

Discovery of the organizational structure also provides information regarding possible undetermined functions of the N terminus. The octamer that is formed by the peptide is reminiscent of proteins that form clamps around DNA, such as PCNA. Talluru, S. R., et al., Cell 79:1233–1243 (1994). The 50 Å hole formed by tile octameric structure is lined with basic side chains, suggesting that the N terminus of the protein not only may act as a dimerization/oligomerization domain, but also that it may function either as a clamp around the viral RNA or other nucleic acid or perhaps even function as a spool for nucleic acid. There is a report that peptides corresponding to the extreme N-terminal portion of the HDAg residues 2 to 27 and 2 to 17 can bind the viral RNA Poisson, F., et al., J. Gen. Virol. 74:2473–2478 (1993), Poisson, F. et al., J. Virol Methods 55:381–389 (1995). Since the δ12–60(Y) structure is missing residues 2 to 11, it is impossible to say what role they play in binding the viral RNA. Of the remaining residues, only Lys25 (K25) and Lys26 (K26), which point into the hole of the octamer, seem likely to play a role in binding RNA by potentially binding the phosphate backbone of the viral RNA.

The large size of the hole may be necessary to accommodate the viral RNA which is only 70% self complementary, and would possess a number of regions of bulged out single-stranded sequence, increasing the radius of gyration of the RNA as well as bending the RNA. Lilley, D. M. J., Proc. Natl Acad. Sci. USA, 92:7140–7142 (1995). The octameric structure also implies that there may be as many as four RNA-binding domains on each side of the octamer. This portion of the molecule may also bind another protein, especially one that is acidic, such as the recently discovered delta antigen interacting protein A (dipA), a cellular protein which has been found to interact with the HDAg Brazas, R. et al., Science 274:90–94 (1996) and, based on its amino acid sequence, would have an isoelectric point of 4.9.

Many investigators have referred to the putative coiled-coil domain of the delta antigen as a leucine zipper-like region. Experiments involving mutations in this region were interpreted assuming the coiled-coil domain of the delta antigen would resemble the parallel coiled-coil of the bZIP family of transcription factors, such as GCN4. HDAg dimerizes through an antiparallel coiled-coil domain, rather than a standard parallel coiled coil.

Although algorithms have been designed to determine the oligomerization state of a coiled coil, Woolfson, D. N., et al., *Protein Sci.* 4:1596–1607 (1995), Wolf, E., et al., *Protein Sci.* 6:1179–1189 (1997), they cannot determine the orientation of the predicted coiled coil. The discovery that this region forms an antiparallel coiled coil demonstrates that additional biochemical or genetic evidence, such as provided herein, is necessary to determine whether a predicted coiled-coil domain adopts a parallel or antiparallel conformation. Along with the structure of the δ12–60(Y) peptide, there are other examples of molecules that dimerize through antiparallel coiled-coil domains, such as the *Escherichia coli* regulatory protein AraC, Soisson, S. M., et al., *Science* 276:421–425 (1997) and the replication terminator protein from *Bacillus subtilis*, Bussiere, D. E. et al., *Cell* 80:651–660 (1995).

The hepatitis delta antigen (HDAg), the sole protein made by the hepatitis delta virus (HDV), is essential for viral replication in vivo. Oligomerization of the protein is necessary for both the transactivating function of the small delta antigen (HDAg-S) and the trans dominant inhibitory effect of the large delta antigen (HDAg-L). The structure of the peptide δ12–60(Y) that corresponds to the predicted coiled-coil domain of the hepatitis delta antigen HDAg suggests that delta antigen HDAg not only dimerizes through an antiparallel coiled coil, but also forms octamers. Interestingly, the coiled coil is stabilized by hydrophobic residues C terminal to the coiled-coil domain. These C-terminal residues interact with hydrophobic residues in the N terminus of the coiled-coil region. The hydrophobic core of the dimer is extended by further hydrophobic interactions at the interface between dimers in the octameric structure. In contrast to the rather promiscuous interactions between the coiled-coil domain, these unique interactions at the termini of the monomer and dimer interfaces might provide a good target for antivirals against HDV, since disruption of oligomerization can prevent replication in vivo.

The surprising octameric structure of the peptide suggests that the capsid of the delta antigen (HDAg) will look very different from the known structures of other viral nucleocapsid proteins. The octameric structure also suggests important implications for binding of HDAg to the viral RNA, since as many as four of the arginine-rich RNA-binding domains might be needed for binding to the viral RNA. The very basic hole in the octamer suggests that this portion of the molecule may act as a sort of "clamp" around an acidic molecule, such as viral RNA, another nucleic acid or a cellular factor.

The exact function of HDAg in viral replication is unclear. The protein may only function as a shuttle, binding to the viral RNA and transporting it into the nucleus of the infected cell. It is possible that HDAg functions to recruit host cell transcriptional machinery to the viral RNA. The discovery of the structure enables the design of experiments to determine whether the N terminus of the molecule has RNA-binding capabilities and investigate the mechanism of oligomerization and inhibition of small antigen by the large antigen. A systematic examination of the amino acids involved in dimerization and oligomerization would allow the determination of the mechanism by which HDAg-L inhibits HDAg-S. Furthermore, the unique interactions at the termini of the coiled-coil region provide a new framework to be exploited in the de novo design of stable antiparallel coiled coils.

The examples presented below are provided as further guidance and are not to be construed as limiting the invention in any way.

EXAMPLE 1

Synthesis of δ12–60(Y) Peptide

Materials and Methods

PEPTIDE SYNTHESIS: The δ12–60(Y) peptide was obtained by Erickson, B. and Lemon, S. M. and was synthesized and purified as described previously in Rozzelle, J. E. et al., *Proc. Natl. Acad. Sci. USA*, 92:382–386 (1995), incorporated herein by reference in its entirety.

The peptide (FIG. 11B) was assembled by fluorenylmethoxycarbonyl chemistry and purified by reversed-phase HPLC. It was $N_\alpha$-acetylated and $C_\alpha$-amidated. Crude peptide in 0.05% trifluoroacetic acid was separated on an octyl-silica column [$C_8$. Applied Biosystems, 250 mm×10 mm (i.d.), 300-Å pore size] by elution at 3 ml/min over 50 min with a linear gradient of 20–42% acetonitrile in 0.05% trifluoroacetic acid. Peptide δ12–60(Y) was eluted at 36% acetonitrile (monitored at 230 nm). The homogeneity of the individual fractions was determined on an analytical octyl-silica column. The expected mass of the peptide was confirmed by electrospray ionization (ESI) mass spectrometry: peptide δ12–60(Y), m/z 6034.1±1.2 (calcd. 6033.7).

Figure 11A:
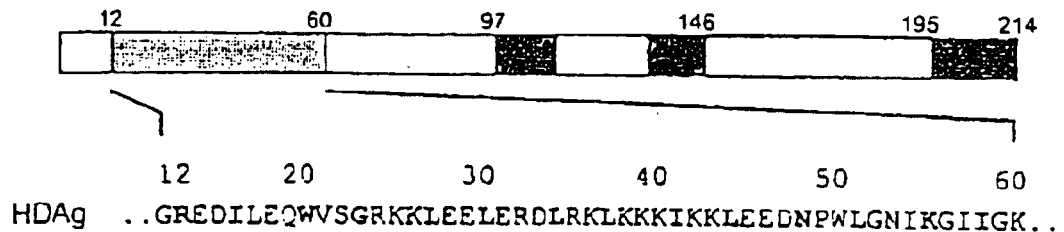
Figure 11B:
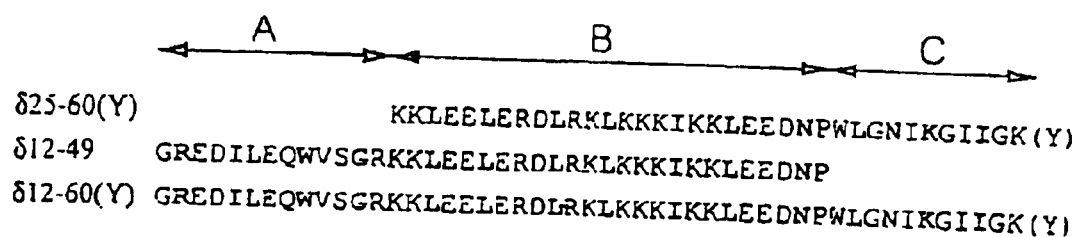

The peptide from the 12–60 region of HDAg was synthesized (FIG. 11B). Peptide δ12–60(Y) included segments A, B, and C. Segment B contains three heptads in which the first and fourth heptad positions are occupied by five leucines and one isoleucine, and is probably part of an α-helical coiled coil. A tyrosine residue, (Y), was added, $Lys^{60}$, to the C terminus of δ12–60(Y) to permit radioiodination.

CD SPECTROSCOPY. The α-helicity and the temperature at the midpoint of thermal denaturation ($T_m$) of the peptides were determined by CD spectroscopy. All three peptides had high α-helicity in PBS at 5° C. The ratio of the mean residue ellipticity of the negative bands near 222 nm and 208 nm ($[\theta_{222}]$)/($[\theta 208]$) is an indicator of coiled-coil formation. Values close to 1.0 indicate an α-helical coiled coil and values near 0.8 indicate isolated α-helices. At 5° C., this ratio was 0.98 for δ12–60(Y). At 37° C., this ratio was 0.94 for δ12–60(Y), consistent with persistence of a coiled-coil structure. In contrast, at 37° C. this ratio was only 0.79 for δ12–49 and 0.76 for δ25–60(Y), inconsistent with a coiled-coil structure.

EXAMPLE 2

Synthetic Gene for Optimized Expression of HDAg-S

Materials and Methods Expression Plasmids: pR5δV5 was constructed for the high-level expression of HDAg-S in *Escherichia coli*. The protein sequence of the American strain with the HDAg-S (GenBank accession no. M28267) was back-translated with the program BACKTRANSLATE. (This program was from the Wisconsin Package, versions 9.0, with *E. coli* codon frequencies obtained from gopher:// weeds.mgh.harvard.edu:70/ Oftp%3Aweeds.mgh.harvard.edu@pub/codon/eco.cod.) With the sequence obtained as shown in FIG. 9 (SEQ ID NO:10) and FIG. 18 (SEQ ID NOS:26–35), the plasmid pR5δV5 was constructed by a two-step PCR method, as described previously. Casimuro, D. R. et al., Biochemistry, 26:6640–6648(1995), with the exception that Vent polymerase (New England BioLabs) was used instead of Taq polymerase. Eight overlapping synthetic primers were synthesized (FIG. 9 (SEQ ID NO:10) and FIG. 18 (SEQ ID NOS:26–35)). Changes in the back-translated sequences were made so that the overlaps of the PCR primers would have approximately the same melting temperature. Primers were electrophoresed into a 10% sequencing gel, visualized by Uv shadowing, and excised from the gel. The primers were then purified with a Waters Sep-Pak column.

The first PCR contained 4 pmol of each of the eight primers in a 100-μl reaction mixture. Ten microliters of the first PCR was added to a second reaction mixture that contained an upstream primer (5'-GGGCATATGAGCCCGTAGCGA)(SEQ ID NO:34) and a downstream (5'-GCGCCATGGTTTACGGAAAG)(SEQ ID NO:35) primer designed to amplify the desired full-length product. Both reactions involved a hot start at 94° C. followed by 30 cycles of 1 min. at 94° C., 1 min at 57° C., and 1 min at 72° C., with a final 5-min extension at 72° C.

The PCR product from the second reaction was cloned into the vector pCR-Blunt (Invitrogen), which allows selection based on disruption of a toxic gene. Plasmids isolated from colonies were checked for the insert by restriction digest mapping. The open reading frame of HDAg-S was subcloned into expression vector pRSETb (Invitrogen). The sequence of the resultant plasmid, pR5δV5, was verified by dye termination sequencing.

PROTEIN PURIFICATION: Recombinant HDAg-S (δAg-S) was expressed and purified as follows. Plasmid pR5δV5 was transformed into BL21(DE3)pLysS cells (Novagen). A single colony was used to inoculate a 100-ml overnight culture. Ten milliters of this overnight culture was used to inoculate a 1-liter culture. At an optical density of between 0.4 and 0.6, the cells were induced with 3 ml of 100 mM IPTG (isopropyl-β-D-thiogalactopyranoside). Cell growth was continued for 3 h, and then cells were pelleted at 5,000×g for 10 min. The cells were resuspended in 15 ml of 50 mM HEPES (pH 7.5)-250 mM NaCl-1 mM $MgC_{12}$ and stored at −20° C. until needed.

The frozen cells (45 ml corresponding to three 1-liter cultures) were thawed, and one Complete Protease Inhibitor tablet (Boehringer Mannheim) was added, along with RNase A and DNase 1, to a final concentration of 50 μg/ml. Cells were lysed by sonication and pelleted at 10,000×g for 30 min. The lysate was diluted threefold with 50 mM HEPES buffer (pH 7.5) and then applied to a 10×1.5-cm Fast SP Sepharose column (Pharmacia) equilibrated with 50 mM HEPES buffer (pH 7.5) and eluted with a salt gradient from 0 to 1 M NaCl in 50 mM HEPES (pH 7.5). The fractions containing δAg-S were applied to a Superdex S-200 column (Pharmacia) equilibrated with 50 mM HEPES (pH 7.5), 500 mM NaCl, and 5% glycerol. The HDAg-S obtained was >85% pure as judged by Coomassie blue staining of a sodium dodecyl sulfate gel.

Proteins with a histidine tag were purified as follows. Proteins expressed in *E. coli* were affinity purified with a Talon column according to the recommendations of the manufacturer (Clontech). Proteins expressed in mammalian cells were purified by the Invitrogen Xpress System. In both cases, the fractions containing the purified protein were identified by sodium dodecyl sulfate gel electrophoresis, pooled, dialyzed, and concentrated.

TRANSFECTION: Plastic 16-mm-diameter tissue culture wells (Costar) were seeded with approximately $0.1×10^6$ Huh7 cells, Nakabayoshi, H. et al. i Cancer Res., 42:3858–3863 (1982). For transfections with assembled RNP, 0.25 to 900 ng of HDAg-S and 500 ng of genomic HDV RNA in 125 μl of Opti-MEM were combined with 2.7 μl of lipofectamine (2 mg/ml) in 125 μl of Opti-MEM, incubated for 30 min at room temperature, and applied to cells that had been washed with Opti-MEM (Hawley-Nelson, P. et al., *Focus*, 15:73–79(1993)). In control transfections, either HDAg-S or HDV RNA was omitted. For cDNA transfections, 500 ng of plasmid DNA was used. At 5 h after transfection, the transfection mixture was changed to Dulbecco's modified Eagle's medium supplemented with 10% fetal calf serum. At 4 days after transfection, cells were reseeded into a 30-mm-diameter dish containing a glass coverslip; at 8 days, the cells were examined by immunofluorescence microscopy. Eight days length was chosen for three reasons: (1) to avoid detection of the transfected HDAg-S; (ii) In the immunofluorescence assays, 8 days corresponded to the peak signal for a cell undergoing RNP-iniated replication; (iii) At 8 days, HDAg-L, created as a consequence of both RNA editing and genome replication, could be readily detected (Luo et al. *J. Virol.*, 64:1021–1027 (1990)). In contrast, for Northern analyses, genome replication was detectable as early as 2 days.

Results

Initial studies with *E. coli* demonstrated poor expression of HDAg-S from the wild-type sequence. About 18% of the codons in the natural HDAg sequence are rarely used by *E. coli*. Attempted overexpression of codons that are rare in *E. coli* not only can inhibit expression but also can lead to misincorporation (Del Tito, B. J. et al., J. Bacterial, 177:7086–7091 (1995) Therefore, a nucleotide sequence was designed which maintained the amino acid sequence, but increased the percentage of codons that were most favored for expression in *E. coli* from 26% to 85%. This optimized sequence FIG. 9 (SEQ ID NO:10) was used to construct expression plasmid pR5δV5. Thus, a 40-fold increase in expression was obtained and the recombinant protein was purified to >85% homogeneity.

EXAMPLE 3

Structure Determination

Materials and Methods

CRYSTALLIZATION AND DATA COLLECTION: The peptide δ12–60(Y) was dissolved in 50 mM acetate, pH 4.8, 50 mM NaCl and brought to a concentration of 15 mg/ml. The crystals of the δ12–60(Y) peptide were grown at 22° C. by the vapor diffusion method. The peptide (2 μl of a 15 mg/ml solution) was mixed with 2 μl of the reservoir solution containing 100 mM sodium acetate, pH 4.8, and 100 mM sodium citrate, pH 5.6, on a coverslip and then inverted over the reservoir solution. Crystals appeared within 3–4 days, and grew as large as 0.5×0.3×0.3 mm. Crystals belonged to space group $P2_12_12$ with unit cell parameters a=109.2 Å, b=85.3 Å, c=29.4 Å, α=β=γ=90°. When attempts to find a heavy atom derivative failed, a peptide was synthesized with serine 22 replaced by a cysteine, δS22C12–60(Y). The δS22C12–60(Y) peptide was reacted with an excess of platinum terpyridine, dialyzed overnight against water, and then freeze-dried. The peptide was then reconstituted at 15 mg/ml in 50 mM acetate, 50 mM NaCl, 5 mM DTT, pH 4.8, and crystallized by the same conditions as that of the wild type-peptide. This peptide crystallized isomorphously with the δ12–60(Y).

The coverslips containing the crystals were inverted and cryosolvent (reservoir solution containing 30% glycerol) was slowly mixed with the drops and continuously replaced until no mixing was observed. The crystals were mounted in nylon loops and frozen directly in the nitrogen stream. Crystals used at Brookhaven were stored in liquid nitrogen until the time of data collection. Two native data sets were collected at Beamline X12C at the National Synchrotron Light Source at Brookhaven National Lab using X-rays of wavelength 1.15 Å (Table 1). The heavy atom data set was collected on a Siemens rotating anode with a multiwire detector (Table 1). Data from the native crystals was processed using DENZO, Otwinowski, Z. SERC Daresbury Laboratory, Warrington, UK:(56–62 (1993)) and SCALEPACK. Data from the heavy atom derivative was integrated using the program BUDDHA (Blum, M. et al., *J. Appl. Cryst*. 20:235–242 (1987)) and processed using ROTAVATA and AGROVATA from the CCP4 package (CPP4 *Acta. Cryst. D*., 50:760–763 (1994)). Structure factors from both data sets were calculated using TRUNCATE (CPP4, supra). Data from the native and derivative were scaled together using SCALEIT (CPP4, supra).

STRUCTURE DETERMINATION AND MODEL BUILDING: The positions of the heavy atom sites were determined using SHELXS-86 (Sheldrick, G. M., *Acta. Cryst. A*. 46:467–473 (1990)). The positions of the heavy atom sites were refined using MLPHARE (Otwinowski, Z., *Proceedings of the CCP4Study Weekend*, 80–86 SERC Daresbury Laboratory, Warrington, UK (1991)), and initial SIRAS phases were calculated. The data was then subjected to a round of solvent flattening with histogram matching using DM (Zhang, K. Y. J. & Main, P. *Acta. Cryst. A*. 46:41–46 (1990). A map was calculated which clearly showed the position of the two dimers in the asymmetric unit, and an initial model was built into the initial SIRAS map using the program O (Jones, T. A. et al. *Acta Cryst. A*., 47:110–119 (1990)). The structure was refined using X-PLOR ,3.8.9, Brünger, A. T., *Yale University Press*, New Haven, Conn. (1992). Rounds of positional refinement, followed by simulated annealing and B-factor refinement, were carried out with rebuilding of the structure using O between cycles of refinement. During the initial model building and refinement, omit maps, which excluded 10 residues at a time, were used to check the progress of refinement.

SURFACE AND ELECTROSTATIC CALCULATIONS: Surface calculations were performed using the surface option in QUANTA version 4.0. Electrostatic calculations were performed with GRASP version 1.3.

PROTEIN EXPRESSION AND PURIFICATION: The pR5δV5 plasmid, Dingle, K. et al. *J. Virol*., 72(6):4783–4788 (1998) which contains a synthetic gene for the small delta antigen, HDAg-S, was transformed into BL21 (DE3)pLysS cells (Novagen) and purified as described previously in Example 2. See also Dingle, K. et al., supra. Briefly, 45 ml of frozen cells, corresponding to three 1 L cultures, were thawed and one protease inhibitor tablet (Boehringer Mannheim) was added, as well as RNAse A and DNAse I to a final concentration of 50 μg/ml. Cells lysed by sonication were pelleted at 10,000×g for 30 minutes. The lysate was diluted three-fold with 50 mM HEPES buffer, pH 7.5, and then applied to a 10×1.5 cm Fast SP Sepharose (Pharmacia) column equilibrated with 50 mM HEPES buffer, pH 7.5, and eluted using a salt gradient from 0–1M NaCl in 50 mM HEPES, pH 7.5. The fractions containing recombinant small delta antigen (rδAg-S [r-HDAg-S]) were assayed using SDS-PAGE and pooled. The sample was then applied to a Superdex S-200 column (Pharmacia) equilibrated with 50 mM Hepes, pH 7.5, 500 mM NaCl and 5% glycerol. The elution of the protein from the column was monitored by UV absorbance at 280 nm.

Results

Attempts to find a heavy atom derivative using the peptide with the wild-type sequence of the American strain of HDAg failed. Thus, a new peptide was synthesized with a cysteine replacing serine 22 (Ser22)(this residue demonstrates considerable variation in different strains of HDV, (FIG. 1)(SEQ ID NOS:1–8). The cysteine mutant and wild-type peptides crystallized isomorphously. The presence of cysteine 22 (Cys22) allowed the preparation of a platinum terpyridine derivative, facilitating the determination of the structure using SIRAS methods (Table 1). Retrospective examination of the model confirmed that the Pt was bound to the sulfur of cysteine 22 (Cys22).

The solvent-flattened map was easily interpretable, and clearly showed two dimers in the asymmetric unit. Rounds of positional refinement, simulated annealing, temperature factor refinement using X-PLOR (Brünger, A. T., *Yale University Press*, New Haven, Conn.(1 992)), and manual rebuilding using O (Jones, T. A. et al. *Acta Cryst. A*. 47:110–19 (1990)), led to the current model (Table 2, FIG. 2). The current model has an R factor of 22.5% and a free R factor of 27% with good geometry (r.m.s.d. bond 0.007 Å and r.m.s.d. bond angles 1.0°). A number of sidechains exposed to the large solvent channel, as well as the first residue in the chain and the last residue in one of the chains, are disordered. The four monomers in the asymmetric unit superimpose well onto one another, with an average r.m.s.d. for mainchain atoms of 0.81 Å and for all non-hydrogen atoms 1.51 Å. The main differences in the monomers are those residues involved in crystal packing interactions.

The coordinates have been deposited in the Brookhaven Protein Data Bank (accession number 1A92).

Figure 3B:
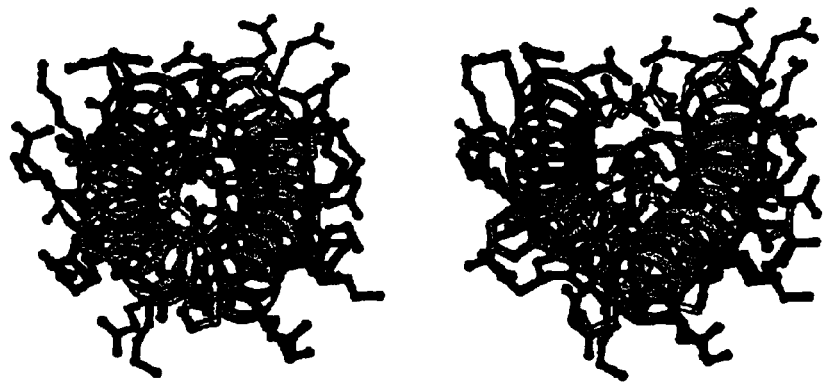

Each monomer is composed of a long, N-terminal helix, approximately 60 Å in length, interrupted by a sharp bend at proline 49 (Pro49), and continuing on into another short helix. The long helices of each of two monomers wrap around each other forming an antiparallel coiled coil (FIG. 3a, FIG. 3b), which straightens out at the N terminus. Only one of the four possible salt bridges between Glu31 (E31) and Lys38 (K38) is seen. In the other three cases, the charged groups are slightly farther apart (3.8Å, 4.2 Å and 4.4 Å versus 2.9 Å) and the sidechains are hydrogen bonded to nearby solvent molecules. The sidechain of Glu45 (E45) is hydrogen bonded to the indole nitrogen of Trp20 (W20). The sidechain of Asn48 (N48), which is located at the C terminus of the long helix, completes the hydrogen-bonding pattern of the helix by making a hydrogen bond back to the mainchain oxygen of Leu44 (L44). The formation of the dimer buries 2650 Å$^2$ of surface area, approximately 26% of the total surface area.

Figure 4:
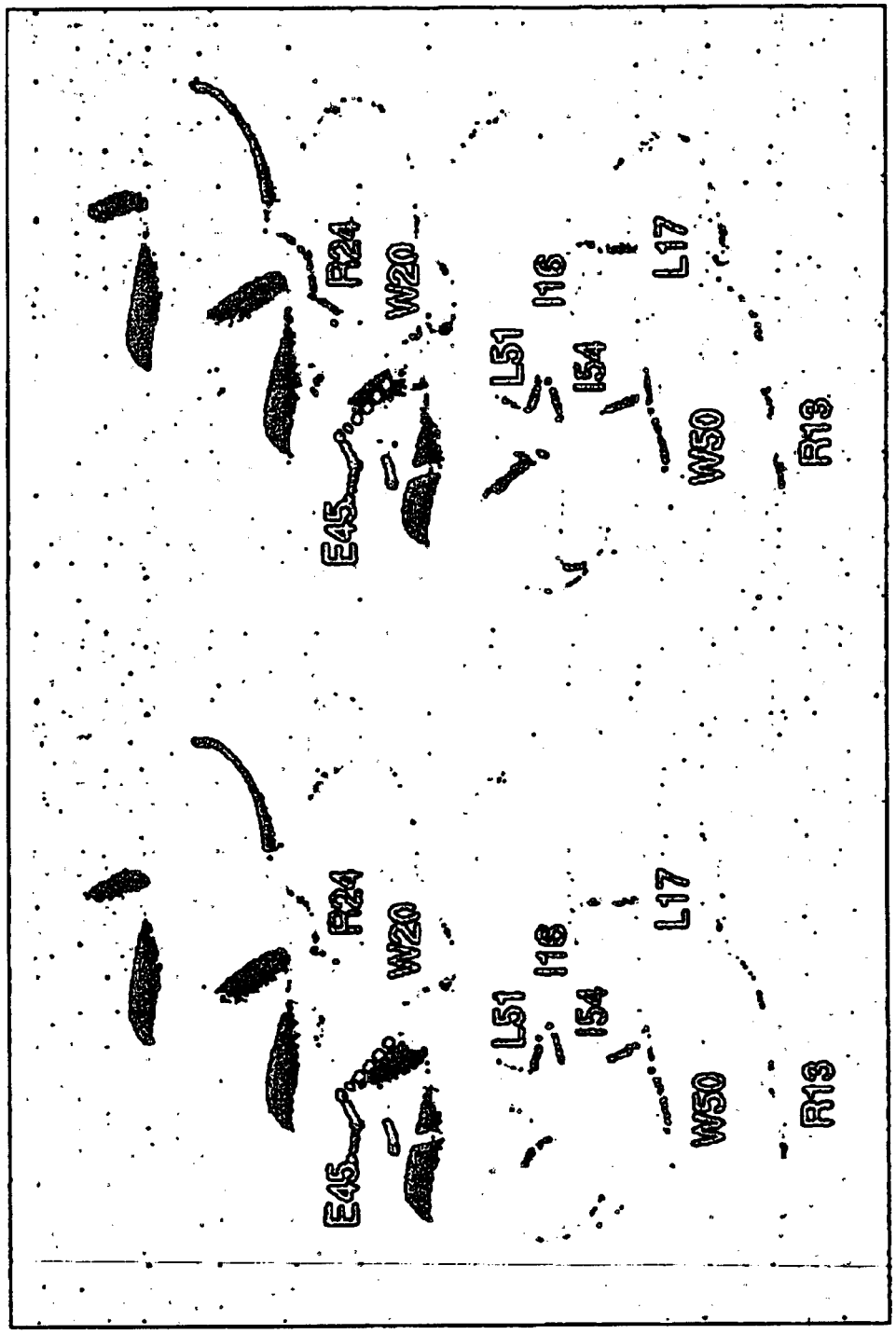

Although the majority of residues in the heptad repeat (FIG. 3C)(SEQ ID NO:9) of the predicted coiled-coil region do pack as expected, Trp20 (W20) does not. Even though the Cα-Cβ vector of Trp20 (W20) points out of the interface as would be expected for a sidechain in the a position of a heptad repeat, the sidechain of Trp20 is flipped away from the core of the coiled coil and into a hydrophobic region formed between segment A (residues 12–24) of one monomer, and segment C (50–60) of its partner within the peptide dimer. The dimer shows primarily hydrophobic interactions between residues in the A and C regions. Ile16 (I16), Leu17 (L17), Trp20 (W20), Trp50 (W50), and Leu51 (L51) are the sidechains primarily involved in this hydrophobic region, which is capped by the aliphatic portion of the sidechains of Arg13 (R13) and Arg24 (R24)(FIG. 4). The primary non-hydrophobic, monomer-monomer interactions near this region involve the formation of a hydrogen bond between Trp20 (W20) and Glu45 (E45)(FIG. 4). The heptad repeat is also unusual in that it contains a glycine at position 23. If the monomers were oriented in a parallel fashion, a large hole in the middle of the hydrophobic core of the dimer would result. However, since the strands are arranged antiparallel, the large sidechain of Ile41 (I41) packs into the hole formed by Gly23 (G23). The dimer is stabilized by hydrophobic interactions other than the residues in the heptad repeat. Residues from the N-termini of each monomer, Ile16 (I16), Leu17 (L17), Trp20 (W20) from one monomer and Trp50 (W50), Leu51 (L51), and Ile54 (I54)

from the other, form a hydrophobic core which is protected from solvent by the aliphatic portions of Arg13 (R13) and Arg24 (R24). There is also a hydrogen bond between the sidechain of Glu45 (E45) and the indole nitrogen of Trp20 (W20) (O—N distance 2.8 Å).

Figure 5:
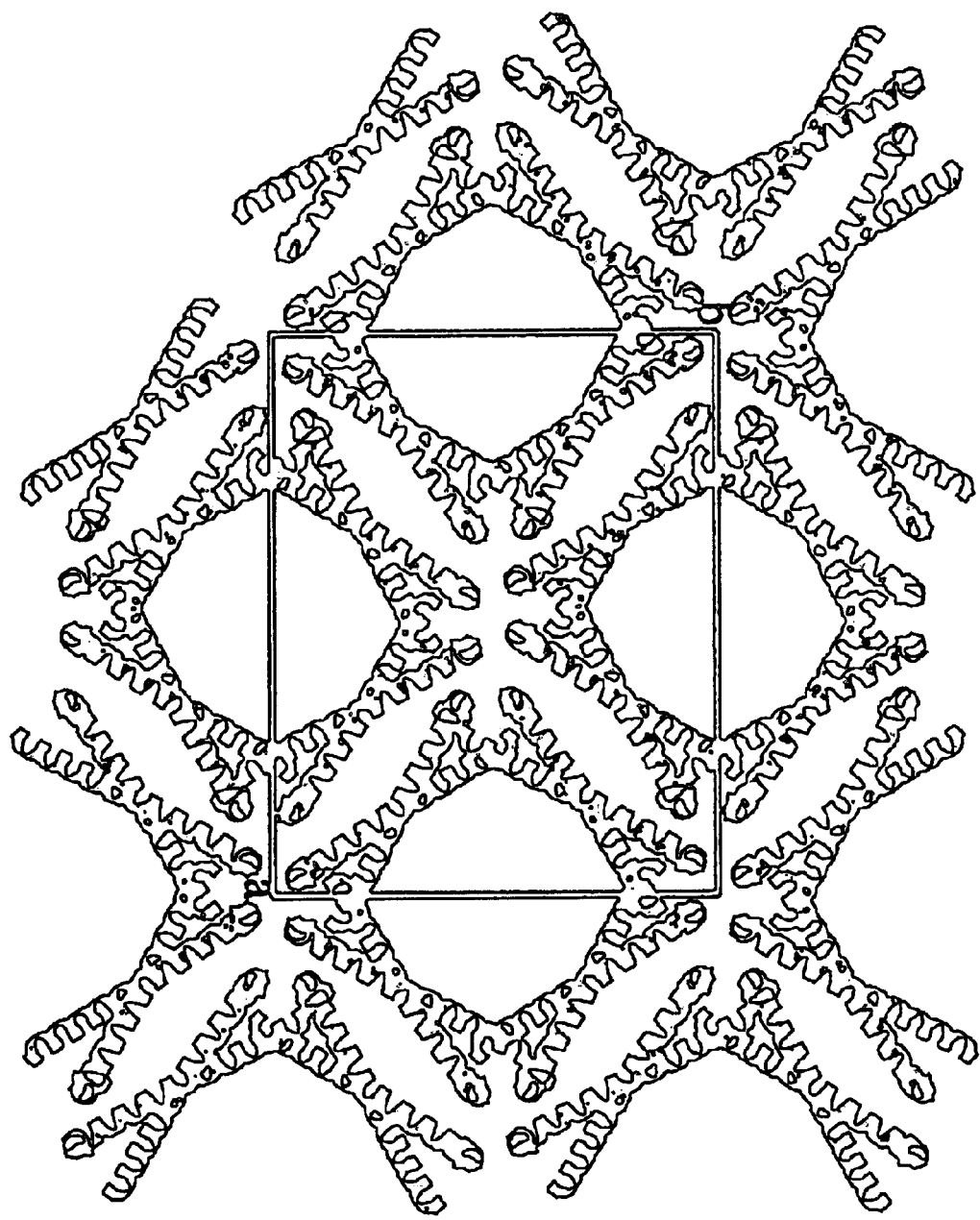
Figures 6A, 6B:
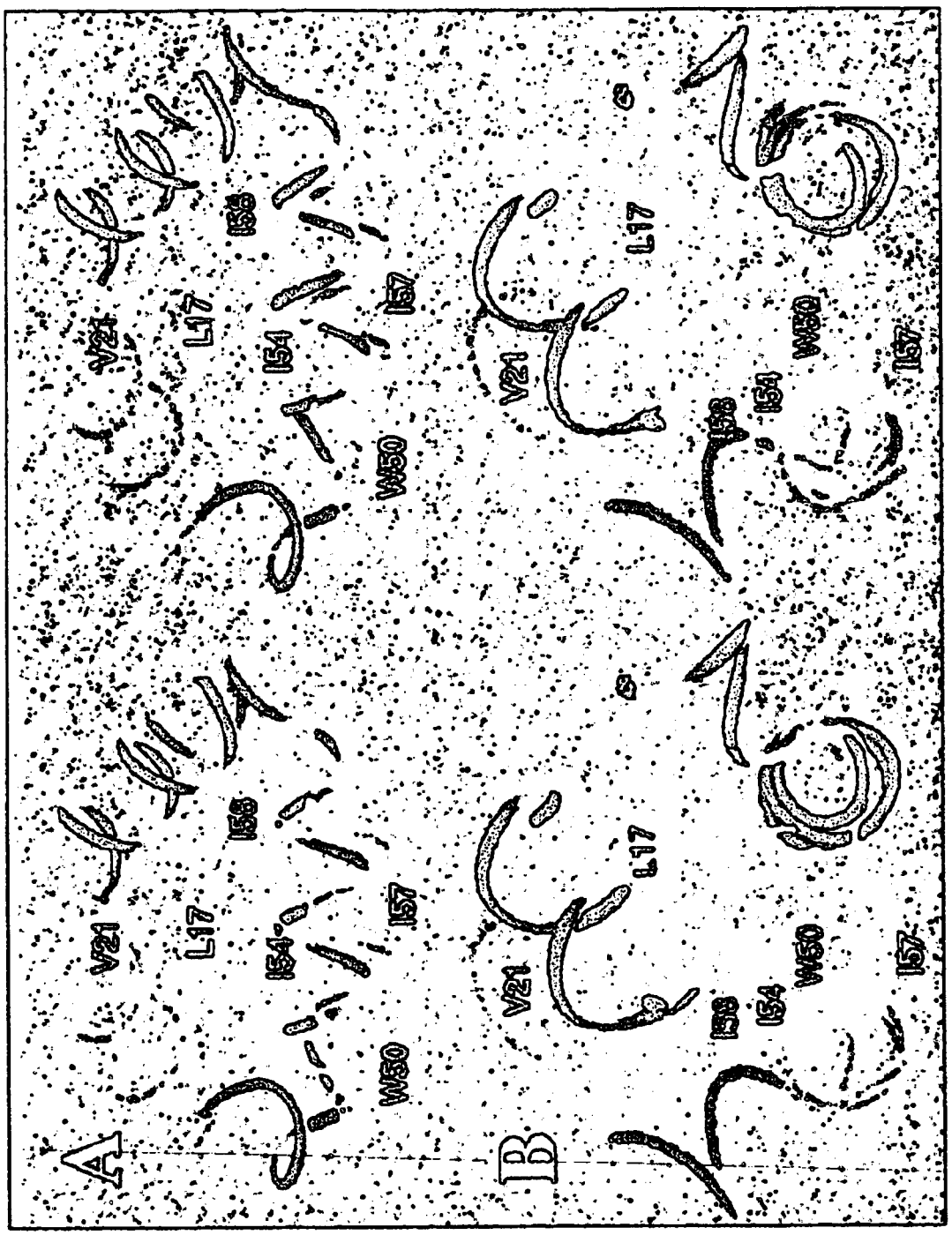
Figures 7A, 7B:

In the crystal, each dimer associates with three other dimers to form a doughnut-like octamer (FIG. 5). The octameric complex forms a pseudo-centered (C222) cell. The octamer is widely open with a central "hole", 50 Å in diameter. The open structure of the octamer is reminiscent of several other proteins, including Proliferating cell nuclear antigen (PCNA), in which the hole that is formed is believed to encircle DNA (Talluru, S. R. et al., *Cell*, 79:1233–1243 (1994)). It is this octameric structure which is the translational repeating unit in the crystal (FIG. 5). The dimer-dimer interface is a four-helix bundle formed across the crystallographic two-fold axis. The interface of the two dimers consists of hydrophobic residues in region A of the coiled-coil domain Leu17 (L17) and Val21 (V21) but also includes residues C-terminal to the coiled-coil domain, region C, between residues 50 to 60 Trp50 (W50), Ile54 (I54), Ile57 (I57) and Ile58 (I58)(FIG. 6). Thus, hydrophobic residue from both helices pack in the interface, essentially extending the hydrophobic core mentioned above. Trp50 is involved in both the formation of the dimer as well as the octamer. Formation of the octamer buries an additional 800 Å$^2$ of surface area per monomer, which means that approximately 40% of the total surface area of each monomer is buried. The 50 Å diameter hole framed by the four dimers is lined with basic sidechains (FIGS. 7a and b). The hole is large enough to accommodate an RNA molecule. Residues Lys26 (K26) and Lys38 (K38) which had been modeled in as alanine were changed to lysine for this calculation. The electrostatic surface was calculated using GRASP (Nicholls, A. *Columbia University*, New York, N.Y. (1992)), and rendered using RASTER3D (Merritt, E. A. & Murphy, M. E. P.,*Acta. Cryst. D*. 50:869–873 (1994)).

TABLE 1

Data Collection Statistics

| | Native* | S22C Pt |
|---|---|---|
| Spacegroup | P2$_1$2$_1$2 | P2$_1$2$_1$2 |
| Unit cell (a, b, c) | 109.2, 85.3, 29.4 | 110.3, 86.3, 29.6 |
| Temperature of data collection (° C.) | −160 | −165 |
| Resolution (Å) | 15–1.73 | 86–2.5 |
| Number of reflections | 221,286 | 44,362 |
| Number of unique reflections | 28,279 | 10,013 |
| Completeness† (%) | 94 (35) | 97 |
| I/σ† | 51 (7) | 6.0 |
| Multiplicity | 7.8 | 4.4 |
| R$_{sym}$†‡$ (%) | 4.2 (18) | 6.7 [14.0] |
| R$_{iso}$¶ (%) | — | 30.5 |
| R$_{cullis}$# | — | 0.62 (0.52) |
| R$_{cullis\ anom}$¥ | — | 0.84 |
| Phasing power** | — | 2.2 (1.7) |

*Data are from two crystals.
†Numbers in parentheses represent values in the highest resolutions shell.
‡R$_{sym}$ = Σ$_{(h,k,l)}$|I$_{(h,k,l)}$ − <I$_{(h,k,l)}$>|/Σ$_{(h,k,l)}$ <I$_{(h,k,l)}$>, where <I$_{(h,k,l)}$> represents the sigma weighted average intensity of symmetry-equivalent reflections.
$The number in square brackets represents R$_{anom}$ = Σ|<I+$_{(h,k,l)}$> − <I−$_{(h,k,l)}$>|/Σ(<I+$_{(h,k,l)}$> + <I−$_{(h,k,l)}$>), where <I+/−$_{(h,k,l)}$> represents the statistically weighted average intensity of symmetry-equivalent reflections.
¶R$_{iso}$ = Σ$_{(h,k,l)}$|(F$_{PH}$ − F$_P$)|/Σ(F$_P$).
R$_{cullis}$ = Σ$_{(h,k,l)}$||F$_{PH}$| − |F$_P$ + F$_H$||/Σ$_{(h,k,l)}$|F$_{PH}$ − F$_P$|; number in parentheses represents R$_{cullis}$ for centric reflections.
¥R$_{cullis\ anom}$ = Σ$_{(h,k,l)}$||F$_{PH+}$ − F$_{PH−}$|$_{obsvd}$ − |F$_{PH+}$ − F$_{PH−}$|$_{calc}$|/Σ$_{(h,k,l)}$|F$_{PH+}$ − F$_{PH−}$|$_{obsvd}$
**Phasing power = <|F$_H$|/||F$_{PH}$| − |F$_P$ + F$_H$||>; number in parentheses is the power for centric reflections.

TABLE 2

Refinement Statistics

| | |
|---|---|
| Resolution range (Å) | 15–1.8 |
| R$_{working}$*(%) | 22.5 |
| R$_{free}$†(%) | 27.0 |
| Non-hydrogen protein atoms | 1785 |
| Solvent atoms | 114 |
| Rms from ideal geometry | |
| bond lengths (Å) | 0.007 |
| bond angles (°) | 1.0 |
| dihedral angles (°) | 16.9 |
| impropers (°) | 0.59 |
| Average B factor overall (Å$^2$) | 29.3 |
| mainchain | 22.5 |
| sidechain | 32.4 |
| solvent | 34.7 |

*R$_{working}$ = Σ$_{(h,k,l)}$(|F$_o$| − |F$_c$|)/Σ(F$_o$), for a working set composed of 90% of the data.
†R$_{free}$ = Σ$_{(h,k,l)}$(|F$_o$| − |F$_c$|)/Σ(F$_o$), for a test set composed of 10% of the data selected randomly.

EXAMPLE 4

Mass Spectrometry

Materials and Methods:

r-HDAg-S was prepared as described above. The samples for mass spectrometry were prepared as follows: the r-HDAg-S was dialyzed overnight against water. Cross-linked protein was prepared by the addition of 5 μl of 0.5% glutaraldehyde to 40 μl of rHDAg-S for 5 minutes, and quenched by the addition of 5 μl of 1M ammonium acetate. Mass spectrometry was performed in the BCMP Biopolymer facility on a Persceptive Biosystems Voyager-DE mass spectrometer.

Results

Figure 8A:
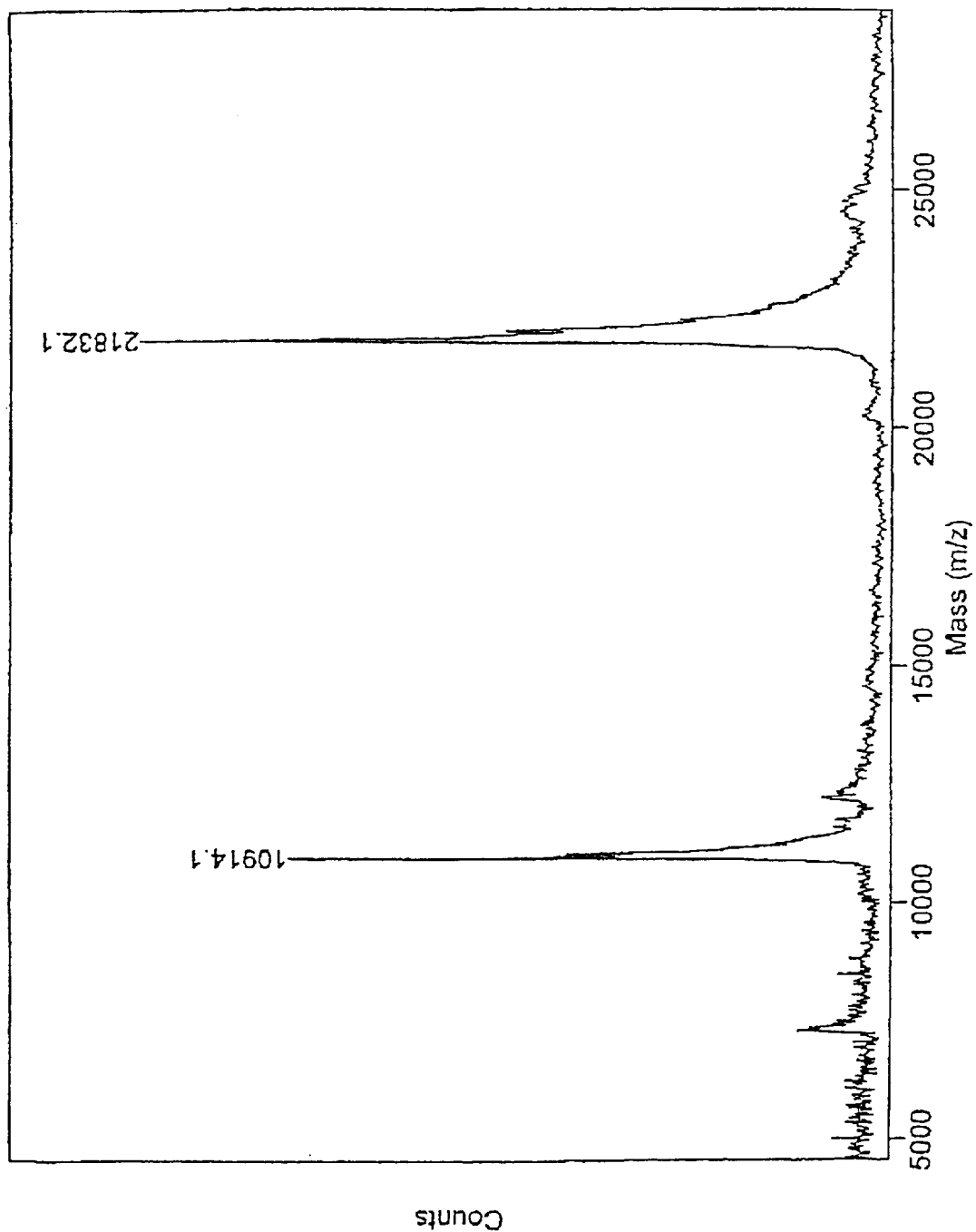
Figure 8B:
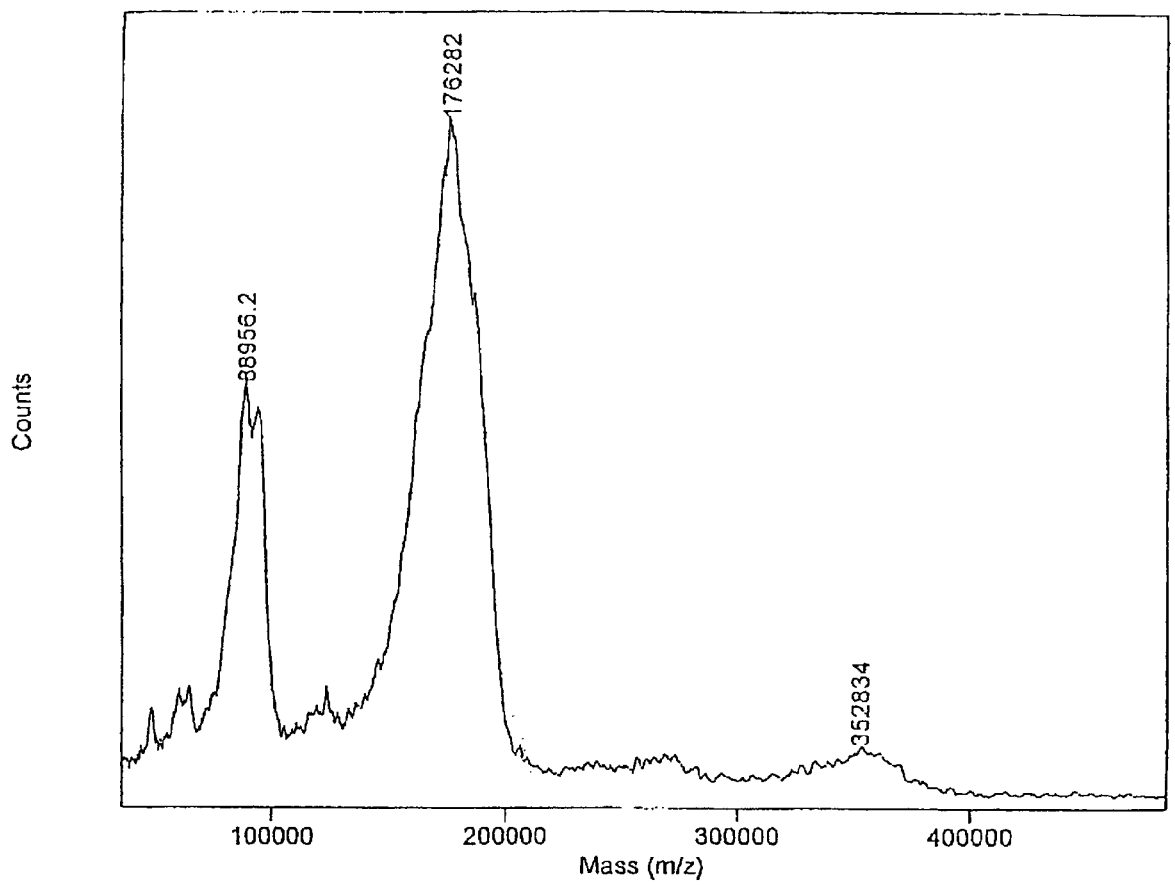

Previous studies have suggested that both the peptide and natural HDAg derived from infected liver form multimers in solution (Wang, J. G. & Lemon S. M. *J. Virol*, 67:446–454 (1993)), (Rozzelle, J. E., Jr. et al. *Proc. Natl. Sci. USA*, 92:382–386 (1995)). In order to investigate the significance of the octamer formed by the peptide, MALDI-TOF mass spectrometry was used to determine the mass of monomeric and oligomeric forms of recombinant small delta antigen, r-HDAg-S. The uncrosslinked protein has a mass of 2,1832 Da (FIG. 8A), which is the correct mass within 0.01% of the amino acid sequence of the American strain of the small delta antigen (HDAg-S) (Genbank accession #-M28267) minus the first methionine residue. The primary species of the cross-linked rHDAg-S had a mass of 176,282 Da (FIG. 8B). The M+1 and M+2 peaks of the octamer were the only significant peaks in the spectrum. The ratio of the masses of the cross-linked species to the monomer is 8.1:1.

While this invention has been particularly shown and described with references to preferred embodiments thereof, it will be understood by those skilled in the art that various changes in form and details may be made therein without departing from the spirit and scope of the invention as defined by the claims.

What is claimed is:

1. A fusion molecule consisting of (a) a peptide consisting of amino acids 12 to 88 of the hepatitis delta antigen (HDAg) or a fragment thereof that forms a coil and (b) at least one binding moiety.

2. The fusion molecule of claim 1 wherein the binding moiety is selected from the group consisting of an antigen, an antibody, a single chain antibody, a ligand, a receptor, an enzyme, an oligonucleotide, a promoter binding protein, a label, a growth factor, a cytokine, a nuclease, or a drug.

3. The fusion molecule of claim 1 which is a fusion protein.

4. The fusion molecule of claim 1 wherein (a) and (b) are chemically linked.

5. The fusion molecule of claim 1 wherein the (a) and (b) are expressed as a single unit.

6. A coiled-coil oligomer comprising at least two fusion molecules of claim 1, wherein the coiled-coil structure of said coiled-coil oligomer occurs between the hepatitis delta antigen (HDAg) peptides of each of the at least two fusion molecules.

7. The coiled-coil oligomer of claim 6 which is an octamer.

8. The coiled-coil oligomer of claim 6 wherein two fussion molecules are the same.

9. The coiled-coil oligomer of claim 6 wherein two fusion molecules are different.

10. A method of binding binding partners comprising contacting a fusion molecule of claim 1 having a first binding moiety with a second binding moiety, wherein the first and second moieties are binding partners, under conditions suitable for binding.

11. The method of claim 10 wherein the fusion molecule consists of (a) a peptide consisting of amino acids 12 to 88 of the hepatitis delta antigen (HDAg) or a fragment thereof that forms a coil and (b) at least two binding moieties, wherein one binding moiety is the first binding moiety and another binding moiety is the second binding moiety.

12. The method of claim 10 wherein the binding between binding partners occurs in solution.

13. The method of claim 10 wherein the fusion molecule is a subunit of a coiled-coil oligomer, wherein the coiled-coil structure of said coiled-coil oligomer occurs between the hepatitis delta antigen (HDAg) peptide of said fusion molecule and another peptide which consists of amino acids 12 to 88 of the hepatitis delta antigen (HDAg) or a fragment thereof that forms a coil.

14. The fuision molecule of claim 1 wherein the binding moiety is selected from the group consisting of cytokines, tumor necrosis factor, interferons, interleukins, adenosine deaminase, insulin, T-cell receptors, soluble CD4, epidermal growth factor, human growth factor, cytochrome b, glucocerebrosidase, ApoE, ApoC, ApoAI, the LDL receptor, Fc receptors, plasminogen activators, dopamine, MHC, tumor suppressor genes, monoclonal antibodies, antigen binding fragments of monoclonal antibodies, drug resistance genes and ion channels.

15. An isolated and purified fusion molecule consisting of:
 (a) a polypeptide having an amino acid sequence selected from the group consisting of SEQ ID NOS:1–8, amino acids 12–48 of SEQ ID NOS:1–8, amino acids 12–60 of SEQ ID NOS:1–8, SEQ ID NO:9, SEQ ID NO:11, amino acids 12–48 of SEQ ID NO:11, amino acids 12–60 of SEQ ID NO:11, SEQ ID NOS:15–20, SEQ ID NO:25, and fragments thereof that form a coil; and
 (b) at least one binding moiety.

16. A peptide consisting of amino acids 12 to 88 of the hepatitis delta antigen (HDAg) wherein a serine residue is substituted with cysteine.

17. An isolated and purified molecule comprising:
 (a) a polypeptide consisting of an amino acid sequence of amino acids 12–88 of the hepatitis delta antigen (HDAg), or a fragment thereof which forms a coiled coil oligomer when contacted with a peptide consisting of amino acids 12 to 88 of HDAg or a fragment thereof that forms a coil; and
 (b) a nuclear localization signal.

* * * * *